(12) United States Patent
Bhatia et al.

(10) Patent No.: US 9,365,821 B2
(45) Date of Patent: Jun. 14, 2016

(54) TRANSFORMED HUMAN PLURIPOTENT STEM CELLS AND ASSOCIATED METHODS

(71) Applicant: McMaster University, Hamilton (CA)

(72) Inventors: Mickie Bhatia, Hamilton (CA); Tamra Werbowetski-Ogilvie, Hamilton (CA); Eleftherios Sachlos, Hamilton (CA); Daniela Fischer Russell, Hamilton (CA); Sarah Laronde, Hamilton (CA); JungBok Lee, Hamilton (CA); Eva Szabo, Hamilton (CA); Ruth Risueno, Barcelona (ES)

(73) Assignee: MCMASTER UNIVERSITY, Hamilton, Ontario (CA)

( * ) Notice: Subject to any disclaimer, the term of this patent is extended or adjusted under 35 U.S.C. 154(b) by 117 days.

(21) Appl. No.: 14/329,412

(22) Filed: Jul. 11, 2014

(65) Prior Publication Data

US 2015/0038371 A1 Feb. 5, 2015

Related U.S. Application Data

(63) Continuation of application No. 13/393,475, filed as application No. PCT/CA2010/001340 on Sep. 1, 2010, now abandoned.

(60) Provisional application No. 61/238,806, filed on Sep. 1, 2009, provisional application No. 61/238,822, filed on Sep. 1, 2009.

(51) Int. Cl.
*C12N 15/00* (2006.01)
*C12N 5/0735* (2010.01)
*G01N 33/50* (2006.01)
*C12N 5/095* (2010.01)

(52) U.S. Cl.
CPC ............ *C12N 5/0606* (2013.01); *C12N 5/0695* (2013.01); *G01N 33/5073* (2013.01); *C12N 2501/115* (2013.01); *G01N 2500/10* (2013.01)

(58) Field of Classification Search
CPC ..................................................... C12N 5/0606
See application file for complete search history.

*Primary Examiner* — Valarie Bertoglio
(74) *Attorney, Agent, or Firm* — Ferris H. Lander, Inc.

(57) ABSTRACT

The present disclosure provides transformed human pluripotent stem cell (t-hPSC). t-hPSCs are not dependent on Oct4 for renewal and survival, however exhibit a sensitivity to reduced levels of the transcription factor Nanog. Also provided are methods of culturing cells for use in a cell-based screening assay comprising placing one or more transformed human pluripotent stem cells into a receptacle and culturing said stem cells in the receptacle to form a monolayer of stem cells without cell overlap. Methods of screening compounds using t-hPSCs are also described.

5 Claims, 46 Drawing Sheets

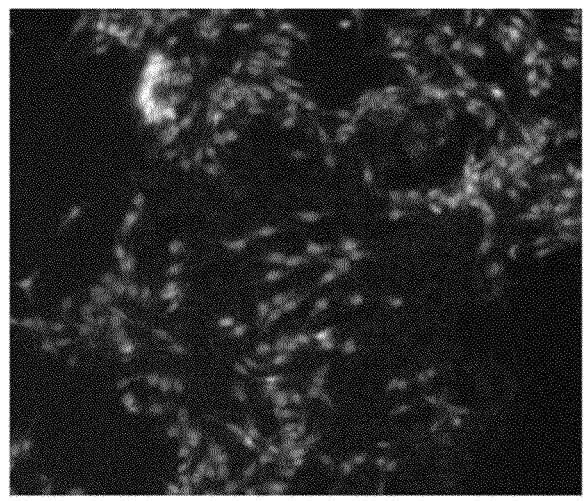
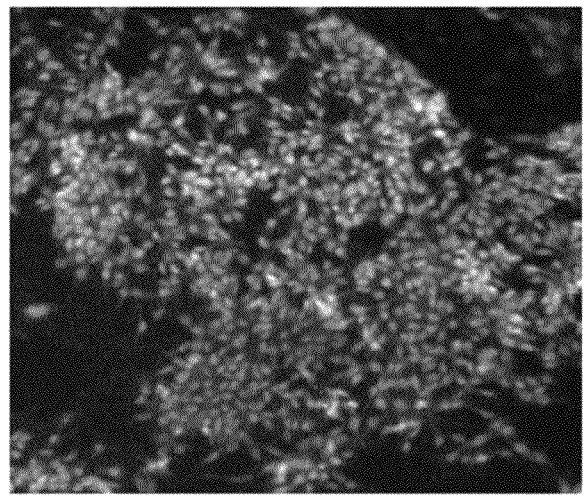
Figure 9

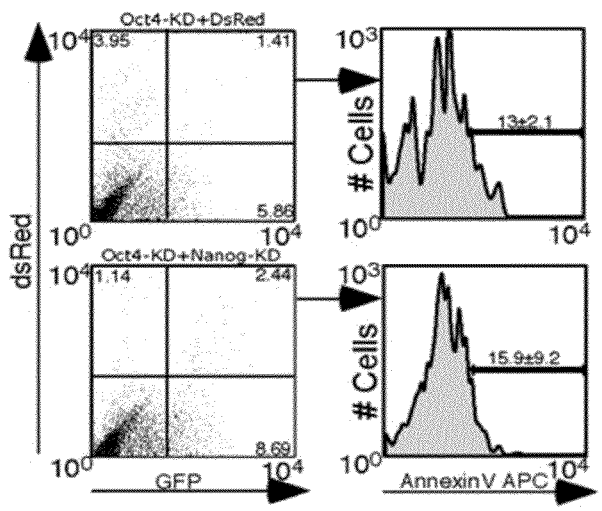
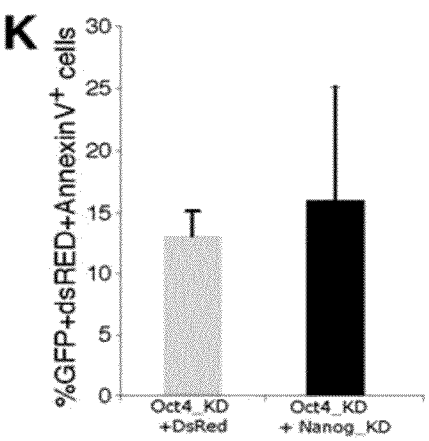
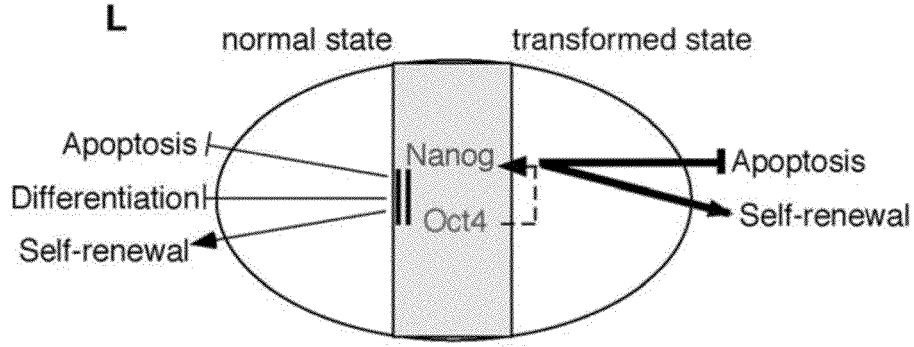
Figure 19 (Cont.)

| Cell line | Number of mice transplanted | Cell number injected | Number of mice developing teratomas | Tumor Volume (cm³) | Tumor weight (g) | Histology (H&E) | Tissues not detected | Metastasis present (Y/N) |
|---|---|---|---|---|---|---|---|---|
| hESC p56 | 2 | 60000 | 2/2 | 0.78 | 0.68 | 3 germ layers | Mesoderm (bone) | N |
| hESC p56 | 2 | 30000 | 2/2 | 2.80 | 1.37 | 3 germ layers | Mesoderm (bone) Endoderm (gut-like glands) | N |
| hESC p50 | 2 | 17500 | 1/2 | 0.001 | N/A | 1 germ layer or no tumor | Mesoderm (all tissues) Endoderm (all) | N |
| hESC p50 | 2 | 8750 | 0/2 | — | — | normal testes | all | N |
| hESC p50 | 3 | 4380 | 0/3 | — | — | normal testes | all | N |
| hESC p50 | 3 | 2190 | 0/3 | — | — | normal testes | all | N |
| hESC p50 | 3 | 1100 | 0/3 | — | — | normal testes | all | N |

| Cell line | Number of mice transplanted | Cell number injected | Number of mice developing teratomas | Tumor Volume (cm³) | Tumor weight (g) | Histology (H&E) | Tissues not detected | Metastasis present (Y/N) |
|---|---|---|---|---|---|---|---|---|
| v-hESC-1 p50 | 3 | 66000 | 3/3 | 2.62 | 1.31 | 3 germ layers | Mesoderm (mature muscle) | N |
| v-hESC-1 p50 | 2 | 24000 | 2/2 | 1.81 | 0.99 | 3 germ layers | Mesoderm (mature muscle) Endoderm (gut-like glands) | N |
| v-hESC-1 p50 | 3 | 7500 | 3/3 | 0.94 | 0.46 | 3 germ layers | Mesoderm (mature muscle) | N |
| v-hESC-1 p83 | 2 | 4100 | 2/2 | 0.552 | N/A | 3 germ layers | Mesoderm (bone) Endoderm (gut-like glands) | N |
| v-hESC-1 p50 | 2 | 800 | 1/2 | 0.30 | 0.18 | 2 germ layers | Mesoderm (all tissues) Endoderm (gut-like glands) | N |

Figure 26

| Cell line | Number of mice transplanted | Cell number injected | Number of mice developing teratomas | Tumor Volume (cm³) | Tumor weight (g) | Histology (H&E) | Tissues not detected | Metastasis present (Y/N) |
|---|---|---|---|---|---|---|---|---|
| v-hESC-2 | 3 | 46000 | 3/3 | 0.32 | N/A | 3 and 0 germ layers | Endoderm (gut-like glands) | N |
| v-hESC 2 | 3 | 12750 | 3/3 | 0.25 | N/A | 2 germ layers | Mesoderm (all tissues) Endoderm (gut-llike glands) | N |
| v-hESC 2 | 3 | 2000 | 3/3 | 0.658 | N/A | 3,1, or no germ layers | Mesoderm (bone) Endoderm (gut-like glands) | N |

Figure 27

TRANSFORMED HUMAN PLURIPOTENT STEM CELLS AND ASSOCIATED METHODS

RELATED APPLICATIONS

This application is a continuation of U.S. patent application Ser. No. 13/393,475 that was filed on Jun. 14, 2012, and claims priority to U.S. Provisional Application No. 61/238,806 that was filed on Sep. 1, 2009 and U.S. Provisional Application No. 61/238,822 that was filed on Sep. 1, 2009, which are incorporated herein by reference in their entirety.

FIELD OF THE DISCLOSURE

The disclosure relates to stem cells and in particular transformed human pluripotent stem cells (t-hPSCs), processes for identifying these cells as well as their use in cell-based screening assays.

BACKGROUND OF THE DISCLOSURE

Human stem cells add a tremendous power to cell-based drug discovery assays. This potential stems from their unique properties that include self-renewal and differentiation potential. Efforts related to drug discovery that use stem cell have been mainly focused on two areas: 1) toxicology studies and 2) discovery of new drugs and targets for tissue regeneration and cancer treatment.

Despite their potential and the current research efforts, stem cells are underutilized in this field due to the inexistence of stable stem cell lines capable of growing indefinitely and showing a reproducible behavior in culture. Furthermore, normal human primary stem cells are niche dependent and cannot be passaged as single cells, which consequently disables robotic seeding/passaging of cells and large-scale cell culture preventing their use in high-throughput screening assays. Accordingly, there is a need for novel stem cells and associated assays that meet the needs of high throughput assays.

In addition, cancer and normal stem cells (SCs) share proliferative properties of self-renewal and expression of key transcription factors (TFs). Despite similar TF identities, the functional role of specific TFs responsible for retaining SC state has not be carefully examined in cancer. There is also a need for new models for the study of cancer stem cells as well as methods and assays for selectively targeting cancer stem cells without damaging normal stem cells.

SUMMARY OF THE DISCLOSURE

The present inventors have identified and characterized transformed human pluripotent stem cells (t-hPSCs) derived from embryonic stem cell lines. These t-hPSCs carry minor genetic abnormalities, display increased growth rates and niche independence while retaining the key characteristics of non-transformed stem cells (i.e. self renewal capacity and pluripotency). The t-hPSCs disclosed herein are capable of being passaged as single cells making them ideal candidates for automated cell culture and high throughput screening (HTS). In addition, t-hPSCs have neoplastic features and display lower differentiation potential in vitro. In particular, t-hPSCs exhibit significantly reduced neural differentiation and are devoid of hematopoietic potential. Refractory differentiation is advantageous because these cells can be utilized to identify potent inducers of either neural or hematopoietic differentiation.

t-hPSCs exhibit a number of properties which distinguish them from other types of stem cells. In contrast to normal human pluripotent stem cells, t-hPSCs are not dependent on bFGF for maintenance of an undifferentiated state and self-renewal. Some t-hPSCs cells also co-express FGFR1 and IGF1R unlike human embryonic stem cells which only express IGF1R.

The applicants also compared the role of Oct4 and Nanog, two-core pluripotent transcription factors (TFs) that correlate with aggressive adult tumors, in transformed (t-hPSCs), and normal human pluripotent stem cells (hPSCs). Unlike normal stem cells, self-renewal and survival of t-hPSCs were found to be independent of Oct4. In contrast, t-hPSCs exhibit hypersensitivity to reduction in Nanog and demonstrate complete loss of self-renewal coupled with apoptosis in response to inhibition of Nanog. Dual and sequential knockdown of Oct4 and Nanog revealed that sensitivity of t-hPSCs to Nanog was Oct4 dependent. The t-hPSCs disclosed herein may therefore be used in assays and to identity therapeutic compounds for the selective destruction of aggressive tumors harboring cancer stem cells (CSCs) with similar molecular signatures.

Accordingly, in one aspect of the disclosure there is provided one or more isolated transformed human pluripotent stem cells (t-hPSCs). In one embodiment, the t-hPSC co-expresses FGFR1 and IGFR1. In another embodiment, the cells not require bFGF for maintenance of an undifferentiated state. For example, in some embodiments the t-hPSCs maintain expression of SSEA3 in the absence of bFGF. In one embodiment, the self-renewal and survival of the t-hPSCs is independent of Oct4. The t-hPSCs are also sensitive to levels of the transcription factor Nanog and require Nanog for self-renewal and cell survival. In some embodiments the t-hPSCs exhibit reduced neuronal differentiation and reduced hematopoietic potential in vitro compared to a normal human pluripotent stem cell. In one embodiment, the neural precursors derived from t-hPSCs do not form metastasis in vivo. Another aspect of the disclosure includes transformed induced pluripotent stem cells. In one embodiment, there is provide a cell-culture or cell lines comprising t-hPSCs as described herein.

In one aspect of the disclosure, the t-hPSCs are niche independent. In some embodiments, a surrounding fibroblast-like support layer present in cultures of normal embryonic stem cells is not present in cultures of t-hPSCs. In a further embodiment, t-hPSCs exhibit a higher teratoma initiating cell capacity in vivo relative to normal embryonic stem cells.

In another aspect of the disclosure, the t-hPSCs can be grown in tissue culture and passaged as a single cell. In one embodiment, t-hPSCs grow in monolayers without cell overlap. In one embodiment, t-hPSCs are homogenous with a consistent growth pattern which facilitates the image analysis of the cells. In some embodiments, cultures of t-hPSCs are niche independent and retain characteristics of self-renewal and pluripotency.

In one aspect, there is provided a method of screening a compound for a biological activity with the t-hPSCs described herein. In one embodiment, the method comprises contacting one or more t-hPSCs with a compound and detecting an effect of the compound on the t-hPSCs. Optionally, the biological activity is cell differentiation activity or loss of pluripotency. In one embodiment, the biological activity is anticancer activity. In one embodiment, the biological activity is cell death or an inhibition in cell growth.

In one embodiment, the effect of the compound on the one or more cells is indicative of the biological activity of the compound. For example, in one embodiment the biological activity is cell differentiation activity or loss of pluripotency and the method comprises detecting the emergence of progenitor or precursor cells that are refractory to differentiation. In one embodiment, the biological activity is anticancer activity and the method comprises detecting cell differentiation, loss of pluripotency, cell proliferation, cell number, DNA content, cytotoxicity, or apoptosis. Optionally, compounds that promote t-hPSC differentiation, loss of pluripotency, cytotoxicity or apoptosis are identified as having anticancer activity. Optionally, compounds that inhibit growth of t-hPSC, decrease the number of t-hPSC or DNA content are identified as having anticancer activity.

In another aspect, the methods described herein can be used to identify compounds that have a different biological activity or exhibit a different level of biological activity for t-hPSCs compared to other types of cells such as normal stem cells. Optionally, the normal stem cells are pluripotent stem cells or induced pluripotent stem cells. In one embodiment, the method further comprises comparing the effect of a compound on one or more t-hPSCs to an effect of the compound on one or more normal stem cells. Optionally, the method comprises comparing the effect of a compound on one or more t-hPSCs with a predetermined value or result. In one embodiment, the effect of the compound on one or more normal stem cells is experimentally determined by contacting one or more stem cells with the compound and detecting an effect of the compound on the one or more SCs, wherein the effect is indicative of the biological activity of the compound.

In one embodiment, the step of detecting an effect of a compound on the t-hPSCs or SCs comprises detecting the presence or absence of a biomarker. In one embodiment, the step of detecting an effect of a compound on the t-hPSCs or SCs comprises detecting the relative or absolute amount of a biomarker. As used herein, "biomarker" refers to a characteristic that can be objectively measured that indicates the normal or pathogenic biological processes or pharmacological response of one or more cells. For example in one embodiment, the biomarkers are molecules, genes or proteins known in the art to be associated with a biological activity such as loss of pluripotency, cell proliferation, apoptosis, cytotoxicity or differentiation. In one embodiment, the biomarkers are detected using immunodetection with antibodies. In one embodiment, the step of detecting an effect of a compound comprises detecting the expression of one or more biomarkers. In one embodiment, the biomarkers are fluorescently labeled. In one embodiment, the expression of a biomarker is operably linked to a reporter gene. In one embodiment, the t-hPSCs are transfected with a vector comprising a biomarker promoter operably linked to a promoter gene.

In one embodiment, the biomarker is a pluripotency biomarker selected from Oct4, Sox2, Nanog, SSEA3, SSEA4, TRA-1-60, TRA-1-81, IGF1 receptor, connexin 43, E-cadherin, Alkaline phosphatase, REX1, CRIPTO, CD24, CD90, CD29, CD9 and CD49f. In one embodiment, expression of a pluripotency marker in a t-hPSC of SC is operably linked to a reporter gene and detecting a decrease in the expression of the reporter gene indicates a loss of pluripotency in response to the compound.

In one embodiment, the biomarker is an apoptosis biomarker selected from activated caspases 2, 3, 7, 8 and 9, Cytochrome c, Externalised phosphatidylserine, Cytokeratins, Nucleosomal DNA, Apo-1/Fas, Fas ligand (sFasL), Bcl-2/Bcl-xl/Mcl-1, p53, phospo-p53, p21wafi, pH2AX (see for example Ward et al. Biomarkers of apoptosis, British Journal of Cancer (2008) 99, 841-846.)

In one embodiment, the biomarker is a molecular marker linked to one of the following signaling pathways: Wnt, hedgehog, TGF beta, fibroblast growth factor, notch, Insulin-like growth factor, FMS-like tyrosine kinase 3 and retinoic acid. In one embodiment, the biomarker is a marker indicative of cell proliferation, cell cycle, cell death, or cell adhesion.

In another aspect, the present application provides methods for subculturing stem cells to provide cells with predictable growth suitable for use in screening assays and in particular for high throughput screening assays. In one embodiment, the subcultures of cells are subcultures of normal pluripotent stem cells or induced pluripotent stem cells. In one embodiment, a subculture of undifferentiated stem cells is created by:

i) isolating a cell cluster comprising undifferentiated stem cells from a single colony;

ii) transferring the cell cluster to a well or receptacle, wherein the cells of the cluster are plated in a predetermined location in the well or receptacle; and iii) culturing the cells to produce the subculture of undifferentiated stem cells.

In one embodiment, the isolation of a cell cluster from the single colony comprises mechanically punching colonies with a fine sharp instrument. Optionally, the fine sharp instrument is a fine point pipette tip. In one embodiment, the isolation of a cell cluster from the single colony comprises scoring the colonies with a sharp instrument and removing the cluster by repeated pipetting. In some embodiments, the cells are subjected to fluorescence-based selection prior to being transferred to a predetermined location in a well or receptacle. Optionally, the fluorescence-based selection comprises large particle cell sorting. In one embodiment, the cell cluster is transferred to a location furthest away from the borders of the well. In one embodiment, the cell cluster is transferred to a location that comprises the centre of the well. Optionally, the well comprises an adhesive layer patterned onto a non-adhesive surface at the predetermined location. In one embodiment, the adhesive layer comprises matrigel. In another embodiment, the non-adhesive surface comprises repellent plastic or low adhesion plates. In one embodiment, the non-adhesive surface is created by treating plates with an agent that converts the polarity of the tissue culture surface, such as a Pluronic co-polymers. In one embodiment, the method comprises isolating cell clusters from an area of the colony that does not contain differentiated cells. Optionally, the area comprises the inner ⅔ area of the colony or preferably the inner ⅓ area of the colony. Also provided herein are uses of the subculture of undifferentiated stem cells for high throughput screening analysis. Also provided are screening methods that utilize subcultures of one or more cells created by the methods of the present application. In one embodiment, subcultures of normal stem cells created by the methods as described herein as used in comparative screening assays along with t-hPSCs.

In another aspect, bulk culture seeding methods are used to subculture normal stem cells used in the comparative screening assays described herein. In one embodiment, the normal stem cells are repeatedly triturated before plating. In one embodiment, a subculture of undifferentiated stem cells is created by dissociating a colony of stem cells with collagenase, repeatedly triturating the cells in a cell suspension, diluting the cells in the suspension to approximately 10,000 cells per 50 µl, and optionally passing the suspension through a 100 µm strainer.

A further aspect of the invention includes methods of identifying the t-hPSCs or t-iPSCs described herein. For example, in one embodiment there is provided a method of identifying transformed pluripotent stem cells or transformed induced pluripotent stem cells comprising identifying stem cells that maintain expression of SSEA-3 when deprived of bFGF. In some embodiments, FACS is used to identify and isolate the t-hPSCs. In one embodiment, there is provided a method of identifying transformed pluripotent stem cells comprising inhibiting Oct4 expression in a population of pluripotent stem cells, and identifying undifferentiated cells that maintain expression of SSEA3.

In some embodiments, t-hPSCs exhibit different patterns of gene expression relative to other cells such as normal embryonic stem cells or EP2102 cells. Accordingly, the present disclosure includes methods of identifying t-hPSCs based on gene expression. The present disclosure also includes methods of identifying t-hPSCs based on mitotic index and cell growth properties, t-hPSCs morphology, SSEA3 expression levels, and/or the presence of genetic abnormalities such as amplifications or deletions.

The t-hPSCs described herein may also be used in cell-based assays. One embodiment includes a method of culturing cells for use in a cell-based screening assay comprising placing one or more transformed human pluripotent stem cells into a receptacle and culturing said stem cells in the receptacle to form a monolayer of stem cells. In one embodiment, the cells in the monolayer do not fully overlap such that adjacent cells can be individually distinguished. In some embodiments, a single cell is placed into a receptacle and the culturing said stem cell results in a homogeneous clonal colony of the single cell.

In one aspect, there is provided a method for screening a compound for its ability to cause a loss of pluripotency. In one embodiment, the method comprises contacting the compound with a transformed human pluripotent stem cell wherein expression of a pluripotency marker in the t-hPSCs is operably linked to a reporter gene and measuring the expression of the reporter gene in response to the compound. In one embodiment, the reporter gene is green fluorescent protein and the t-hPSCs contain a vector wherein a promoter of a pluripotency marker is operably linked to a reporter gene. In one embodiment, the pluripotency marker is Oct4.

In another aspect, there is provided uses and methods for screening compounds for activity in differentiating cells to different cell types. In one embodiment, methods and uses of screening compounds for activity in differentiating t-hPSCs into hematopoietic or neural lineages are provided.

A further aspect of the disclosure includes the use of the t-hPSCs or t-iPSCs described herein as a model to study cancer stem cells. In one embodiment, the t-hPSCs are useful as an in vitro model for cancer stem cells. For example, in one embodiment there is provided an in vitro method for screening a compound for apoptotic activity comprising contacting the compound with a t-hPSCs and measuring the survival of the cells. In one embodiment, the activity of a compound against t-hPSCs is used to predict the anti-cancer activity of the compound.

Also provided are methods for targeting cancer stem cells for apoptosis comprising inhibiting, reducing or interfering with the expression or activity of the transcription factor Nanog. For example, in one embodiment there is provided a method of screening a compound for use as chemotherapeutic agent comprising contacting the compound with t-hPSCs and determining whether the compound inhibits Nanog activity by monitoring for the loss of self-renewal and apoptosis of the transformed t-hPSCs.

Also provided are compositions comprising microtitre plates with a plurality of receptacles wherein one or more of the receptacles contain t-hPSCs or t-iPSCs as described herein. In one embodiment, the microtitre plates are high-throughput format microtitre plates. In some embodiments, the plates have 2 or more, 24, 48, 96, 384 or 1536 individual receptacles or wells and are suitable for use in high-throughput screening such as in automated systems and/or robotic systems.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

FIG. 9 shows transformed stem cells seeded as single cells and grown in culture using standard stem cell culture conditions for 4 days. At day 2 and 3 BMP4 was added to each of the treated wells at various concentrations. On day 4 microtiter plates containing treated transformed stem cells were imaged using the cellomics ArrayScan HCS reader (are shown in blue (Hoescht 33342). A) No BMP untreated control. B) Cells treated with BMP showing a significant loss of GFP expression.

FIGS. 10A-C shows that decreasing expression levels of GFP are identified upon treatment of cells with DMSO; GFP is shown in green while blue represents staining by the nuclear dye Hoescht. A, B and C depict GFP expression after treatment of cells for 4 consecutive days with 0%, 0.01% (similar results were found when cells were treated with 0.5% DMSO) and 2% (v/v) of DMSO respectively. D) Cell numbers were quantified based on the automated detection and segregation of cells labelled by the nuclear dye Hoescht. E) Cells were categorized as Oct4-GFP (pluripotency) positive or negative based on the combined expression of GFP and the identification of the nuclear marker Hoescht or sole labeling of nuclear DNA (Hoescht) respectively. The graph displays data obtained by automated image analysis. F) Cells were treated with Ethidium Homodimer (EtDH) which selective penetrates the membrane and labels dead cells red; automated image acquisition and analysis was performed. All images were analyzed using the Cellomics software.

FIG. 12 A. Basal apoptotic rates are significantly higher in the hESCs versus the v-hESCs, implying that v-hESCs have increased survival and anti-apoptotic capacities. Treatment with compound "X" (100 nM, 4 days) increased apoptosis significantly in both hESCs and v-hESCs, however apoptosis was higher in the v-hESCs versus treated hESCs. (**$p<0.001$; n=6) B. When dsRED-v-hESCs were co-cultured with GFP-hESCs at a 1:1 ratio, compound "X" treatment preferentially targeted the v-hESCs resulting in a 1:5 ratio of v-hESCs to hESCs in the culture as measured by FACS ($p<0.01$; n=3). C. Immunofluorescence imaging of the compound "X" treated flat co-cultures and embryoid bodies (EBs) further supports the FACS assay indicating that the inhibitor treatment maintains the skewed v-hESCs (red) to hESCs (green) ratio, which remains constant even during the hematopoietic differentiation program (hEB development). Thus, v-hESC being similar to cancer stem cells, given that they show niche independence, have increased anti-apoptotic signaling, enhanced proliferation and low differentiation capacity, are preferentially targeted by the drug versus the normal stem cells. D. Compound "X" treatment leads to the emergence of hematopoietic progenitors (CD45$^+$CD34$^+$) from v-hESCs that are otherwise refractory to differentiation, and in addition it also increases hematopoietic output in the normal hESCs (*$p<0.01$; **$p<0.001$; n=9). Hence, compound "X" normalizes the v-hESCs cells resulting in a hematopoietic differentiation profile similar to that observed for the hESCs.

FIG. 26 shows a limiting dilution assay for hESC and v-hESC-1 Teratoma Formation. Limiting dilution teratoma assay for undifferentiated hESC and v-hESC-1 cultures over 6 weeks. Teratomas from hESC and v-hESC-1 cultures were analyzed under the following parameters: number of mice developing teratomas, teratoma weight and volume, histology (germ layers present/absent), and presence of metastasis.

FIG. 27 shows a limiting dilution assay for hESC and v-hESC-2 teratoma formation. Limiting dilution teratoma assay for undifferentiated hESC and v-hESC-2 cultures over 6 weeks. Teratomas from hESC and v-hESC-2 cultures were analyzed under the following parameters: number of mice developing teratomas, teratoma volume, histology (germ layers present/absent), and presence of metastasis.

FIGS. 1D-E: Measurements of cell viability using trypan blue on human mobilized peripheral blood treated with mefloquine or thioridazine for 5 days. Mefloquine and thioridazine at various doses (0.1-10 µM) did not reduce cell viability relative to control samples (0 µM) indicating that these compounds are non-toxic to human cells.

DETAILED DESCRIPTION OF THE DISCLOSURE

The present inventors have identified and characterized transformed human pluripotent stem cells (t-hPSCs) derived from embryonic stem cell lines.

t-hPSCs exhibit a number of features that distinguish them from other cells including normal pluripotent stem cells. As used herein, "transformed human pluripotent stem cell (t-hPSC)" refers to a cell that is able to differentiate into more than one cell type and does not require Oct4 for self-renewal or survival. As used herein, the terms "transformed human pluripotent stem cell" (t-hPSC), "variant human embryonic stem cells (v-hESC-1)" and "variant human pluripotent stem cell" refer to the same type of cell. Variant human embryonic stem cell line v-hESC-1 was deposited, in accordance with the Budapest Treaty, with the International Depositary of Canada (IDAC), 1015 Arlington Street, Winnipeg, Manitoba Canada, R3E 3R2 on Jul. 22, 2015 under Accession No. 220715-01. In accordance with 37 CFR 1.808, the depositors assure that all restrictions imposed on the availability to the public of the deposited materials will be irrevocably removed upon the granting of a patent. The depositors additionally assure that the deposited materials will be replaced if viable samples cannot be dispensed by the depository.

In one aspect of the disclosure, t-hPSCs are readily distinguished from normal stem cells. The term "stem cell" as used herein refers to a cell that has the ability for self-renewal. An "undifferentiated stem cell" as used herein refers to a stem cell that has the ability to differentiate into a diverse range of cell types. The term "differentiation" as used herein refers to the process by which a less specialized cell, such as a stem cell, becomes a more specialized cell type, such that it is committed to a specific lineage. The term "pluripotent stem cell" as used herein refers to a stem cell that can give rise to cells of multiple cell types. The term "multipotent stem cell" as used herein refers to a stem cell that can give rise to many but limited types of cells. As used herein, "progenitor or precuror cell" refers to cell with a limited replicative capability that shows signs of differentiation towards a target cell. Culture conditions that maintain the stem cells in an undifferentiated state are readily known in the art. For example, Thompson JA et al., Science, 1998 Nov. 6; 282(5391):1145-7 outlines these conditions. As used herein, a "normal stem cell" is a stem cell that is not a "transformed" stem cell. As used herein "transformed" stem cells are cells that carry genetic modifications, reduced or compromised differentiation capacity and/or faster proliferation when compared to their normal embryonic stem cell counterparts. Transformed cells also show a differential response to signaling molecules such as bFGF.

Figure 3:
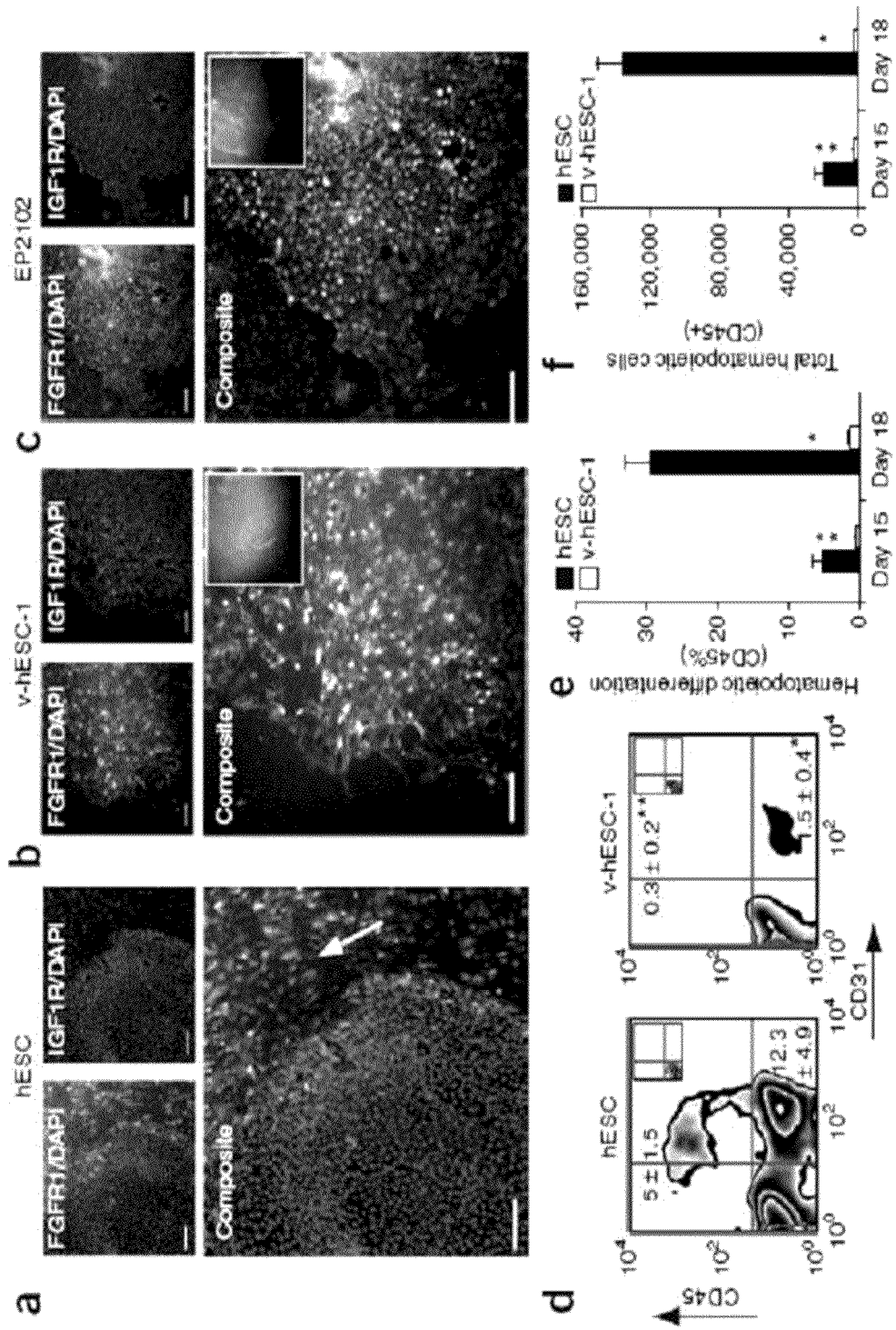
FIG. 3 shows v-hESC-1 cells have acquired FGFR1 and IGF1R expression on all pluripotent cells within the culture and are refractory to differentiation in vitro. (a-c) Immunocytochemical analysis of FGFR1 (green) and IGF1R (red) in hESC (a), v-hESC-1 (b) and EP2102 malignant teratocarcinoma (c) cells. Nuclei were stained with DAPI (blue). Arrow in a) depicts localization of FGFR1 exclusively to the fibroblast-like support cells in normal hES cell cultures. IGF1R was expressed only within the colonies of the normal hES cells. Note the contrasting staining pattern for both v-hESC-1 cells and EP2102 cells where FGFR1 and IGF1R co-localize. Insets: isotype control. Scale bars, 100 µm. (d) Flow cytometric analysis of the hematopoietic markers, CD31 and CD45, in hESC EBs and v-hESC-1 EBs after 15 d. (e) Quantification of hematopoietic differentiation (CD45%) in hESC and v-hESC-1 EBs over 15 and 18 d. Error bars, s.e.m. *, $P<0.05$, **, $P<0.01$. (f) Quantification of total CD45+ cells and total cell number in hESC and v-hESC-1 EBs over 15 and 18 d. Error bars, s.e.m. *, $P<0.05$, **, $P<0.01$. (g) Brightfield (upper panels) and A2B5 immunocytochemical (lower panels) analysis of hESC and v-hESC-1 EBs on poly-L-lysine/fibronectin-coated plates in neural proliferation medium after 8 d. Arrow in upper panel indicates primitive neural rosette-like features in v-hESC-1 cultures. Arrows in lower panels indicate long extensions in neuronal-like neural precursor cells. Insets: isotype control, nuclei stained with DAPI. Scale bar, 100 µm. (h) Frequency of A2B5 expression in hESC and v-hESC-1 EBs in neural culture. Error bars, s.e.m. *, $P<0.05$. (i) Representative quantification of total A2B5+ cells and total cells in hESC and v-hESC-1 EBs. Error bars, s.e.m. *, $P<0.05$, ***, $P<0.001$. (j,k) Quantification of SSEA3 (j) and Oct4 (k) in hESC EBs and v-hESC-1 EBs cultured in hematopoiesis-inducing conditions over 15 d. Error bars, s.e.m. *, $P<0.05$, **, $P<0.01$. Line graphs represent normalization of SSEA3 (b) and Oct4 (c) in hESC (solid line) and v-hESC-1 EBs (dashed line) relative to undifferentiated controls.
Figure 3:
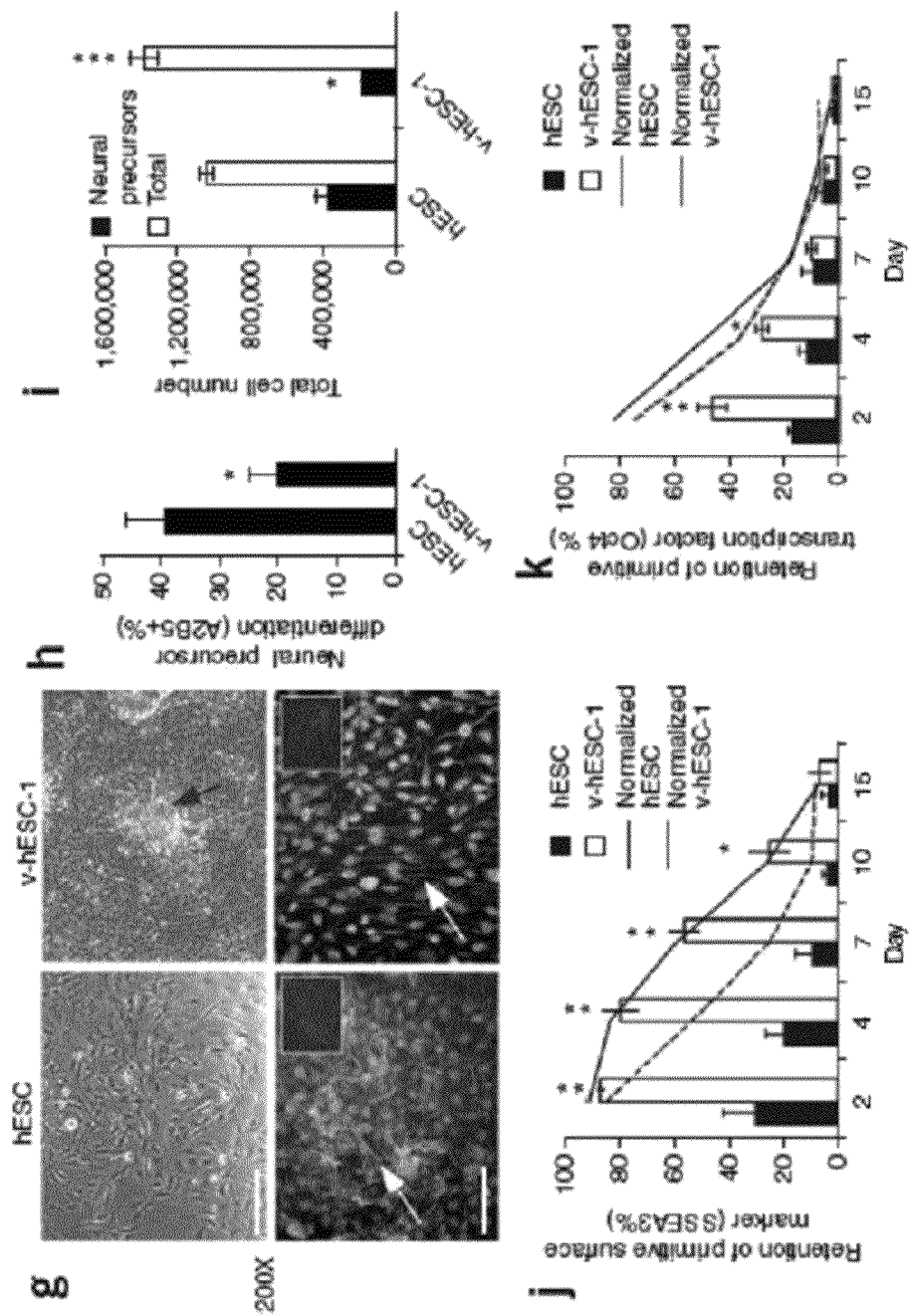

As shown in FIGS. 3A-C and Example 1, in one embodiment t-hPSCs express both fibroblast growth factor receptor (FGFR)1 and insulin-like growth factor 1 receptor (IGF1R). In contrast, normal human embryonic stem cells (hESs) express IGF1R, while FGFR1 is expressed exclusively in fibroblast-like cells also found in human embryonic stem cell cultures.

In another embodiment, the t-hPSCs described herein do not require basic fibroblast growth factor (bFGF) in culture for maintenance of an undifferentiated state. As used herein an "undifferentiated state" refers to a cell that is pluripotent or is still able to differentiate into more than one cell type. As shown in Example 1 and FIG. 2B-C, as bFGF was titrated out of cultures containing either normal or t-hPSCs, normal cells lost expression of the pluripotency marker SSEA3 while t-hPSCs did not. In one embodiment, the t-hPSCs described herein maintain expression of SSEA3 in the absence of bFGF.

In another aspect, t-hPSCs described herein do not require Oct4 for self-renewal or survival. In yet another aspect, t-hPSCs require Nanog for self-renewal and survival. The applicants investigated the roles of the transcription factors Oct4 and Nanog in both normal hPSCs and t-hPSCs. In normal hPSCs, the self-renewal and survival of the cells is dependent on Oct4. In contrast and as shown in Example 4, t-hPSCs do not require Oct4. Rather, t-hPSCs exhibit hypersensitivity to a reduction in Nanog levels and demonstrate loss of the ability to self-renew coupled with apoptosis.

In addition, the t-hPSCs described herein exhibit a different pattern of differentiation compared to normal hPSCs. In one embodiment, the t-hPSCs exhibit reduced hematopoietic potential in vitro compared to normal hPSCs. As shown in Example 1 and FIG. 3D-F, after 15 days in hematopoietic culture expression of CD45 in t-hPSCs erythroid bodies was greater than 15 fold less than that for normal hPSCs.

One embodiment described herein includes a cell culture or cell line comprising a plurality of t-hPSCs. As used herein the term "cell culture" refers to one or more cells grown under controlled conditions and optionally includes a cell line. The term "cell line" refers to a plurality of cells that are the product of a single group of parent cells. Controlled conditions include the use of media such as Matrigel (BD Biosciences) and may also include specific growth factors or additional substances or nutrients. For example, as shown in Example 1 and FIG. 1, t-hPSCs grown in cell culture typically show a lack of well-defined colony edges and the loss of surrounding fibroblast-like cells that normally appear in non-transformed human embryonic stem cells.

Figure 5:
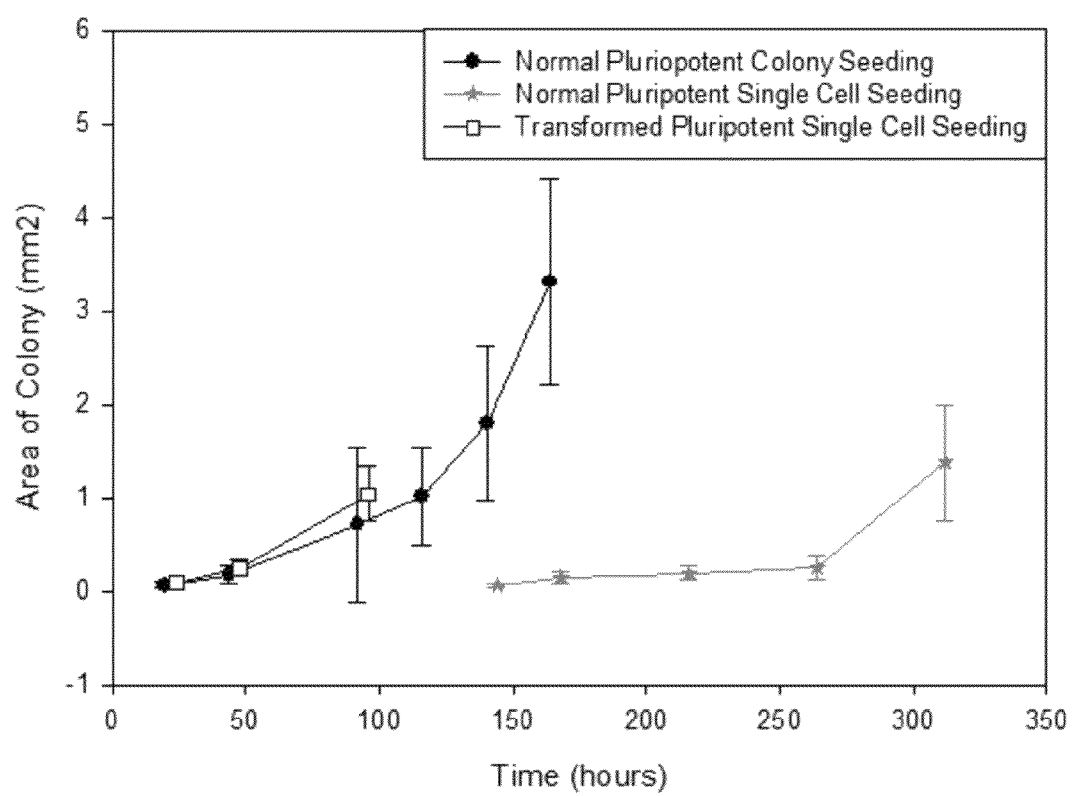
FIG. 5 shows the kinetics of pluripotent stem cell colony growth measured by the colony area. Normal pluripotent stem cells were seeded as clusters or single cells. Note that with cluster seeding colonies are detected 24 h after seeding and continue to increase during the culture period. In contrast, colonies from single cell seeded wells are only detected at 144 h and have delayed colony growth until after 264 h. Colonies from transformed cells seeded as single cells follow the same recovery pattern as normal cells seeded as clusters.

In one embodiment, the t-hPSCs cultures described herein can be passaged as a single cell. As used herein, "passaged as single cells" refers to individually isolating and transferring a single cell to a culture vessel wherein the cell is then capable of forming a plurality of cells. Example 2 and FIG. 5 show that colonies generated from seeding a single transformed-human pluripotent stem cell show growth rates comparable to non-transformed stem cells plated as clusters of cells and growth rates that are much faster than seeding a single normal pluripotent stem cell.

Figure 6:
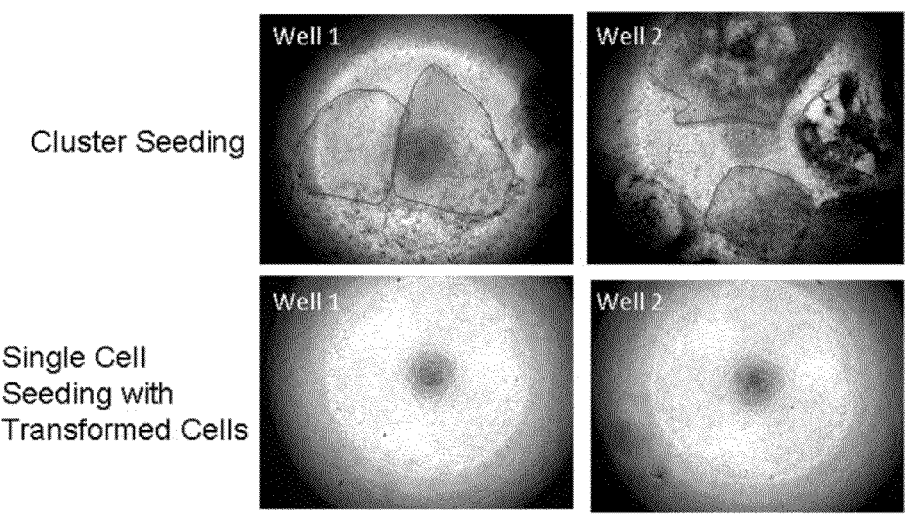
FIG. 6 shows cluster seeding of normal stem cells versus single cell seeding of transformed stem cells. Note the inter-well variation in colony shape, location and numbers in cluster seeded wells (outlined in top two panels) compared to the homogeneous cell monolayer that develops with transformed stem cells (lower two panels).

The use of normal stem cells in high-throughput screening assays has been hampered by the fact that stem cell cultures are typically unstable and exhibit significant variability, such as in the appearance of cells in wells in microtitre plates. In one embodiment, the t-hPSCs described herein are able to be seeded as single cells in microtitre plates and following incubation exhibit consistent colony shape, location and numbers as shown in FIG. 6. In one embodiment, the t-hPSCs described herein are useful for screening the activity of differentiation agents that would otherwise be tested using normal cells, which is very laborious and often not amendable to medium or high throughput assays.

In another embodiment, cell cultures comprising t-hPSCs grow in monolayers without cell overlap. As used herein, the term "monolayer" refers to a plurality of adjacent cells forming a surface that generally has a thickness of only one cell. As used herein, the term "without cell overlap" refers to a plurality of cells wherein adjacent cells may partially overlap but can be individually distinguished. As shown in Example 2 and FIG. 10, the t-hPSCs described herein enable cell growth in monolayers with limited cell overlap facilitating the image analysis of t-hPSC cell cultures such as in High Throughput Screening or High Content Screening.

Figure 14:
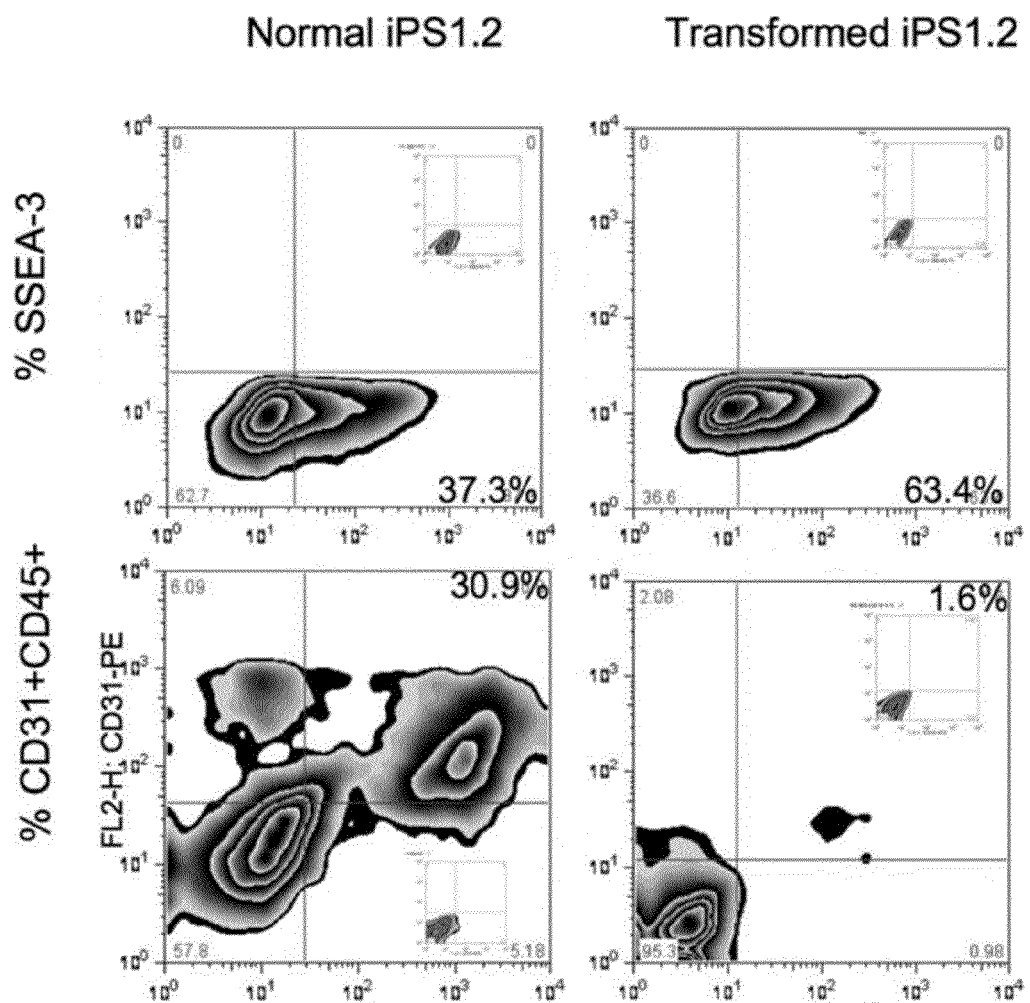
FIG. 14 shows FACS analysis for SSEA-3 (top panels) and CD31+CD45+(bottom panels) in normal and transformed iPS1.2 cells.
Figure 15:
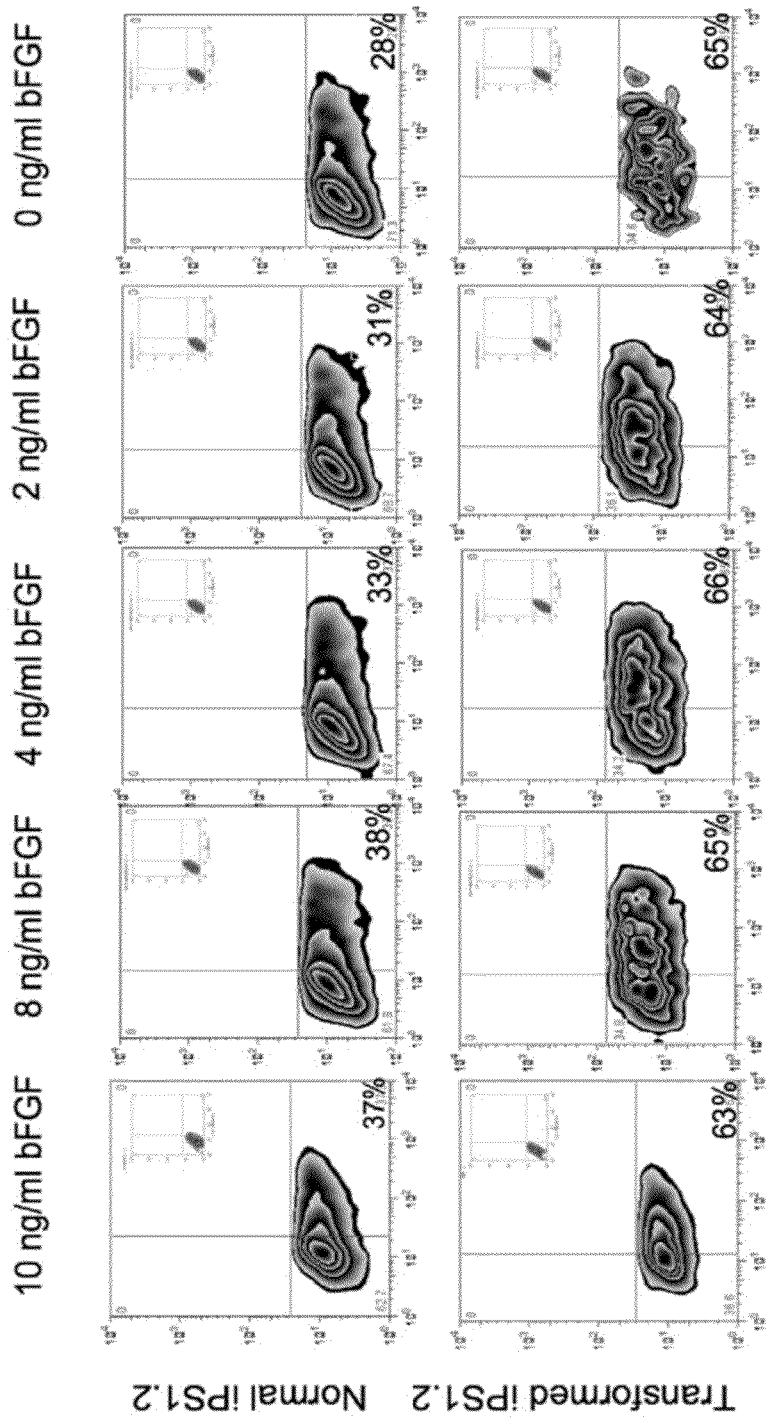
FIG. 15 shows FACS analysis for SSEA-3 in diminishing concentrations of bFGF in normal and transformed iPS1.2 cell lines. Upon depleting concentrations of bFGF (10, 8, 4, 2, and 0 ng/mL) normal iPSCs show a synchronized decrease in frequency of SSEA-3 (37% to 28%, upper panel), indicating loss of the undifferentiated state whereas the transformed iPSCs maintain an SSEA-3 frequency of over 60% (lower panel).

A further aspect of the disclosure includes transformed induced pluripotent stem cells. As used herein, an "induced pluripotent stem cell" refers to a pluripotent stem cell artificially derived from a non-pluripotent cell. Typically, induced pluripotent stem cells are produced by altering the expression of certain genes in a somatic cell. As shown in Example 3, the applicants have produced transformed induced pluripotent stem cells (t-iPSCs) derived from normal induced pluripotent stem cells created after skin fibroblast genetic reprogramming. In some embodiments, the transformed-induced pluripotent stem cells (t-iPSCs) exhibit morphology traits similar to the t-hPSCs described herein including a distinct morphology (FIG. 13) as well as increased expression of SSEA3 (FIG. 14) and lack of dependence on bFGF for maintaining the cells in a undifferentiated state (FIG. 15). A person of skill in the art will appreciate that t-iPSCs may sometimes be used in place of t-hPSCs in the screening methods as described herein.

In another aspect of the disclosure there is provided methods for identifying t-hPSCs or t-iPSCs. In one embodiment, a method is provided wherein cells that maintain expression of SSEA-3 when deprived of bFGF are identified as t-hPSCs. As shown in Example 1 and 2, normal stem cells require bFGF in order to maintain undifferentiated which is associated with the expression of the pluripotency marker SSEA-3. Accordingly, in one embodiment there is provided a method of identifying transformed pluripotent stem cells comprising: culturing pluripotent stem cells with bFGF; analyzing the cells for SSEA-3 to provide a first level of expression; depleting the cell culture of bFGF; analyzing the cells for SSEA-3 to provide at least a second level of expression; identifying those cells that maintain expression of SSEA-3 upon depletion of bFGF by comparing the first and at least second levels of SSEA-3 expression. In one embodiment, the levels of SSEA-3 are determined using fluorescent activated cell sorting (FACS). A person skilled in the art will appreciate additional methods for analyzing the expression levels of SSEA3 such as PCR base methods or immunolabelling with SSEA-3 antibodies.

The t-hPSCs described herein are distinct from normal PSCs in that they do not require Oct4 in order to be maintained in an undifferentiated state (See Example 4). As previously noted, SSEA-3 expression provides marker of cell pluripotency. Accordingly in one embodiment there is provided a method of identifying transformed pluripotent stem cells comprising inhibiting Oct4 expression in a starting population of pluripotent stem cells and identifying stem cells that stay in an undifferentiated state. In one embodiment, expression of SSEA-3 is used to identify cells that have been maintained in an undifferentiated state following inhibition of Oct4. Various methods may be used to inhibit Oct4 expression. For example, in one embodiment shRNA transduction of Oct4 is used to inhibit Oct4 expression.

In a further aspect, a person skilled in the art will appreciate that the characteristics of the t-hPSCs described herein can be used in methods to identify t-hPSCs. For example, in some embodiments, the t-hPSCs exhibit different patterns of gene expression relative to other cells such as normal embryonic stem cells or EP2102 cells. Accordingly, the present disclosure includes methods of identifying t-hPSCs based on gene expression. Additional methods of identifying t-hPSCs include those based on mitotic index and cell growth properties, t-hPSCs morphology, SSEA3 expression levels, and/or the presence of genetic abnormalities such as amplifications or deletions as set out in Example 1.

In one aspect of the disclosure, there is provided screening assays that use the t-hPSCs described herein. In one embodiment, the screening assays are high throughput screening assays. The term "high throughput screening" as used herein refers to automated in vitro testing of the effect of compounds or conditions on cells and such screening is typically performed with the aid of computer or robot-controlled processes. As used herein, the term "compound" includes, without limitation, chemicals, pharmacological agents, small organic molecules, biomolecules, polypeptides, proteins, antibodies, sugars, polysaccharides, polynucleotides, cells, or combinations thereof. Such a compound may be a naturally-occurring product or a synthetic product.

In one embodiment, the cells and methods described herein are useful for screening a compound for a biological activity. As used herein the phrase "screening a compound for a biological activity" refers to identifying or testing a compound with respect to its physiological or pharmacological effects on the normal or abnormal biochemical function of one or more cells. As used herein the phrase "biological activity" includes but is not limited to cell toxicity (cytotoxicity), apoptosis, cell death, signal transduction, cell signaling, cell differentiation, loss of pluripotency, cell growth, or anticancer activity.

In one embodiment, the biological activity is anticancer activity. As used herein, "anticancer activity" refers to the effect of a compound on a cell that has reduced or compromised differentiation capacity and/or faster proliferation when compared to a corresponding normal cell that results in the death of the cell or inhibits the growth of the cell. In one embodiment, anticancer activity comprises differentiation activity and/or loss of pluripotency. For example, in one embodiment a compound with anticancer activity results in the death or inhibits the growth of transformed cells such as t-hPSCs compared to normal stem cells. Transformed stem cells carry genetic modifications, reduced or compromised differentiation capacity and/or faster proliferation when compared to their normal embryonic stem cell counterparts.

In one aspect, the methods described herein comprise screening a compound for biological activity by detecting an effect of the compound on one or more cells. In one embodiment, the effect is indicative of biological activity of the compound. In one embodiment, "detecting an effect" comprises monitoring or determining cell size or morphology, expression of cell markers, the emergence of cell types or the biochemical make-up of the cell. For example, in one embodiment "detecting an effect" includes, but is not limited to, using methods such as immunohistochemistry (IHC), ELISA, reporter genes, PCR or RT-PCR, fluorescent lables, cytometric bead arrays, DNA arrays, flow cytometry or optical analysis to detect the effect of a compound on t-hPSCs cells or normal stem cells.

Figure 28:
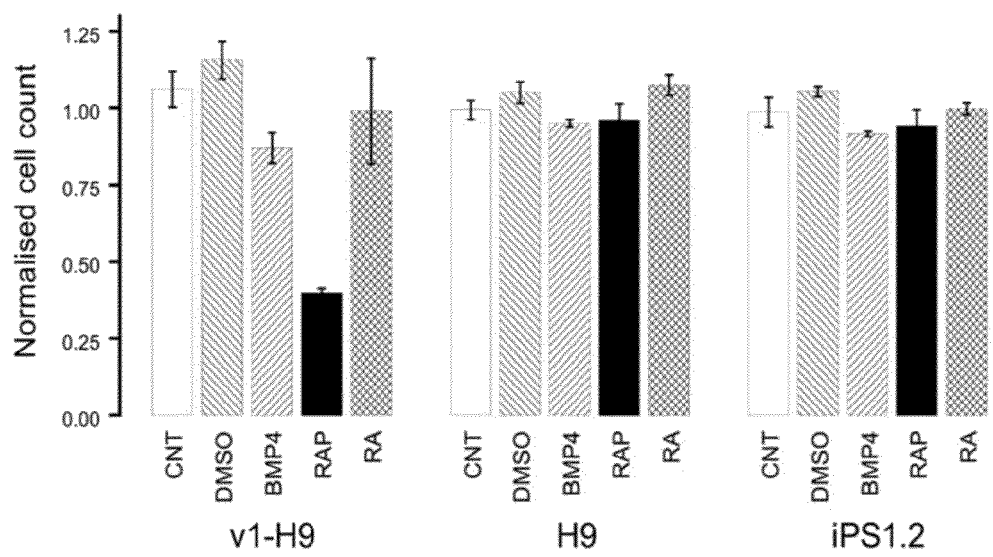
FIG. 28 shows the normalized cell count for t-hPSCs (V1-H9), H9 cells (hPSCs) and iPS1.2 cells 96 hours after treatment with 0.1% DMSO, BMP4, RAP (Rapamycin) or RA (Retinoic Acid) (data shown±s.e.m.) RAP is shown to differentially interact with and reduce the number of t-hPSCs compared to hPSCs (H9) or iPS1.2 cells.
Figure 29:
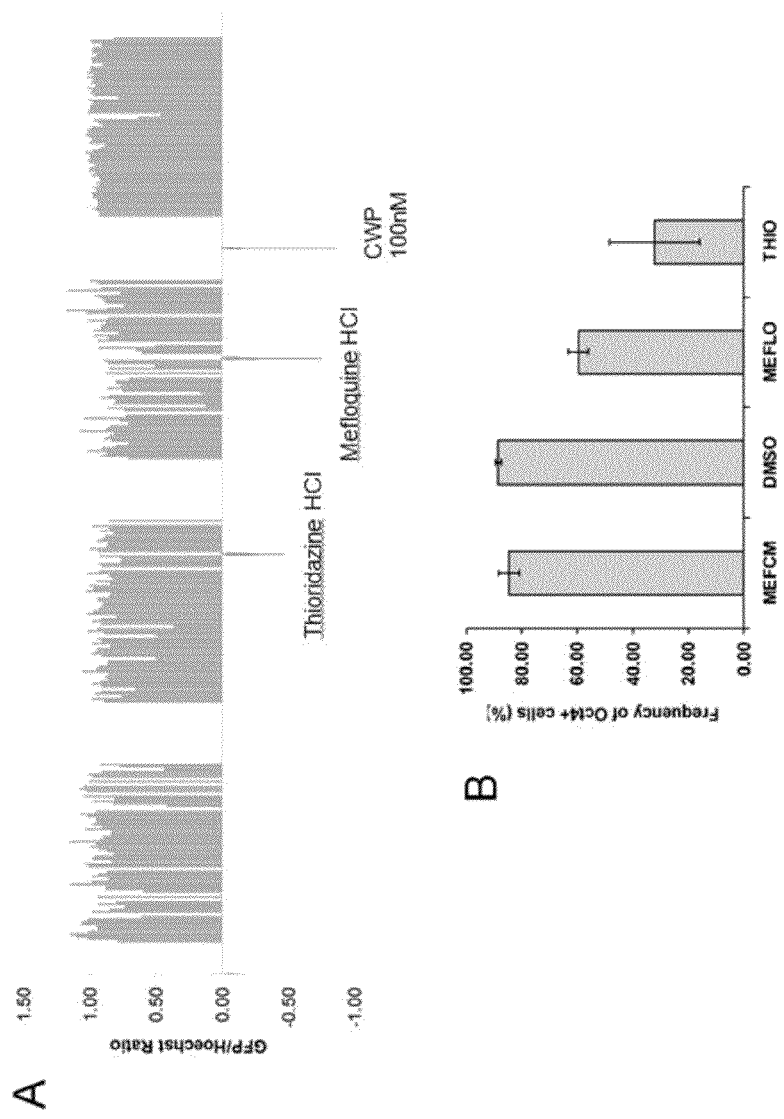
FIG. 29 shows the screening and testing of 300 compounds for induction of stem cell differentiation and toxicity to human cells. Figure A: identification of inducers of stem cell differentiation. 300 compounds were screened to detect the fluorescence emitted from the Oct4-GFP reporter expressed in transformed cells and normalized to the relative cell nuclear number as defined by Hoechst staining. GFP/Hoechst ratios below zero, the threshold defined by BMP4 (a known stem cell differentiator), are considered potent inducers of stem cells differentiation. Figures B-C: the frequency of Oct4+ human iPS cells measured using flow cytometry following 7 days of treatment with Mefloquine (MEFLO) or thioridazine (THIO) compared to culture media (MEFCM) and culture media supplemented with DMSO (DMSO). The frequency of Oct4+ cells was found to decrease with both MEFLO and THIO indicating a loss of a key stem cell marker.
Figure 29:
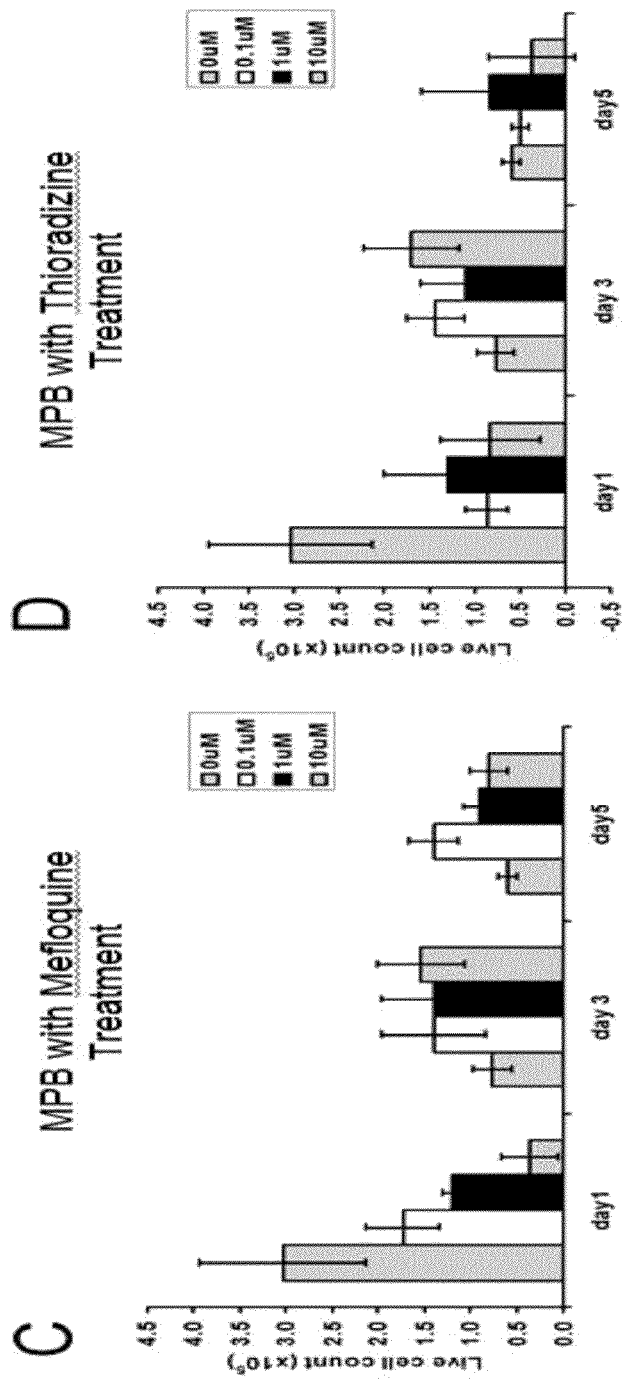

The cells and methods described herein are useful for identifying compounds that have differential activity on stem cells compared to transformed cells such as t-hPSCs (see Example 6 and FIG. 28). Furthermore the methods described herein are readily employed in high-throughput assays to screen compounds for their effects on cells, such as to identify compounds that are inducers of stem cell differentiation (see Example 7 and FIG. 29). Optionally, the methods are useful for identifying compounds with anti-cancer activity. Optionally, the methods further comprise testing the compounds identified using the screening methods described herein for toxicity.

In one embodiment, detecting an effect of a compound on a t-hPSCs or normal stem cell comprises detecting the expression of a biomarker. In one embodiment, the biomarker is a pluripotency marker or a molecular marker linked to a signaling pathway such as Wnt, hedgehog, TGF beta, fibroblast growth factor, notch, Insulin-like growth factor, FMS-like tyrosine kinase 3 and retinoic acid. Optionally, the biomarker is a marker indicative of cell proliferation, cell cycle, apoptosis, cell death, or cell adhesion.

In one embodiment there is provided a method for screening a compound for its ability to cause a loss of pluripotency comprising contacting the compound with a t-hPSC wherein expression of a pluripotency marker in the cell is operably linked to a reporter gene. In one embodiment a decrease in the expression of the reporter gene indicates the compounds ability to cause a loss of pluripotency.

As used herein the phrase "wherein expression of a pluripotency marker in the cell is operably linked to a reporter gene" means that mechanisms which normally would result in the expression of endogenous cell markers of pluripotency also in result in the expression of an exogenous reporter gene. In some embodiments, the pluripotency markers may include one or more of Oct4, Sox2, Nanog, SSEA3, SSEA4, TRA-1-60, TRA-1-81, IGF1 receptor, connexin 43 and E-cadherin. Alkaline phosphatase, REX1, CRIPTO, CD24, CD90, CD29, CD9 and CD49f. For example, the cell may be transfected with a vector containing an Oct4 promoter driving the expression of a reporter gene. In one embodiment, a loss of pluripotency is measured using the system described in Hotta et al. Nature Methods 2009 6(5):370-376).

In some embodiments, the reporter gene is Green Fluorescent Protein (GFP), however a person skilled in the art will appreciate that other reporter genes that generate a detectable signal such as luciferase or dsRed may also be used. In one embodiment, cell is transfected with an Early transposon promoter Oct-4, Sox2 and Nanog enhancers (EOS) lentiviral vector reporter coupled to a reporter gene.

Figure 7:
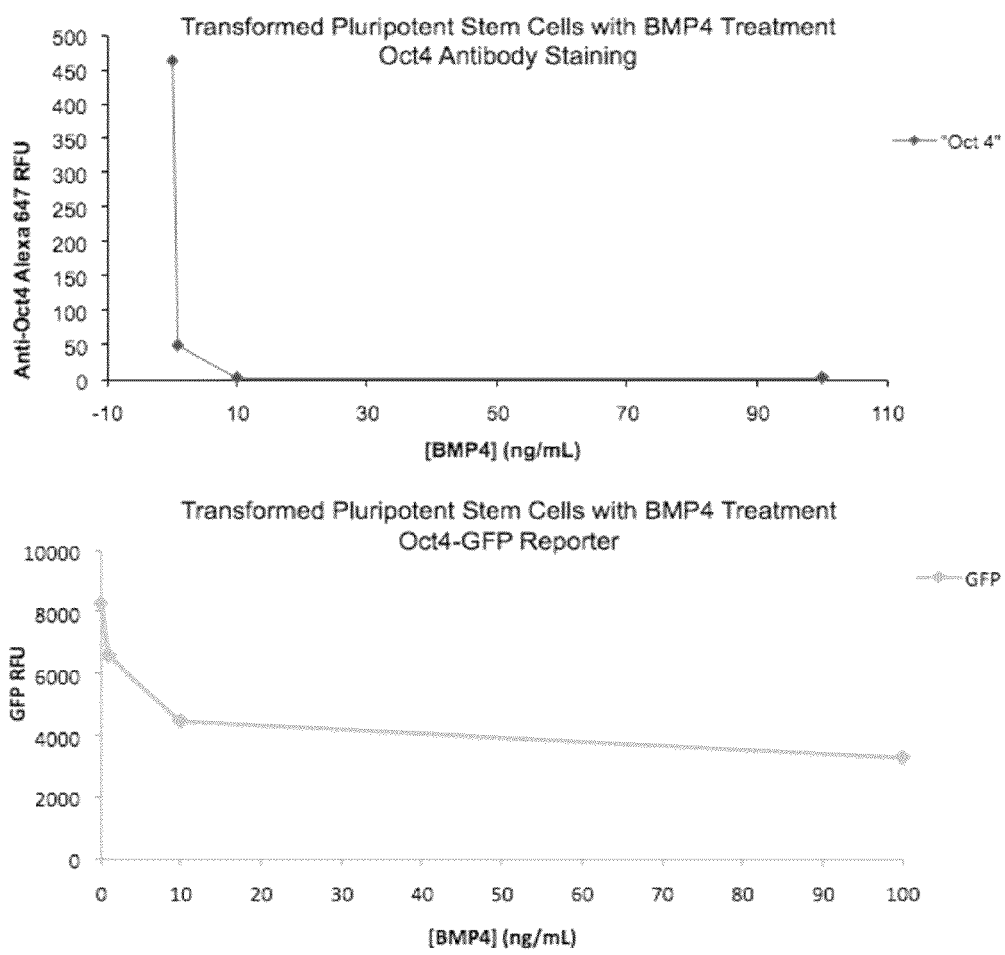
FIG. 7 shows High Throughput Screening (HTS) using transformed stem cells. Transformed pluripotent stem cells were passaged as single cells using Trypsin and seeded at 1000 cells per well into 96 well optical imaging plates coated with Matrigel® containing 100 ul mouse embryonic fibroblast conditioned media (MEF-CM). Plates were incubated at 37 degrees for 24 Hr before treatment with bone morphogenic protein 4 (BMP4) commenced. Cells were treated with either 1 ng/mL, 10 ng/mL, 100 ng/mL, or 0 ng/mL BMP4 for 4 days (n=3). After 4 days cells were fixed with 2% paraformaldehyde and stained with Oct4-Alexa 647 antibody. Cells were loaded into a plate reader and measured at excitation emission pairs of 650/665 and 488/520 nm to measure Oct4-Alexa 647 antibody (top graph) and GFP (bottom graph) respectively. Pluripotency (measured by the loss of OCT4 and GFP expression) decreased with the increase in differentiation inducing compound BMP4. Similar results were obtained when other compounds were tested.

One embodiment of an assay for screening a compound for causing a loss of pluripotency is described in FIG. 7. A person skilled in the art will appreciate that such an assay may also be used to identify compounds that induce differentiation of stem cells.

Figure 11:
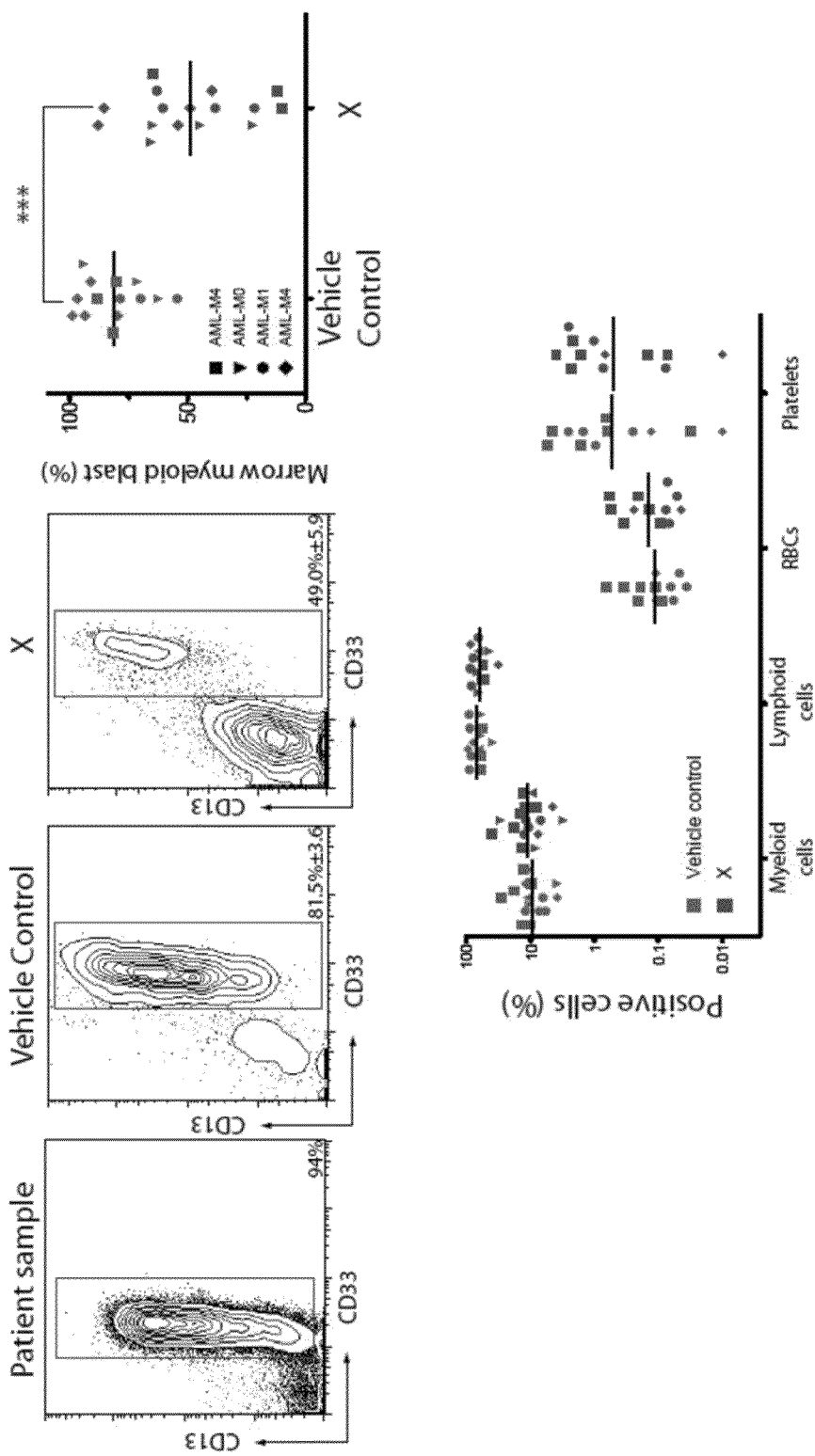
FIG. 11 shows the presence of AML-blast detected by flow cytometry. 8-weeks-old sublethally irradiated NOD/SCID IL2Rgc null mice were transplanted with an AML sample. Two weeks after transplant, mice were treated daily for 10 consecutive days with the compound "X" drug or vehicle control. Bones were harvested from transplanted mice 8 weeks after and the presence of AML-blast detected by flow cytometry. As a control, mice were transplanted with healthy HSCs and treated as AML-transplanted ones. Treatment with compound "X" reduced the level of reconstitution in AML transplanted mice.
Figure 12:
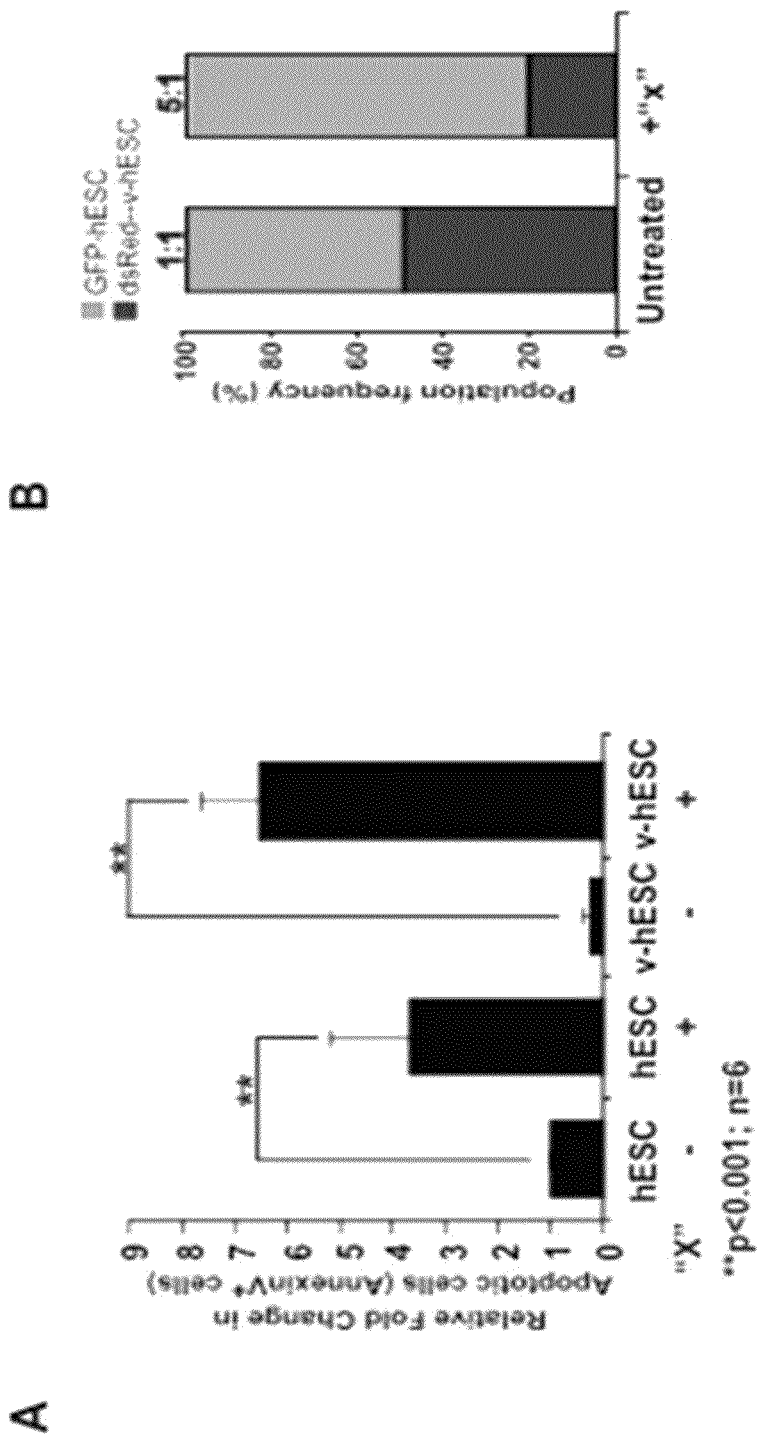
FIG. 12 shows that a small molecule inhibitor preferentially targets the transformed hESCs (v-hESC) versus normal hESCs promoting hematopoietic differentiation.
Figure 12:
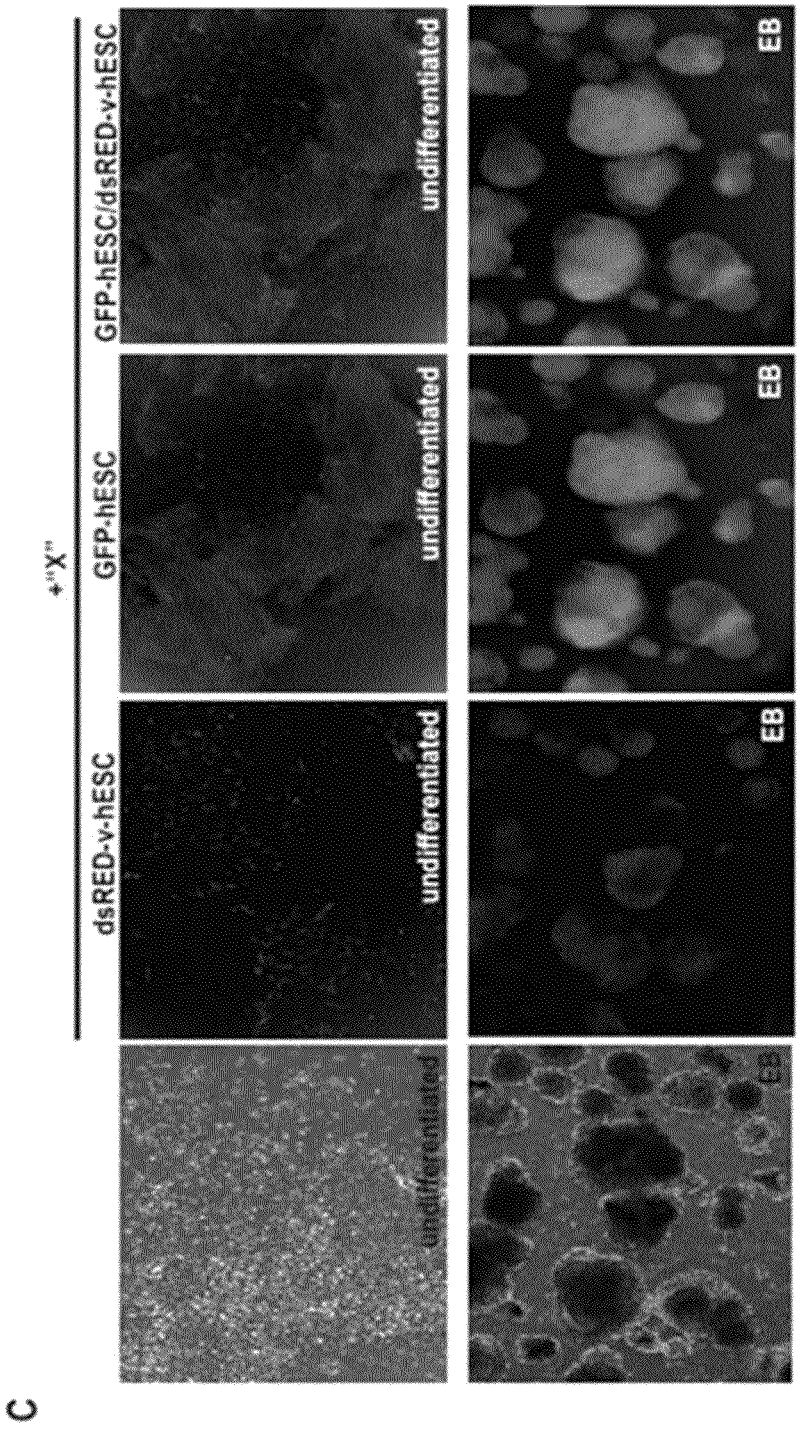
Figure 12:
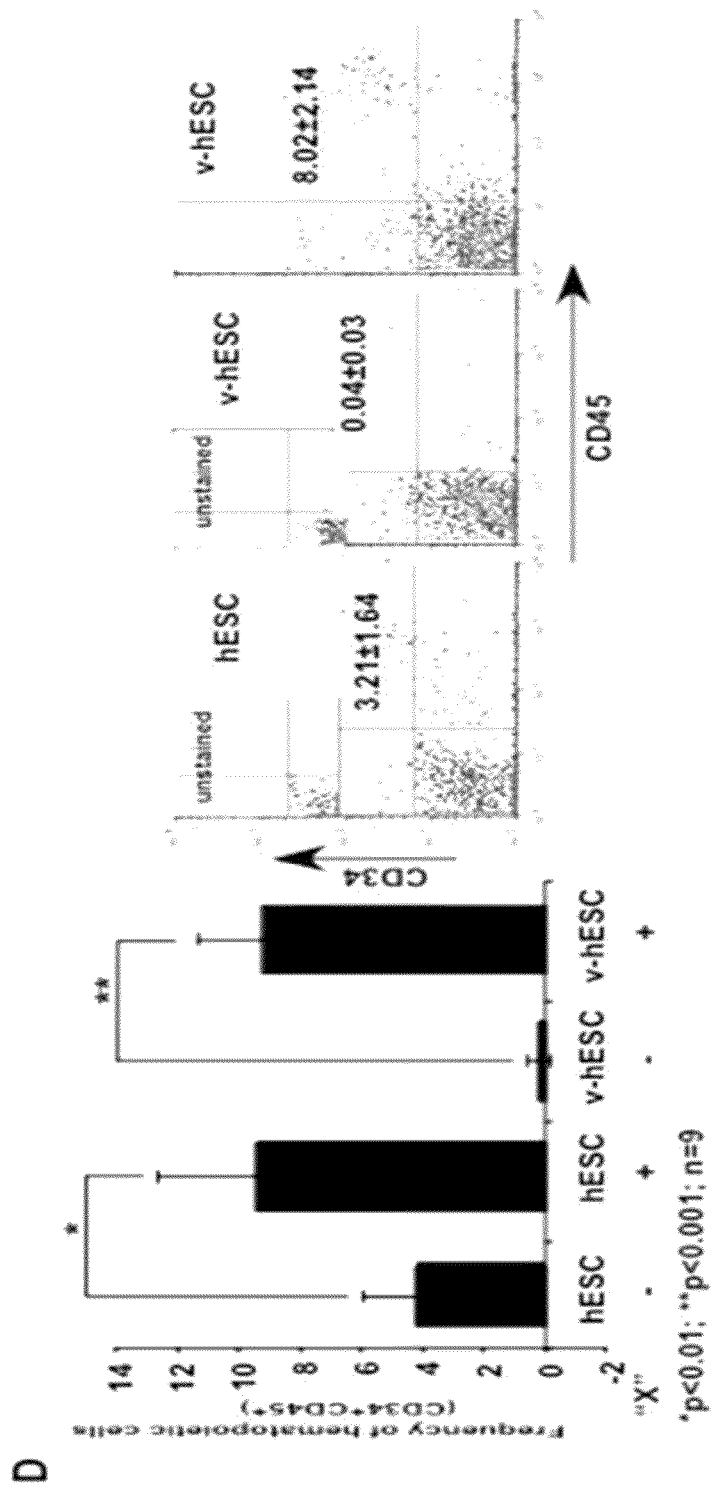

The t-hPSC cells described herein may also be used as a model to study cancer stem cells. In one embodiment, the t-hPSC cells may be used to identify compounds with apoptotic activity. As shown in FIGS. 11 and 12, t-hPSC cells may be used in cell-based assays to predict the antic-cancer activity of a compound in vitro.

Figure 18:
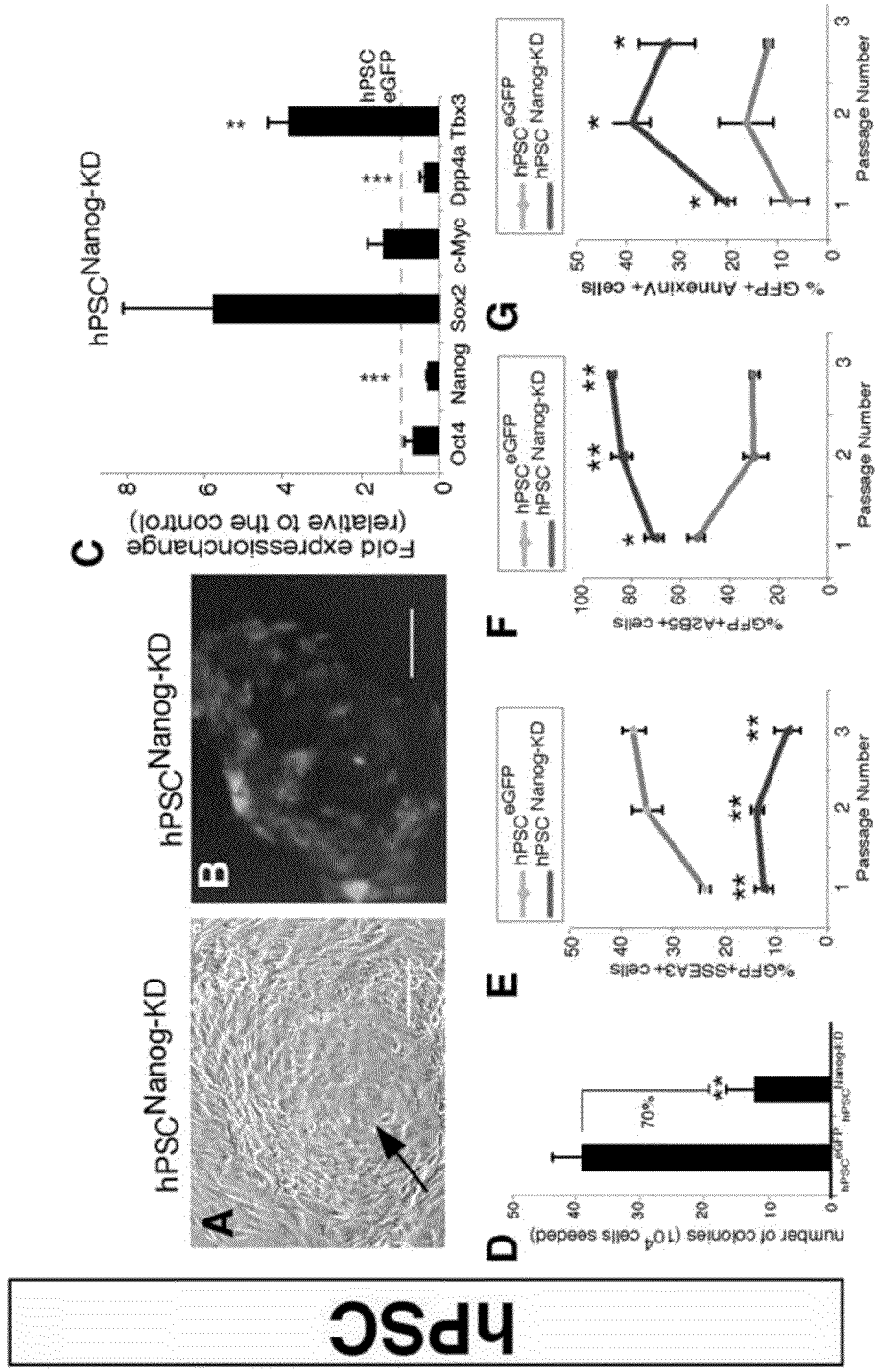
FIG. 18 shows that t-hPSCs exhibit a heightened self-renewal and survival response following Nanog dysregulation. (A-B) Representative images of normal hPSC bulk culture one week after transduction with a lentivector carrying an shRNA sequence targeting Nanog. Scale bar=100 µm, n=5. A: Phase contrast. B: GFP. Arrow denotes differentiated cells in an hPSC colony following Nanog knockdown. (C) qPCR demonstrating fold changes in Oct4, Nanog, Sox2, c-Myc, Dpp4a, and Tbx3 transcripts in GFP+SSEA3+ cells isolated from Nanog knockdown hPSCs relative to the control, respectively. Bar graphs represent mean values±SEM, n=3. , $p<0.01$, *, $p<0.001$. (D) Clonogenic self-renewal of SSEA3+ cells isolated from control and Nanog knockdown hPSCs. 1×104 GFP+SSEA3+ cells were isolated from hPSCs 2 days after transduction with eGFP control and Nanog knockdown lentiviral vectors and seeded on ihdFs. GFP+ colonies were scored 9 days after seeding. Bar graphs represent mean values±SEM, n=3. **, $p<0.01$. (E-G) Frequency of GFP+SSEA3+(E) GFP+A2B5+(F) and GFP+AnnexinV+ (G) cells for three passages of culture derived from sorted GFP+SSEA3+ fractions of control and Nanog knockdown hPSCs. Lines represent mean values±SEM, n=3. * $p<0.05$, ** $p<0.01$. (H-l) Representative images of t-hPSC bulk culture one week after transduction with a lentivector carrying an shRNA sequence targeting Nanog. Scale bar=100 µm, n=5. H: Phase contrast. I: GFP. Arrow denotes t-hPSCs undergoing apoptosis following Nanog downregulation. (J) qPCR demonstrating fold changes in Oct4, Nanog, Sox2, c-Myc, Dpp4a, and Tbx3 transcript in GFP+ cells isolated from Nanog knockdown t-hPSCs. Bar graphs represent mean values±SEM, n=3, *, $p<0.05$, , $p<0.01$, *, $p<0.001$. (K) Clonogenic self-renewal of GFP+ cells isolated from control and Nanog knockdown t-hPSCs. 1×104 were sorted from t-hPSCs 4 days after transduction with eGFP control and Nanog knockdown lentiviral vectors and seeded on ihdFs. GFP+ colonies were scored 6 days after seeding. Bar graphs represent mean values±SEM, n=3. **, $p<0.01$. (L-N) Frequency of GFP+SSEA3+(L) GFP+A2B5+(M) and GFP+AnnexinV+(N) cells for three passages of control and Nanog knockdown t-hPSCs. Lines represent mean values±SEM, n=3. * $p<0.05$.** $p<0.01$.
Figure 18:
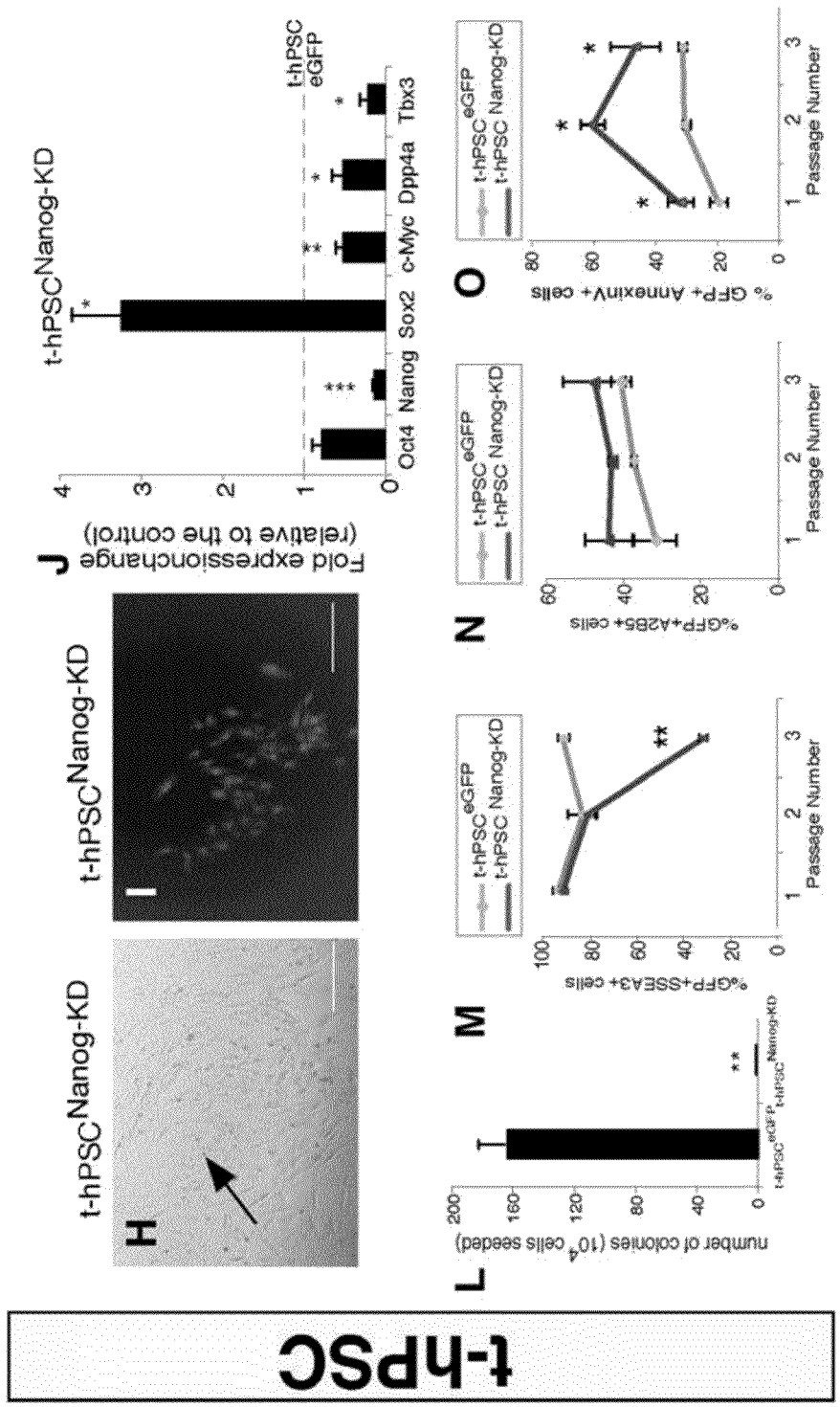

The present applicants have identified transformed human pluripotent stem cells that exhibit similar characteristics as cancer stem cells. The applicants have also identified that t-hPSC cells exhibit hypersensitivity to the presence of the transcription factor Nanog as shown in Example 4. Surprisingly, Nanog downregulation completely abolished the colony forming capacity of t-hPSCs as shown in FIG. 18K and induced cell death (apoptosis) as shown in FIG. 18N.

Accordingly, the present disclosure provides a method of inducing apoptosis in cancer stem cells comprising inhibiting, reducing or interfering with the expression or activity of Nanog. Another embodiment includes use of the t-hPSC cells described herein for identifying compounds that inhibit, reduce or interfere with the expression or activity of Nanog.

The t-hPSC cells described herein offer a number of advantages for use in cell-based screening assays, and in particular high-throughput cell-based screening assays. For example, t-hPSC cells in culture form a homogeneous monolayer of cells without cell overlap and single seeded t-hPSC cells are able to rapidly grow to suitable numbers for performing cell assays as shown in Example 2 and FIGS. 5 and 6. Accordingly, in one embodiment there is provided a method for culturing cells for use in a cell-based screening assay comprising placing one or more transformed human pluripotent stem cells into a receptacle and culturing said cells in the receptacle to form a monolayer of stem cells without cell overlap. The lack of cell overlap in cultures of t-hPSC cells facilitates the use of image analysis software for identifying and analyzing individual cells.

As used herein, the term "receptacle" refers to a container suitable for the maintenance and culture of cells. In some embodiments, the receptacle may be a well on a plate such as a microtitre plate, which optionally contains a plurality of wells or receptacles. Optionally, the receptacle is designed so as to prevent contamination from adjacent receptacles. Typically, the receptacle will also contain media to provide nutrients to the one or more cells and allow for cell growth. In one embodiment, the receptacles are Matrigel™ coated microtitre plates.

In one embodiment, there is provided a composition comprising microtitre plates with a plurality of receptacles wherein one or more of the receptacles contain t-hPSCs or t-iPSCs as described herein. In one embodiment, the microtitre plates are high-throughput format microtitre plates. In one embodiment, the plates are high-density plates suitable for cell-based assays or culture. In some embodiments, the plates have 2 or more, 96, 384, or 1536 individual receptacles or wells and are suitable for use in high-throughput screening such as in automated systems and/or robotic systems.

In another aspect, the present inventors have developed a method of plating selected morphologically homogeneous cell clusters (undifferentiated cells) isolated mechanically by punching of normal stem cell colonies with a sharp instrument, such as a fine point pipette tip, or by scoring the colonies with a sharp tool and removing the cell clusters of interest by repeated pipetting with or without further fluorescence based selection (large particle cell sorter—COPAS) and transferring of the cell clusters to individual wells. Cells plated using this method are useful in stem cell screening assays and in comparative assays with t-hPSCs.

Colony localization can be accomplished by: 1) plating cells directly in the center of the well; 2) plating the cell clusters in a location of the well which would be as far away from the borders of the well as necessary to allow for the full growth of the cells during the screening period, within the imaging field and without physical disturbances; 3) plating on well coated with adhesive molecules in predetermined patterns; and 4) plating the cell clusters in a solution droplet in a dry well and waiting for a defined period for cell attachment before filling the well with culture medium; this can be done with or without the addition of substrates.

Using this technique subcultures were created comprising a defined number of undifferentiated colonies which showed predictable growth (cell line specific) and differentiation under defined conditions (based on SSEA3 and Oct-4 expression. In addition, this method facilitated colony localization prediction which in turn reduced the screening time/well.

Accordingly, in one embodiment, the application provides a method of creating a subculture of undifferentiated stem cells comprising:
(a) isolating a cell cluster comprising undifferentiated stem cells from a single colony;
(b) transferring the cell cluster to a well, wherein the cells of the cluster are plated in a predetermined location in the well;
(c) culturing the cells produce the subculture of undifferentiated stem cells.

The term "cell cluster" as used herein refers to a group of stem cells formed from disruption of confluent or semi-confluent bulk culture of stem cells. Generally the cell cluster is obtained from colonies that have reached the tipping point by which any further culture will induce differentiation. The cell cluster will comprise at least 2 cells and generally more than 50 cells. The diameter of the cluster will depend on the culture conditions and the length of the culture time and can range from 200-500 μm, more specifically 150-300 μm. In one embodiment, the cells are cultured for a culture period under conditions that maintains undifferentiated cells. For example, in one embodiment the culture period ranges from 1 hour to 48 hours. In one embodiment, the culture period ranges from 24 hours to 4 weeks. Optionally, the culture period ranges from 24 hours to 1 week, or from 24 hours to 2 weeks.

In one embodiment, the isolation of cell clusters in step (a) is from an area of the colony that does not contain differentiated cells. This area is typically the inner ⅔ and preferably the inner ⅓ of the colony (see FIG. 36).

In another embodiment, the isolation of a cell cluster from a single colony in step (a) comprises mechanically punching colonies, for example, with a sharp instrument such as a fine point pipette tip, or scoring the colonies with a sharp tool and removing the cell clusters of interest by repeated pipetting. The punched colony or pipetted clusters are then plated in step (b).

In another embodiment, the method further comprises subjecting the cells of step (a) to fluorescence-based selection prior to transfer to a well in step (b). In one embodiment, the fluorescence-based selection comprises large particle cell sorting (COPAS).

The term "a predetermined location" as used herein refers to one or more specific locations in the well where the cells are plated. In one embodiment, the predetermined location comprises a location furthest away from the borders of the well. In another embodiment, the predetermined location comprises the centre of the well.

In one embodiment, the well comprises an adhesive layer patterned onto a non-adhesive surface at the predetermined location or locations. In such an embodiment, the plated cells will adhere to the adhesive layer or layers but will not spread to the non-adhesive surface. Adhesive layers include, without limitation, matrigel, which is a basement membrane analogue. Laminin, fibronectin, collagen (e.g. types I, III and IV) elastin, gelatin vitronectin, fibrin are other examples of adhesive biological materials. Non-biological materials include plasma treated polystyrene. In an embodiment, the non-adhesive surface comprises repellent plastic or low adhesion plates. In another embodiment, the non-adhesive surface is created by treating plates with agents that convert the polarity of the tissue culture surface, such as pluronic, Pluronic, polyethylene glycol and polyethylene oxide.

A large demand exists for screening of chemicals and other substances on undifferentiated cell cultures since this constitutes a predictive assay for the determination of the capacity of the substance to induce differentiation into specific cell types to be used for replacement therapy. Furthermore, stem cell screening is attracting a high level of interest with regards to its potential as models for primary screens, secondary pharmacology and toxicity evaluation.

In order to perform this assay one must establish a consistent and predictable culture of undifferentiated cells. Differentiated cells derived from pluripotent cells often grow at a much faster speed than undifferentiated cells taking over the culture and compromising the predictability of differentiation kinetics. The methods described herein overcome these issues enabling stem cell culture in high throughput format and allowing for patterned cell culture which facilitates the identification of colonies in culture by automated imaging.

Accordingly, in another embodiment, there is provided a method of high throughput screening of stem cells comprising (a) preparing a plurality of subcultures of undifferentiated stem cells by the methods described herein;
(b) contacting the plurality of subcultures with a test compound;
(c) subjecting the treated plurality of subcultures to automated analysis.

The term "plurality" as used herein refers to more than 1, 5, 10, 50, 75, 100, 1000, or more than 1500 subcultures.

In one embodiment, each well or receptacle contains one subculture. In such an embodiment, the plurality of subcultures comprises a plurality of wells or receptacles. In an embodiment, the wells are contained on a microtiter plate.

In one embodiment, the test compound is a chemical or other substance that is being tested for its effect on differentiation of the stem cells into specific cell types. In such an embodiment, the high throughput screening is used to identify compounds useful in replacement therapy. In another embodiment, the test compound is a chemical or drug and the high throughput screening is used as a primary screen, or as a secondary pharmacology and toxicology evaluation screen for the chemical or drug. In one embodiment, the automated analysis comprises detecting the effect of the compound on one or more subcultures of stem cells. Optionally, the method further comprises contacting one or a plurality of t-hPSCs with a test compound and subjecting the t-hPSCs to automated analysis. In one embodiment, the method further comprises comparing the results of the analysis of subcultures of stem cells contacted with the test compound to the analysis of subcultures of t-hPSCs contacted with the test compound.

The automated analysis may include, without limitation, analysis of the state of differentiation of the cells, for example, by detecting cell surface molecules indicative of various differentiation states or analysis of the proliferation or survival of cells, by detecting levels of apoptotic markers or cell death and debris, cells transduced with lentiviral vectors that report GFP expression when the cells is in a pluripotent state. In one embodiment, subcultures of undifferentiated stem cells created by the methods described herein are tested and used as controls.

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Characterization of Human Embryonic Stem Cells with Features of Neoplastic Progression The acquisition of genetic and epigenetic abnormalities in human embryonic stem (hES) cell lines has raised safety concerns about the use of these cells in regenerative medicine (1-14). Indeed, the finding that aggressive cancers express hES cell-associated genes (15) suggests that hES cells are vulnerable to neoplastic progression. In the context of clinical application, it will therefore be important to detect the emergence of cancerous cells among normal hES cells. This is a challenging task given that hES cells with cancer-cell characteristics may resemble normal hES cells with respect to properties such as self-renewal, teratoma formation and the expression of pluripotency markers. Most studies that have examined transformation of hES cells have been limited to determination of karyotypic abnormalities and did not include extensive functional characterization (2-9,12,13). At the cellular level, transformation refers to the collective changes, including uncontrolled cell division and morphological alterations, that convert a normal cell into a cancer cell (16). The present applicants have examined functional criteria of transformation in hES cells and in one embodiment have the aim of establishing a reliable approach for identifying partially transformed cells and avoiding their use in experimental and clinical applications.

Figure 1:
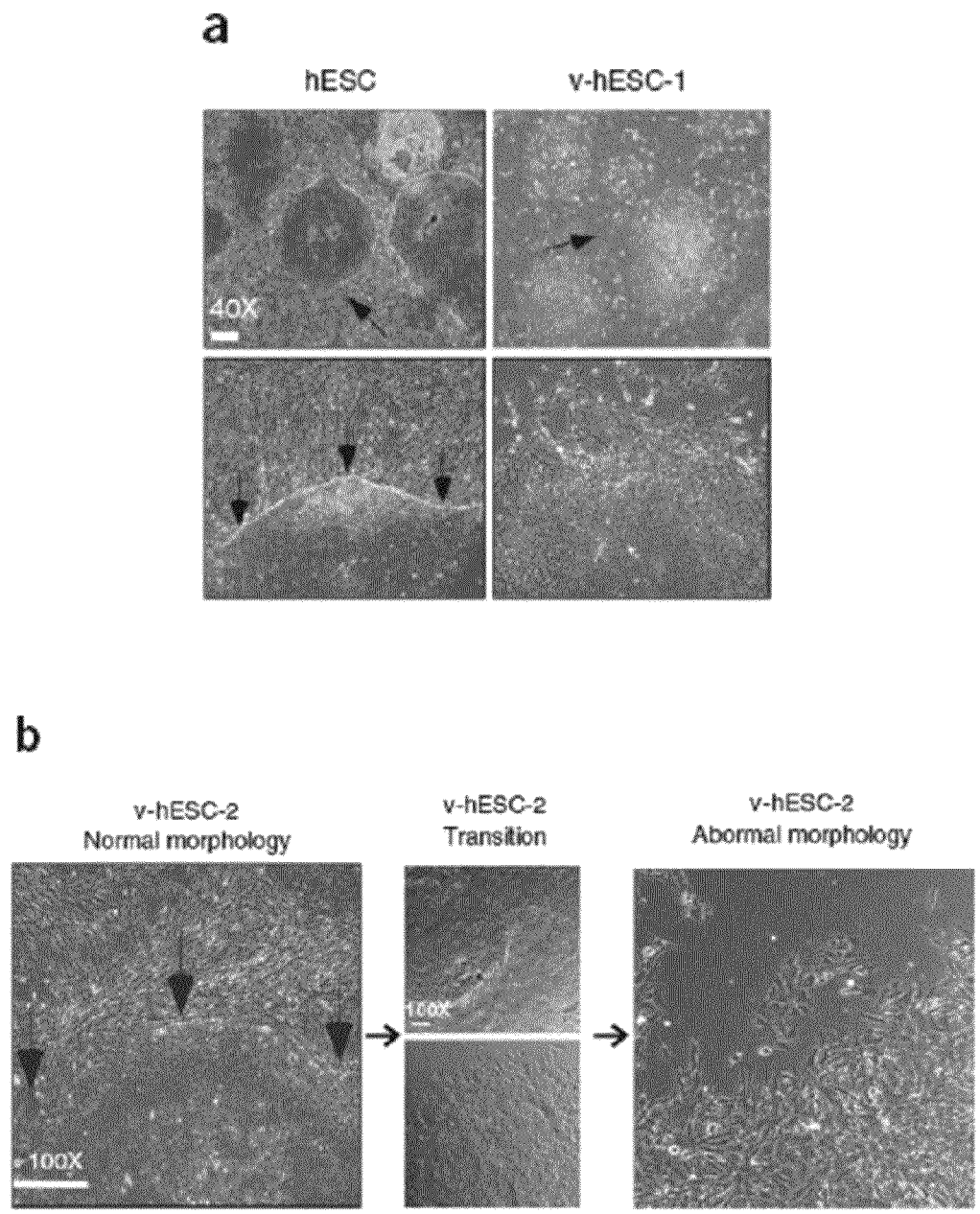
FIG. 1 shows that variant hES cells (t-hPSCs) are morphologically and phenotypically different from normal hES cells. (a) Morphological features of v-hESC-1. Compared with hESC, v-hESC-1 has lost the surrounding fibroblast-like support layer and well-defined colony edges. Arrows indicate the fibroblast-like layer in the left panels and the lack of these cells in the right panels. Scale bars, 500 μm. (b) Morphological changes in v-hESC-2 over time. In the 'normal morphology', a subpopulation of fibroblast-like cells surrounds round colonies with sharp borders (left panel). After several passages in the same culture conditions, v-hESC-2 begin to lose the fibroblast-like cells, and the colonies appear less defined as the cells transition into a mosaic culture (middle panels) before reaching a fully variant state (right panel). (c) Immunocytochemical analysis of Oct4 (green) and SSEA3 (red) in hES cells (left panels) and v-hESC-1 cells. Nuclei are stained with DAPI (blue). Arrow in the left panel indicates absence of Oct4 and SSEA3 staining in fibroblast-like cells. Arrow in the right panel shows Oct4+/SSEA3+ cells outside the colony. Inset: isotype control. Scale bars, 400 μm. (d) Representative flow cytometry analysis of SSEA3 and SSEA4 expression in hESC (left panels) and v-hESC-1 cell (right panels) cultures. Inset: isotype controls. Live cells were gated on 7AAD. (e,f) Quantification of flow cytometry shown in d for hESC and v-hESC-1 cell cultures. N 1/4 3. Error bars, s.e.m. **, $P<0.01$. (g) Immunophenotypic changes in v-hESC-2 over time. SSEA3 and SSEA4 levels were 56% and 62%, respectively, at passage 47 before transition to a variant state, when they increase to 90.4% and 90.5%, respectively, at passage 75.
Figure 1:
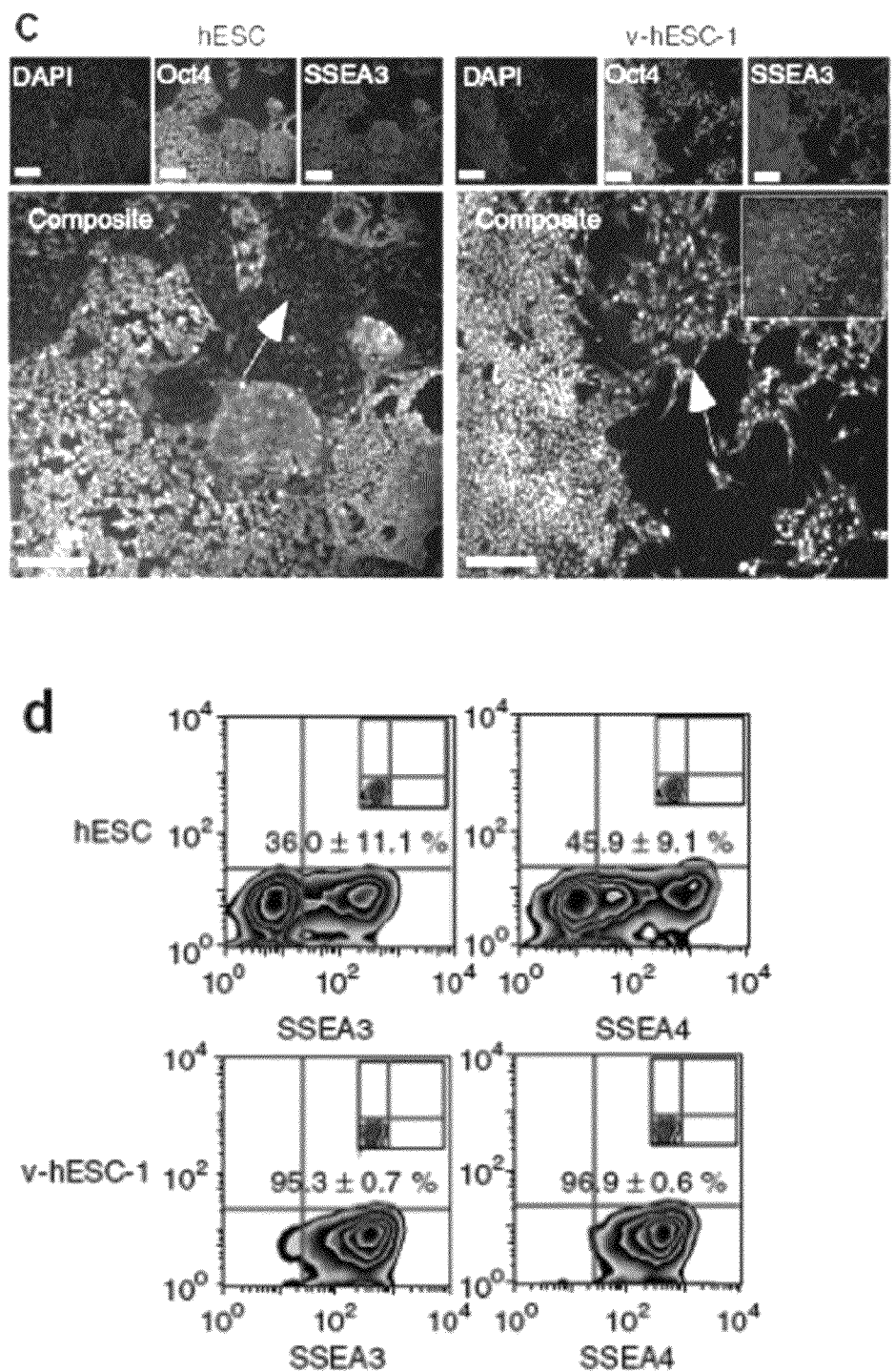
Figure 1:
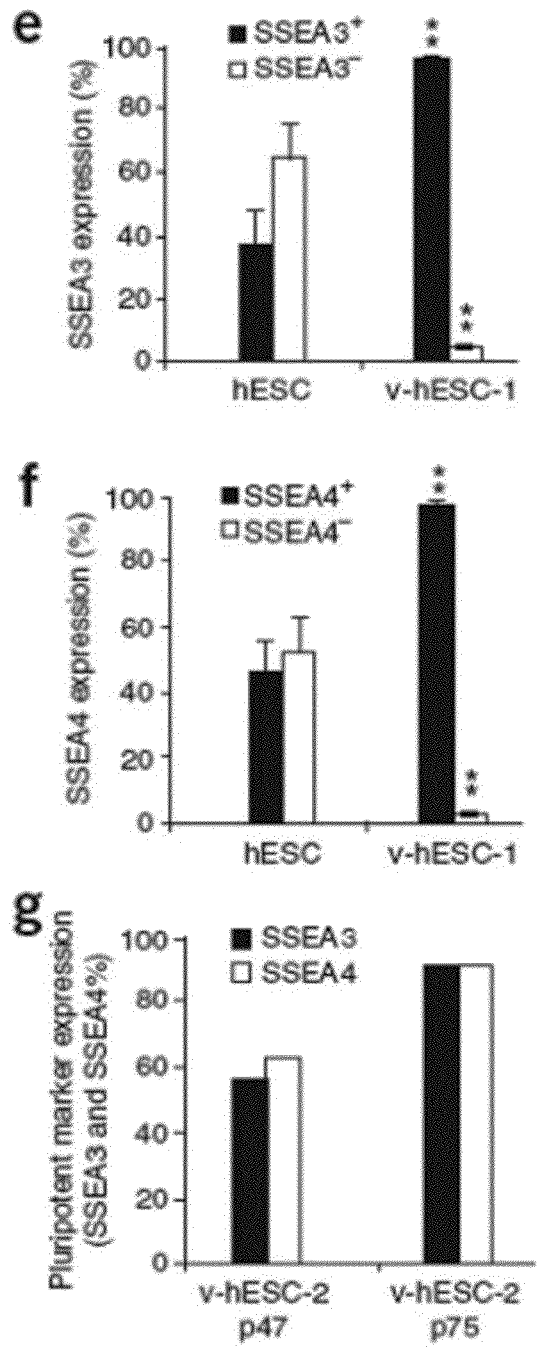

FIG. 1 describes a variant of the H9 hES cell line (v-hESC-1) with morphological differences from other hES cell lines in culture, including lack of well-defined colony edges and loss of the surrounding fibroblast-like cells that normally appear in hES cell cultures (17,18). A similar morphology was observed in multiple subclones, including v-hESC-2 (also derived from H9) (FIG. 1 b). The morphological changes developed gradually over about 5 passages, suggesting the emergence of mosaic cultures, and the lines were maintained in culture for an additional 20-24 passages (FIG. 1 b). v-hESC-1 and v-hESC-2 were tested for karyotypic abnormalities by spectral karyotyping (SKY). Twenty metaphase spreads have been reported to be sufficient for cell line characterization (19); however, as hES cell cultures are phenotypically heterogeneous, a minimum of 200 metaphase cells were used. No major chromosomal abnormalities were detected in v-hESC-1 (n 1/4 215 cells), v-hESC-2 (n 1/4 500 cells) or in a normal H9 hES cell line, designated hESC (n 1/4 500 cells), whereas the teratocarcinoma cell line EP2102 (n 1/4 500 cells) exhibited various aberrations. These findings were confirmed by interphase fluorescence in situ hybridization (FISH) analysis and G-banding. Thus, variant and normal hES cells were indistinguishable by the cytogenetic criteria often used to assess normality (2-9,12,13).

Human ES cells express the pluripotency markers Oct4 and SSEA3, with the SSEA3+ subpopulation possessing a higher clonogenic capacity and distinct cell-cycle properties (17). In normal cultures, SSEA3 and Oct4 were expressed exclusively within the colonies of hES cells (FIG. 1c, left panels and ref. 17), whereas in variant cultures, they were also detected within small clusters and individual cells surrounding the hES cell colonies (FIG. 1c, right panels). By flow cytometry analysis, SSEA3 and SSEA4 frequencies were 36.0±11.1% and 45.9±9.1%, respectively, in hESC, and 95.3±0.7% and 96.9±0.6%, respectively, (n 1/4 5 for each cell line, P o 0.01) in v-hESC-1 (FIG. 1d-f). In v-hESC-2, the frequencies increased to 90.4% and 90.5%, respectively, as measured at passage 75 (FIG. 1g). Thus, the observed loss of surrounding fibroblast-like cells in the variant hES cell cultures correlates with an increase in the proportion of cells expressing pluripotency markers. The high expression of pluripotency markers and the lack of chromosomal abnormalities suggest that variant hES cells could be mistaken for superior hES cells with enhanced 'sternness'.

Figure 2:
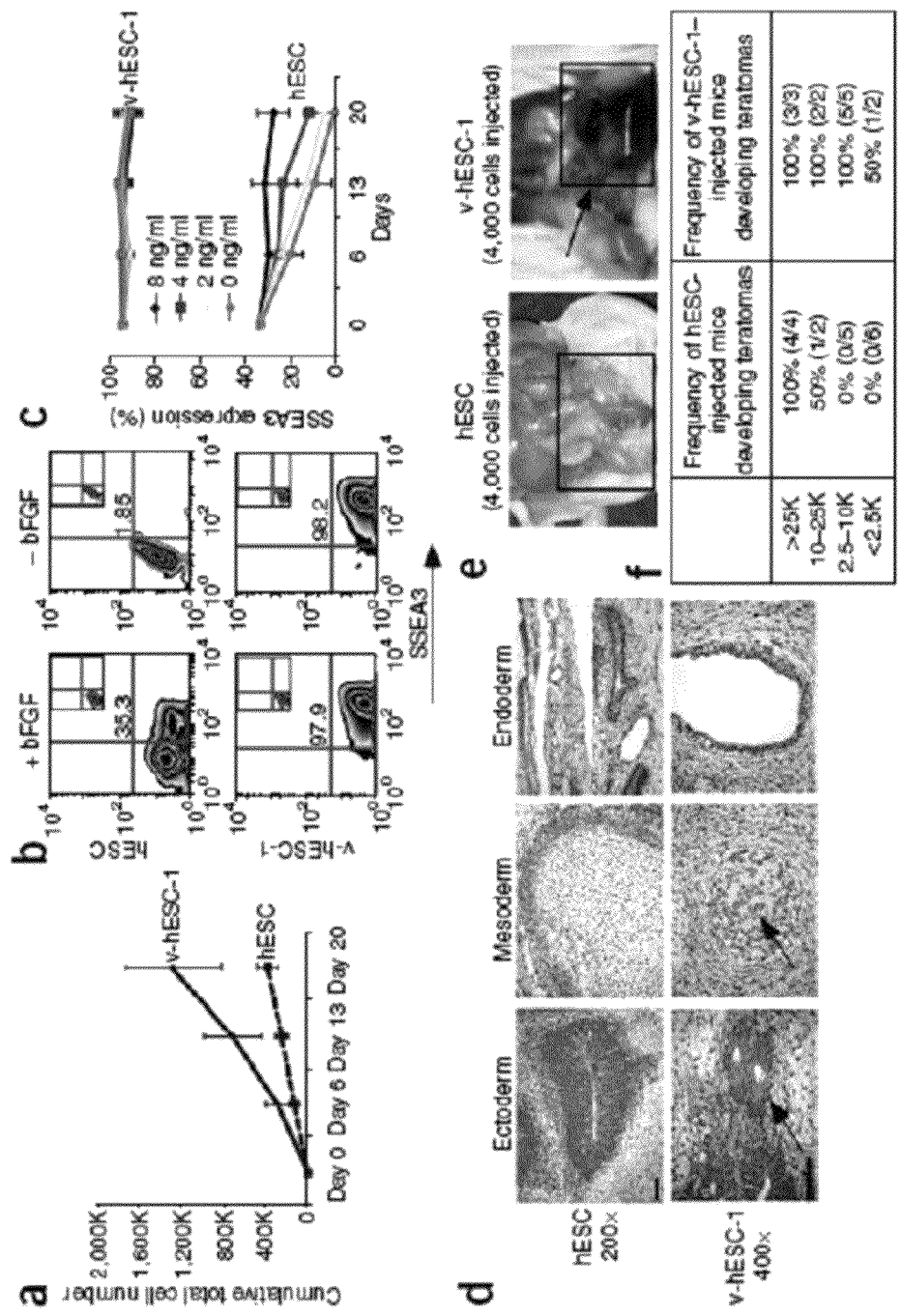
FIG. 2 shows that variant hES cells exhibit dysregulated cell-cycle and self-renewal properties in vitro and tumor-initiating cell frequency in vivo. (a) Cumulative growth of hESC and v-hESC-1 cells over 20 d in culture. Error bars, s.e.m. (b) Flow cytometry analysis of SSEA3 expression in hESC and v-hESC-1 cells under depleted bFGF conditions over 20 d. Insets: isotype controls. (c) Quantification of SSEA3 frequency in hESC and v-hESC-1 under varying concentrations of bFGF over 20 d in culture. (d) Immunohistochemical analysis of the three germ layers present in teratomas from hESC and v-hESC-1. Arrows indicate primitive, underdeveloped neural rosettes in teratomas derived from v-hESC-1 and early bone in v-hESC-1 teratomas. Scale bars, 100 μm. (e) Injection of ~4,000 hESC cells produces no teratomas, whereas a large, highly vascularized teratoma (arrow) was seen with ~4,000 injected v-hESC-1 cells. (f) Frequency table showing the number of mice developing teratomas as a percentage of the number of mice injected with hESC and v-hESC-1. (g) Scatterplot of teratoma volumes relative to the cell number ranges injected intratesticularly into NOD-SCID mice. Teratoma volumes for hESC (solid circles) and v-hESC-1 (open circles) cells are depicted over four cell injection ranges (>25K, 10-25K, 2.5-10K and <2.5K). Note that teratomas were seen in all limiting dilutions of v-hESC-1 cells. (h,i) Linear regression model for hESC (h) and v-hESC-1 (i) mean teratoma volumes. Note the high $R2$ value ($R2=0.9818$) for v-hESC-1 teratomas. (j) Immunohistochemical analysis of Oct4 expression in hESC and v-hESC-1 teratomas produced by injection of 30,000 cells. Note the discrete localization of Oct4 staining in v-hESC-1 teratomas. N=4 for each cell line. Scale bars, 200 µm. (k) Migration assay of undifferentiated hESC and v-hESC-1 cell aggregates implanted into three-dimensional type I collagen gels 6 d after implantation. Arrows represent the radial migration path. Scale bars, 200 µm.
Figure 2:
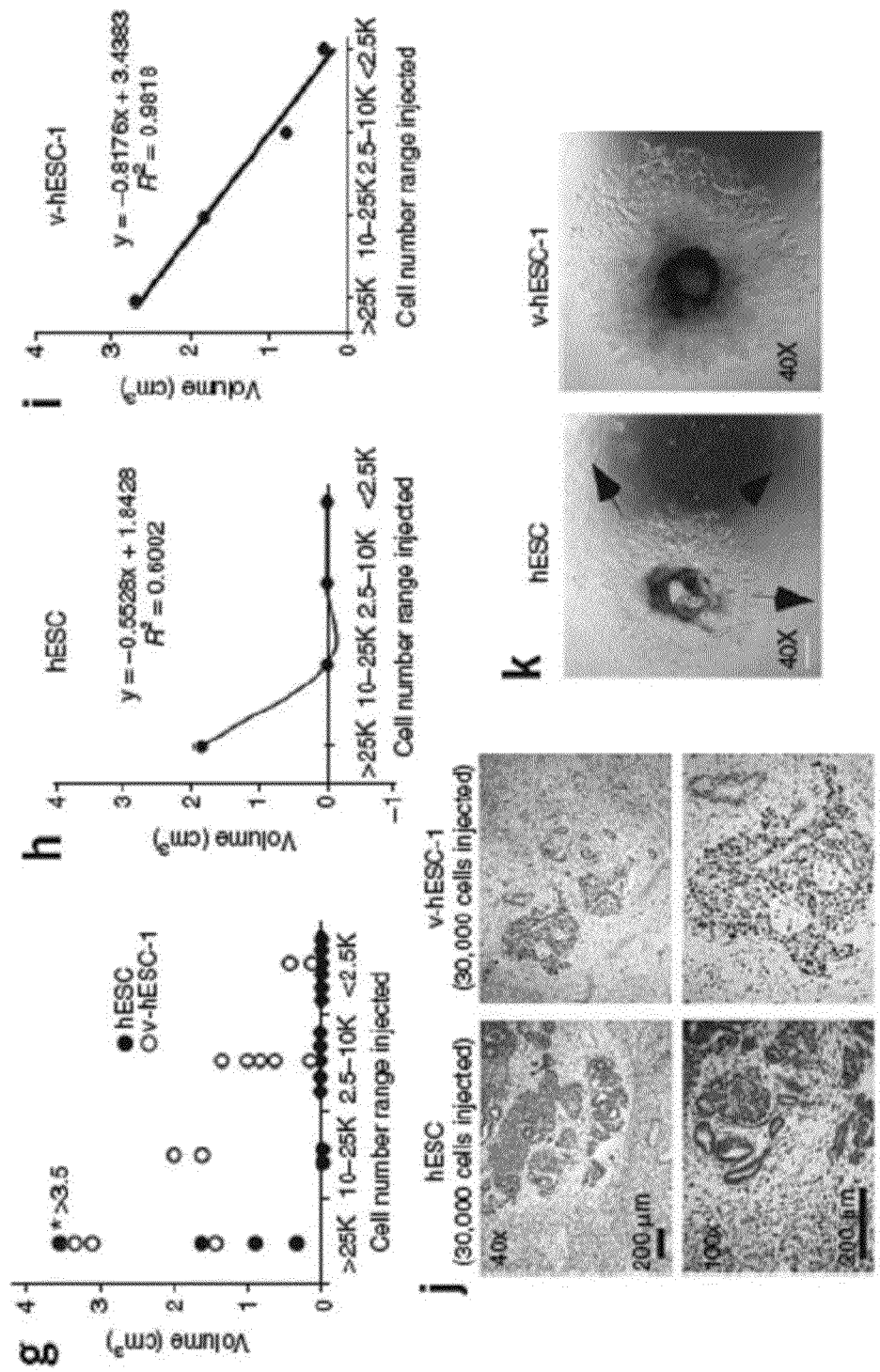
Figure 22:
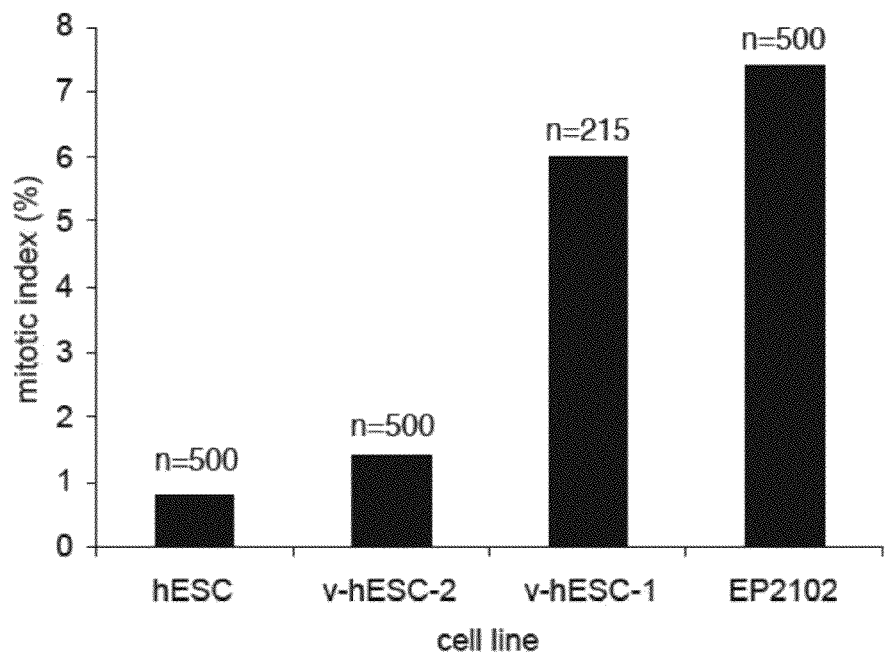
FIG. 22 shows the percentage of hESCs (N=500 cells), v-hESC-2s (N=500 cells), v-hESC-1s (N=215 cells) and EP2102 (N=500 cells) in metaphase as a measure of mitotic index.

Self-renewal and cell-cycle properties of the cell lines were also analyzed. Cumulative growth curves of hESC and v-hESC-1 revealed an approximate 3.4-fold increase in the number of variant hES cells accumulating over 20 d in culture (FIG. 2a). Analysis of mitotic index (percentage of cells in metaphase) showed that v-hESC-1 and v-hESC-2 cells proliferate more than hESC cells but less than EP2102 embryonal carcinoma cells, the malignant counterpart of ES cell (FIG. 22).

Normal hES cells are dependent on basic fibroblast growth factor (bFGF) for maintenance of the undifferentiated state and self-renewal (20). As bFGF was titrated out of the cultures over 20 d, hESC lost expression of SSEA3 whereas v-hESC-1 did not (FIG. 2b-c), indicating that variant hES cells exhibit reduced dependence on bFGF. A decreased requirement for exogenous growth factors is one feature of transformation (16).

Figure 23:
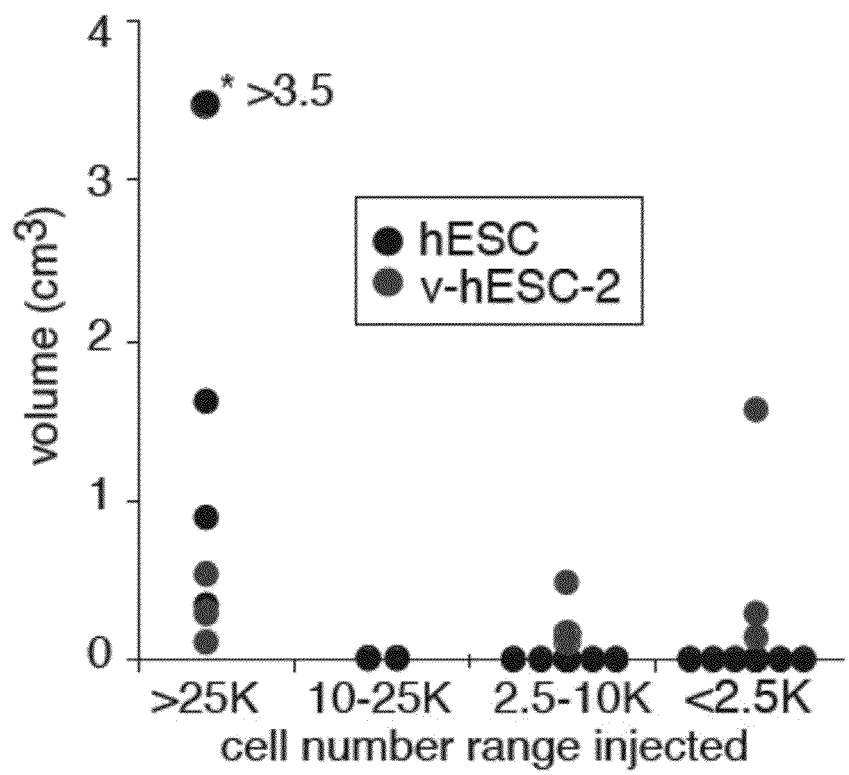
FIG. 23 shows limiting dilution teratoma assay comparing v-hESC-2 with normal hESCs. Scatterplot of teratoma formation with v-hESC-2 using different dilutions (46,000, 12,750, 2,000 cells; N=3 biological replicates for each) demonstrates that similar to the v-hESC-1 line, v-hESC-2 cells also form teratomas with fewer than 2,500 cells injected. This represents a 9-fold increase in TIC frequency compared to normal hESC teratomas.

The teratoma assay is a functional, binary test of normal hES cell pluripotency in vivo and can be used quantitatively, although to our knowledge there have been no reports on the frequency of teratoma initiating cells (TICs) in hES cell cultures. Limiting dilution teratoma assays were conducted in immunodeficient mice over 8 weeks. Teratomas generated from v-hESC-1 were highly vascularized and contained cells of all three germ layers, indicating pluripotency in vivo (FIG. 2d-e). However, compared with teratomas produced by hESC, they exhibited less-differentiated features, such as a lack of definitive mesodermal tissues and more primitive neural rosettes (FIG. 2d and FIG. 28). Limiting dilution analysis of v-hESC-1 and hESC yielded TIC frequencies of 1:800 and 1:17,500, respectively (FIG. 2f-g). This represents a 420-fold increase in TIC frequency in v-hESC-1 cells. V-hESC-2 gave similar results (FIG. 23). Furthermore, hESC lost the ability to form a teratoma at a specific cell dose (10-25K cells injected; FIG. 2h; R2=06002), whereas v-hESC-1 did not (FIG. 2i; R2=0.9818).

Figure 24:
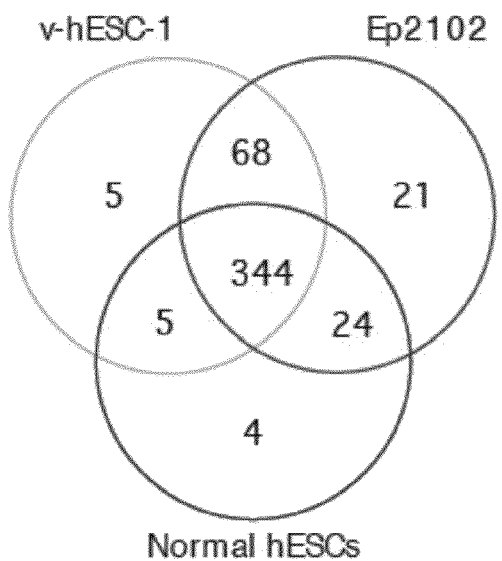
FIG. 24 shows a Venn diagram of all commonly expressed genes between v-hESCs, hESCs and EP2102. The non-overlapping nodes of the Venn are genes that are unchanging in the represented cell type versus all other samples. Note that v-hESCs are molecularly more similar to EP2102 cells. Data is representative of 2 experimental replicates.

Teratocarcinomas are defined as containing both somatic tissues and undifferentiated malignant embryonal carcinoma cells (21,22). Teratomas generated by hESC showed no evidence of Oct4 staining, whereas v-hESC-1 teratomas contained discrete regions of Oct4+ cells, demonstrating the presence of undifferentiated hES cells (FIG. 2j). To investigate the malignant potential of variant hES cells, the applicants examined several tissues prone to retention of metastatic cells, including lung, spleen, liver, brain and kidney, as well as other sites throughout the body. No metastases were detected from teratomas produced by either hESC or both variant lines (FIG. 26). Although v-hESC-1 cells migrated faster than hESC cells in three-dimensional collagen gels (FIG. 2k), their inability to metastasize in vivo suggests that they are not malignant. Finally, microarray analysis of 440 genes known to be associated with cancer revealed that v-hESC-1 cells are molecularly more similar to EP2102 cells than to normal hES cells (FIG. 24) Taken together, these data suggest that variant hES cells lie between normal hES cells and embryonal carcinoma cells but are not malignant based on lack of in vivo metastatic ability.

Enhanced TIC frequency in variant hES cells may be related to the loss of the surrounding fibroblast-like cells, which function as a regulatory niche (18). Fibroblast growth factor receptor (FGFR)1 is expressed exclusively in the fibroblast-like cells, whereas insulin-like growth factor 1 receptor (IGF1R) is expressed exclusively in the hES cells (18) (FIG. 3a). In contrast, v-hESC-1 co-expressed FGFR1 and IGF1R, in a manner similar to teratocarcinoma EP2102 cells (FIG. 3a-c). These results suggest that although variant hES cells acquire independence from the regulatory niche, they compensate molecularly by expressing FGFR1. Coexpression of IGFR1 and FGFR1 may be a general feature of partially transformed hES cells.

Figure 25:
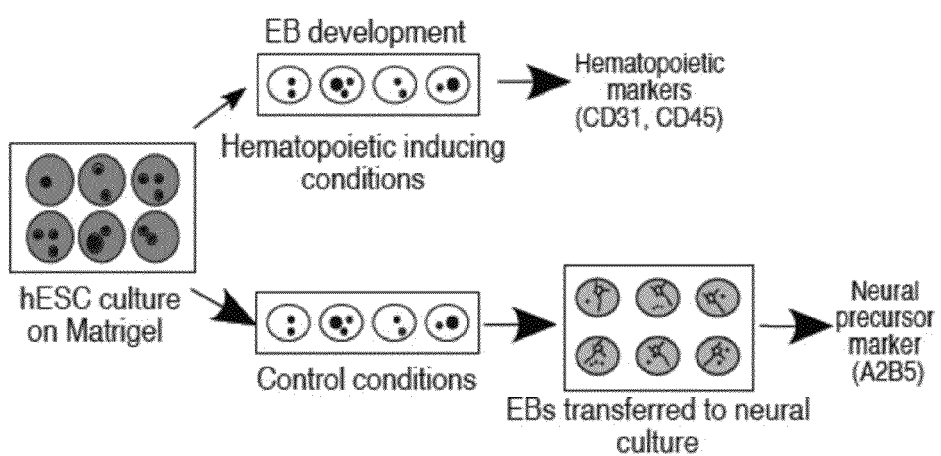
FIG. 25 shows a schematic depicting EB differentiation experiments over 15 days in hematopoietic inducing conditions and neural culture.

The Applicants also examined differentiation in vitro. Embryoid bodies (EBs) were formed from dissociated hESC and v-hESC-1 cells and cultured in either hematopoietic or neural conditions (FIG. 25). After 15 d in hematopoietic culture, expression of CD45 in v-hESC-1 EBs was 415-fold less than in hESC EBs (N=3 independent trials, P<0.01) (FIG. 3d-f). The proportion of CD31+CD45− hematopoietic precursors was also reduced (FIG. 3d-e). Similar results were obtained after 18 d (FIG. 3e,f) and 23 d (data not shown) of culture. Thus, the hematopoietic potential of v-hESC-1 is sharply reduced.

hESC EBs cultured in neural conditions showed features typical of neuronal morphology in addition to flat cells with many small extensions (FIG. 3g). In contrast, v-hESC-1 displayed neural-like rosettes amid a very dense cell population (FIG. 3g). hESC EBs stained more intensely for the neural precursor marker A2B5 compared with v-hESC-1 EBs, and this was confirmed by flow cytometry (hESC EBs: 39.3±6.3% and v-hESC-1 EBs: 20.4±4.2%; N 1/4 6, P<0.05) (FIG. 3g,h). A2B5+ cells were also significantly lower in v-hESC-1 EBs despite an overall significant increase in bulk culture total cell number in neural precursor cultures (FIG. 3i).

The EB experiments suggested that v-hESC-1 EBs exhibit aberrant differentiation, consistent with the more primitive features seen in vivo, and are therefore not superior hES cells. The Applicants tested the hypothesis that variant hES cells resist exit from the undifferentiated state by examining Oct 4 and SSEA3 expression in EBs in hematopoietic culture over 15 d (FIG. 3j,k). Oct4 and SSEA3 are believed to activate genes important to the pluripotent state while repressing genes associated with lineage specification and differentiation (23-25). During the first 10 d, SSEA3 was significantly higher in v-hESC-1 EBs than in hESC EBs (N=3, P<0.05 or P<0.01) (FIG. 3j). However, by day 15, the difference was not significant. Normalization relative to undifferentiated controls showed that adjusted SSEA3 levels in hESC declined more rapidly during the first 7 d (FIG. 3j). Oct4 was significantly higher in v-hESC-1 EBs only for the first 4 d of differentiation and, similar to SSEA3, was identical to that in hESC after 15 d (N=3, P<0.05 or P<0.01) (FIG. 3k). Normalization showed a nearly identical rate of decline of Oct4 levels in hESC and v-hESC-1 (FIG. 3k).

Figure 4:
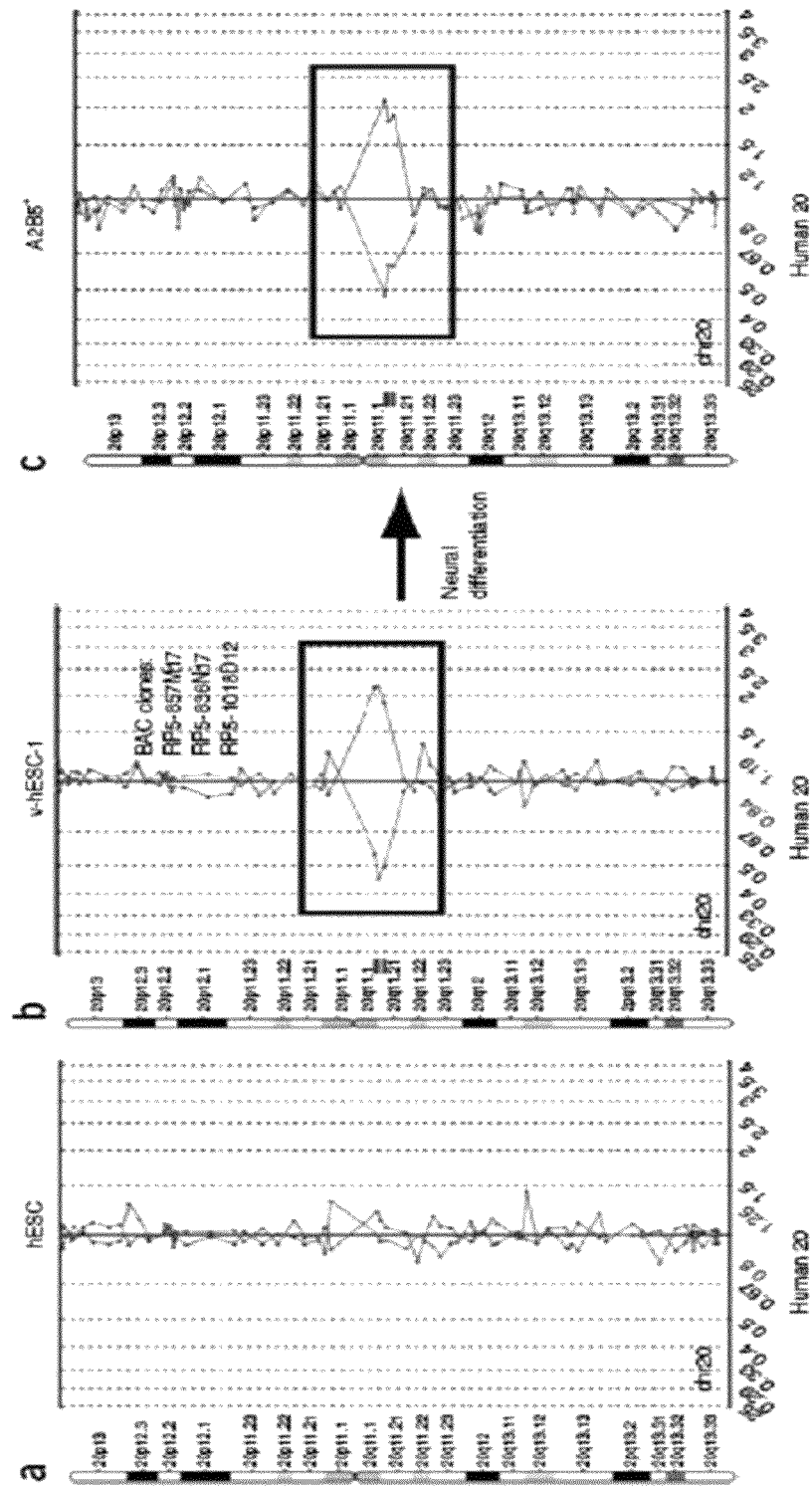
FIG. 4 shows neural progeny of variant hES cells retain molecular and functional abnormalities of their parent cells. (a-c) aCGH analysis of undifferentiated hES cells (a), v-hESC-1 (b) and variant hES cell A2B5+ cells (c) for chromosome 20. Box: significant gain at 20q11.1-11.2. Region is defined by 3 BAC clones: RP5-857M17, RP5-836N17, RP5-1018D12. (d-f) Representative dot plots of BrdU incorporation and DNA content of normal hESC A2B5+ (d), variant hES cell A2B5+(e) and undifferentiated variant hES cell (f) cell populations. (g) Quantification of normal hESC and variant hES cell A2B5+ cell cycle properties. Error bars, s.e.m. (h) Immunocytochemical analysis of Oct4 (red) (left) and Nanog (red) (right) in 48 h sorted A2B5+ variant hES cell populations. Nuclei were stained with DAPI (blue). Insets: isotype control (left), brightfield image of A2B5+ cells (right). Scale bar, 100 µm. Arrow indicates a Nanog-positive cell. (i-k) Histological analysis of noninjected versus v-hESC-2 neural precursor injection site—H&E stain of fat cells in the noninjected side (i), representative image of NOD-SCID b2 mouse depicting noninjected side and injection site (j) and H&E staining of tumor core (k). Arrows indicate well-defined tumor-host border. Scale bar, 500 µm. (b-n) Ki67 staining in noninjected fat tissue (l), representative tumor core (m) and positive-control intestinal crypt cells (n). Arrow in (m) indicates representative Ki67+ cell. Arrow in (n) indicates direction of differentiation in intestinal crypts. Note diminished staining with differentiation. Insets: (m-n) negative controls. Scale bars, 200 µm.
Figure 4:
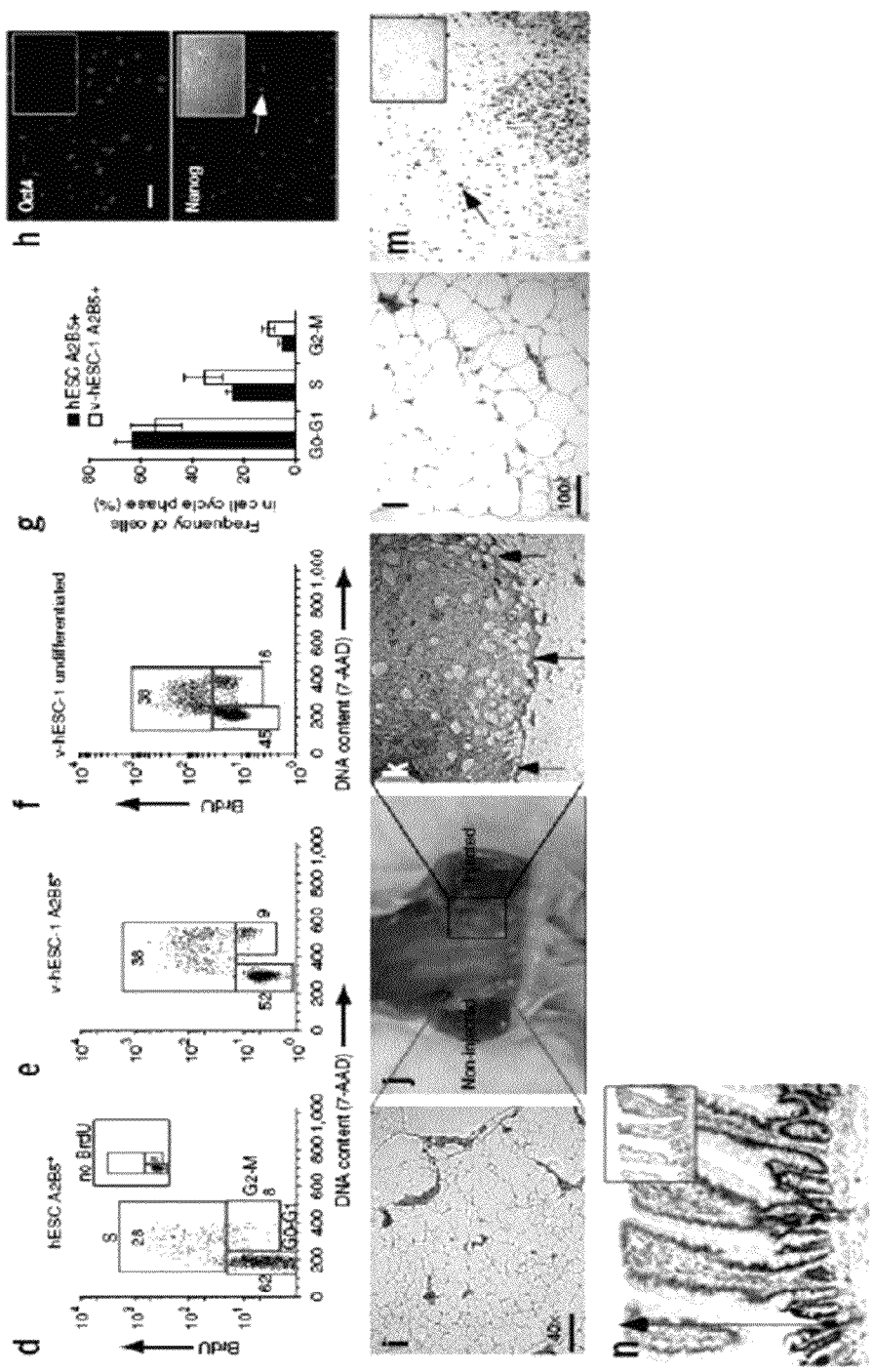

The Applicants used array comparative genomic hybridization (aCGH) to search for DNA sequence copy number variations undetectable by standard cytogenetic assays. V-hESC-1 showed an amplification of at least 0.8 megabase at 20q11.1-11.2 (FIG. 4a,b). Amplifications at 20q in hES cells have been described previously (9,26,27). V-hESC-2 exhibited a small deletion at 5q34a-5q34b;5q3 and a gain of chromosome 12 in a significant sub-population of cells, indicative of a mosaic culture (data not shown). Gain of chromosome 12 in hES cells has also been reported (6-8). The lack of a chromosome 20q amplification in v-hESC-2 confirms that this subclone is independent of v-hESC-1.

The identification of discrete chromosomal changes such as the 20q11.1-11.2 amplification allows for clonal tracking of specific cell populations in heterogeneous differentiated cultures. v-hESC-1 progeny in neural conditions (both A2B5+ and A2B5− cells) exhibited this amplification (FIG. 4c and data not shown), supporting the hypothesis that hES cells in the process of transformation are not selected out of the culture during differentiation. Analysis of A2B5+ neural progenitor cells by BrdU incorporation (FIG. 4d-g) showed a higher fraction of v-hESC-1-derived neural precursor cells in S phase compared with neural precursors derived from normal hES cells (35±7.1% versus 24.0±2.4%, N=3 for each) (FIG. 4d-g). The fraction of v-hESC-1-derived cells in S phase was similar to that of their undifferentiated parent cells, suggesting that the cell-cycle properties of v-hESC-1 are inherited by differentiated neural progeny (FIG. 4d,f). A2B5+ cells derived from variant hES cells were also isolated using stringent sorting gates (495% purity, data not shown) and were cultured for 48 h. These cells did not appear to contain undifferentiated pluripotent cells, as confirmed by undetectable Oct4 and Nanog expression (FIG. 4h).

To test whether these rapidly cycling cultures of differentiated cells could form tumors in vivo, the Applicants injected v-hESC-1-derived neural precursors subcutaneously into nonobese diabetic severe combined immunodeficient (NOD-SCID) mice. Tumor growth was evident at the injection site after 8 weeks and exhibited a well-defined tumor-host interface; only differentiated fat cells were evident in the noninjected site (N=3) (FIG. 4i-k). Histological analysis revealed no evidence of pluripotency as indicated by a lack of tissues from all 3 germ layers, confirming that the tumors were not teratomas (FIG. 4i-k). However, many cells in the tumor core were Ki67-positive, demonstrating that these cells were not quiescent and remained cycling in vivo. Taken together, these results suggest that v-hESC-1 neural progenitors are incapable of overcoming the altered cell-cycle properties of their parents, and this likely contributes to the maintained tumorigenic capacity in vivo (FIG. 4l-n).

The present Example suggests that functional assays are required to distinguish normal hES cells from those that have undergone some degree of neoplastic progression. Without such functional assays, partially transformed hES cells may be mistaken for superior hES cells with enhanced 'sternness'. The chromosomal abnormalities detected here and in previous studies have not been proven to promote transformation and thus far cannot be used as markers of hES cells undergoing transformation. The wide distribution of protein markers on multiple cancer stem cell populations, normal stem cells and even differentiated epithelium demonstrates the lack of specificity of immunophenotyping for detecting these aberrant cells (28-31).

A functional approach has revealed self-renewal and differentiation parameters that identify hES cells with some features of transformation. The functional changes observed may arise from the chromosomal changes or from unidentified genetic or epigenetic alterations. Variant hES cells appear to be intermediate between normal hES cells and malignant embryonal carcinoma cells. As they did not form metastases in vivo, they are not malignant. The results presented in this Example also suggest that neural differentiation of variant hES cells does not alter cell-cycle and self-renewal properties. To the Applicants knowledge, previous studies have not examined whether transformation-associated properties that provide a selective advantage to undifferentiated cells persist in differentiated progeny.

Methods hes Cell Culture and bFGF Depletion. H9 hESC and v-hESC lines were maintained as previously described (33). Briefly, cells were cultured on Matrigel (BD Biosciences) in MEF-CM supplemented with 8 ng/ml basic fibroblast growth factor (bFGF). After 4 (variant hES cells) or 7 (normal hES cells) d, cultures were dissociated for 5 min in collagenase IV (Gibco) and passaged 1:6 (variant hES cells) or 1:2 (hES cells). Normal hES and variant hES cells were stained for Oct4, SSEA3, SSEA4, IGF1R and/or FGFR1 and phenotype was analyzed either by flow cytometry or immunocytochemistry. For bFGF experiments, cultures were maintained in control 8 ng/ml bFGF conditions or 4 ng/ml, 2 ng/ml or 0 ng/ml bFGF for 20-28 d.

Limiting Dilution Teratoma Formation, Neural Precursor Injections and Histology. Undifferentiated hES cells and variant hES cells were treated with collagenase IV for 5-10 min as described above and resuspended in PBS/3% FBS. Different cell numbers were injected intratesticularly into male NOD-SCID mice. Mice were killed 6 weeks after initial injection. Teratomas were extracted, embedded in paraffin and sectioned in 5 mm intervals followed by deparaffinization in xylene and processing through a graded series of alcohol concentrations. Samples were stained with hematoxylin and eosin or Oct4 followed by dehydration and xylene treatment. Slides were mounted using Permount and imaged using a standard light microscope at 200 and 400 magnification. Tissue was also collected from a variety of organs including lung, spleen, liver, brain and kidney to investigate the presence of metastatic cells. Normal hES and variant hES aggregates were also tested for their migratory capacity in collagen gels.

For variant hES cell neural precursor injections, NOD-SCID b2 mice were injected subcutaneously with a mixture of $1.0 \times 10^6$ cells from bulk neural precursor cultures and 1:15 Matrigel. Mice were killed 8 weeks after initial injection, and tumors were extracted, embedded in paraffin and prepared for analysis as stated above. Sections were also stained for Ki67 (1:200) (MEDICORP) to detect cycling cells after antigen retrieval with 10 mM citrate buffer, pH 6.0. A dilutent-only sample was used as a negative control and intestinal crypt tissue was used as a positive control for Ki67 staining.

Array Comparative Genomic Hybridization. Specimen and control DNA concentrations were measured on a Hoefer Dynaquant Fluorometer (Hofer) or the NanoDrop ND-1000 (NanoDrop). The concentrations were standardized by taking measurements of known concentrations of calf thymus DNA and male and femalegDNA (Promega) and adjusting the concentration value of the specimen DNA appropriately.

For each specimen and reference sample 1 mg of DNA was measured by concentration/volume. Sex mismatch forward-reverse experiments were used to provide a one-copy gain/loss of the X chromosome for reference within the experiment. The DNA was denatured for 5 min in a dry bath at 100 1 C, and then cooled on ice for 5 min. An admixture was created to a volume of 10 ml/sample that contained: dNTPs (Invitrogen), Cyanine 3- or Cyanine 5-labeled dCTP (PerkinElmer), and Klenow fragment (Invitrogen). A 5 ml aliquot of this mix was pipetted into the DNA containing sample tubes; this mixture was incubated for 1 h in a water bath at 37 C. After the first labeling period, the heating and cooling steps were repeated as above, and 5 more ml of the admixture was added to the sample tubes, and they were returned to the 37 C water bath for another hour. At the end of the second labeling period the reaction was stopped by the addition of 5 ml of 0.5 M EDTA and heating to 70 C for 10 min. The entire contents of the reference sample tubes were then transferred into the corresponding sample tubes. The labeled DNA was precipitated by adding 45 ml of Hybl buffer (PerkinElmer), 12.9 ml of 5 M NaCl and 130 ml of 100% isopropanol; the mixture was then vortexed. Tubes were held in the dark for 20 min and then centrifuged at 16,000 g for 20 min. After centrifugation, tubes were checked for pelleted DNA, the isopropanol decanted and 500 ml of 70% ethanol was used to rinse the pellets followed by another 5 min of centrifugation. The ethanol was removed by light suction and the pellets were allowed to completely dry in the dark for ~10 min. DNA pellets were rehydrated with 10 ml of distilled, deionized water and incubated at 37 1 C to solubilize the pellet. Non-specific sequences were prehybridized and blocked by the addition of 30 ml of HybII buffer to each tube. The tubes were gently mixed, briefly centrifuged and incubated at 70 C for 10 min to denature the mixture; this was followed by a further incubation at 37 C for a half an hour. The entire hybridization mixture was then pipetted onto a SpectralChip 2,600 array slide containing 2,605 nonoverlapping BAC clones spanning the genome at approximately 1-Mb intervals spotted in duplicate on glass slides, covered with a 22×60 mm cover slip, sealed in a hybridization chamber (Corning) and hybridized at 37 C.

After 16 h, the chambers and slides were removed from the hybridization oven. The coverslips were removed by soaking the slides in warm (37 C) 0.5% SDS/2×SSC. The slides were then washed sequentially at 50 1 C in 2×SSC solutions containing 50% formamide and then 0.1% Igepal. The final wash consisted of 0.2×SSC alone. Slides were then rinsed twice in fresh dionized water and dried with a stream of compressed nitrogen gas. Arrays were then scanned on a ScanArray Gx Plus microarray scanner (PerkinElmer) or the Genepix 4000B scanner (Molecular Devices) and analyzed with SpectralWare 2.2.4 (PerkinElmer).

In addition to aCGH analysis, potential chromosomal abnormalities were also assessed by spectral karyotyping (SKY), Interphase FISH and G-banding.

Sorting of Variant hES Cell Neural Precursor Cultures for aCGH Analysis. EBs were formed from normal hES and variant hES cells and cultured in neural conditions. EBs in neural proliferation medium were trypsinized after 4 d in culture and stained with the cell surface marker A2B5 (R&D Systems). Cells were visualized using Alexa Fluor 647 goat antimouse IgM m chain (Molecular Probes, Invitrogen), and the single cell suspension was then filtered through a 40-mm strainer to remove any remaining aggregates. Cells were sorted based on A2B5 expression using a FACS Aria sorter (BD Biosciences), and collected A2B5+ and A2B5− cells were centrifuged and prepared for DNA extraction using the AllPrep DNA/RNA Mini Kit (Qiagen).

Cell Cycle Analysis. For BrdU experiments, day 8 normal hES cell and variant hES cell neural precursor cultures were exposed 1 h with 10 mM BrdU before cell harvest. Single cell suspensions were then stained for A2B5 using goat anti-mouse-IgM Alexa-488 (Molecular Probes, Invitrogen) as secondary antibody and then fixed in ethanol 70% after PBS/FBS 3% wash. Detailed protocols are as described (17). To further assess proliferation of normal hES and variant hES cells, metaphase spreads suitable for karyotyping were also used to score for mitotic index.

Statistical Analysis. All tests were performed using InStat Version 3.0a statistical software (GraphPad Software). Descriptive statistics including mean and s.e.m. along with one-way ANOVAs, independent sample two-tailed t-tests, and Tukey's test for multiple comparisons were used to determine significant differences. $P<0.05$ was considered significant.

Mitotic Index. Normal hESC and v-hESC-1 and v-hESC-2 cultures were dissociated for 5 min in collagenase IV (Gibco). Cultures were rinsed 2× in PBS and filtered through a 0.22 μm filter. Suitable metaphase spreads were prepared and the percentage of cells in metaphase relative to the total number analyzed was scored for mitotic index.

Oncoarrays. Microarray analysis of gene expression Total RNA was extracted from frozen normal hESC, vhESC, EP2102 pellets using the RNeasy kit (Qiagen). Amplified RNA was labeled with the TrueLabeling-AMP™ 2.0 kit, and hybridized to the Oligo GEArray® Human Cancer Microarray (SuperArray Bioscience Corp.). Background levels of hybridization were subtracted, and gene expression was normalized to values obtained for hESCs.

Oct4 Staining in Teratomas. Normal hESC and v-hESC-1 tumors were extracted, embedded in paraffin and prepared for analysis. Sections were also stained for Oct4 (1:200) overnight at 4° C. (Cell Signaling Technology) to detect pluripotent cells following antigen retrieval with 10 mM citrate buffer, pH 6.0. A diluent-only sample and noninjected mouse testicular tissue were used as negative controls.

Immunocytochemistry. Cultures were stained for SSEA3 and Oct4 as previously described (Stewart, M. H. et al. Clonal isolation of hESCs reveals heterogeneity within the pluripotent stem cell compartment. *Nature Methods* 3, 807-815 (2006). Briefly, approximately $5\times10^4$ were cultured for 2-3 days on chamber slides coated with Matrigel (BD Biosciences) and maintained as described above. Cells were stained with SSEA3, fixed in paraformaldehyde and permeabilized in Triton X-100 prior to staining for human Oct4 (N-19) (Santa Cruz Biotechnology). Cells were visualized with Alexa Fluor 594 rabbit anti-mouse IgG (Molecular Probes) and Alexa Fluor 488 rabbit anti-goat IgG (Molecular Probes) secondary antibodies. Chamber slides were mounted and counterstained with Vectashield Mounting Medium containing DAPI (Vector Labs).

Cultures were stained for IGF1R and FGFR1 as described previously (Bendall, S. C. et al. IGF and FGF cooperatively establish the regulatory stem cell niche of pluripotent human cells in vitro. *Nature* 448, 1015-21 (2007)). Briefly, cells were rinsed twice with PBS and then fixed in 4% paraformaldehyde. Samples were stained with 10 μg ml-1 chicken anti-IGF1R (Abcam ab32823) and 2 μg ml-1 mouse anti-FGFR1 clone VBS1 (Chemicon MAB125). Cells were incubated with primary antibodies followed by secondary detection with Alexa Fluor 488 goat anti-mouse IgM (Molecular Probes) or Alexa Fluor 594 goat anti-chicken IgG (Molecular Probes) at 3 μg ml-1.

EB Formation, Hematopoietic and Neural Precursor Differentiation. Embryoid bodies (EBs) were formed from hESCs and v-hESCs as previously described (Chadwick, K. et al. Cytokines and BMP-4 promote hematopoietic differentiation of human embryonic stem cells. Blood 102, 906-915 (2003). Wang, L. et al. Endothelial and hematopoietic cell fate of human embryonic stem cells originates from primitive endothelium with hemangioblastic properties. Immunity 21, 31-41 (2004)). Cultures were treated with collagenase IV on the day of passage and scraped off the Matrigel-coated plate in strips. Cells were transferred to low attachment 6-well plates in differentiation medium consisting of 80% knockout DMEM (KO-DMEM) (Gibco), 20% non-heat inactivated fetal calf serum (FCS) (HiClone), 1% nonessential amino acids, 1 mM L-glutamine, and 0.1 mM R-mercaptoethanol. Cultures were replaced with fresh differentiation medium or medium supplemented with 50 ng/ml BMP-4 (R&D Systems), 300 ng/ml stem cell factor (SCF) (Amgen), and 300 ng/ml Flt-3 ligand (R&D Systems). EBs were maintained for 15 days, and medium was changed every 4 days.

For neural precursor differentiation, EBs cultured in EB medium alone for 4 days were transferred to 12-well plates coated with poly-L-lysine/fibronectin in neural proliferation medium consisting of DMEM/F12 with B27 and N2 supplements (Gibco), 10 ng/ml bFGF, 10 ng/ml human epidermal growth factor (hEGF), 1 ng/ml human platelet derived growth factor-AA (PDGF-AA) (R&D Systems), and 1 ng/ml human insulin-like growth factor-1 (hIGF-1) (R&D systems) (Carpenter, M. K. et al. Enrichment of neurons and neural precursors from human embryonic stem cells. Experimental Neurology 172, 383-397 (2001). Cultures were allowed to adhere to the plates and expand as a monolayer over 4 days.

Flow Cytometry. hESCs and v-hESCs were treated with collagenase IV, and then placed in cell dissociation buffer for 10 minutes at 37° C. (Gibco). Cell suspensions were stained with SSEA3 (Developmental Studies Hybridoma Bank, mAB clone MC-631, University of Iowa, Iowa City, Iowa), SSEA4 (Developmental Studies Hybridoma Bank, mAB clone MC-813-70). Cells were visualized with Alexa Fluor 488 goat anti-rat IgM (Molecular Probes, Invitrogen) or goat anti-mouse IgG-FITC secondary antibody (Immunotech). Appropriate negative controls were utilized. Live cells were identified by 7-Amino Actinomycin (7AAD) exclusion and then analyzed for cell surface marker expression using the FACS Calibur (BDIS). Collected events were analyzed using FlowJo 6.4.1 Software (Tree Star Inc.).

For EB experiments, cells were treated with collagenase B for two hours prior to treatment with cell dissociation buffer. Cultures were resuspended in PBS+3% FBS and filtered through a 0.4 µm filter and prepared for flow cytometry as described above. EBs were stained for SSEA3 and Oct4 expression on days 2, 4, 7, 10 and 15. For hematopoietic differentiation, cultures were stained at day 15, day 18 and day 23 for v-hESCs with the fluorochrome-conjugated antibodies, CD31-PE (Becton Dickinson Immunocytometry Systems (BDIS)), and CD45-APC (Miltenyi) or the corresponding isotype controls. Embryoid bodies in neural proliferation medium were trypsinized after 4 days in culture and stained with the cell surface marker A2B5 (R&D Systems). Cells were visualized using Alexa Fluor 488 goat anti-mouse IgM µ chain (Molecular Probes, Invitrogen).

Cell Migration Assay. Individual dissociated hESC and v-hESC aggregates were implanted into 4-well culture dishes containing 500 µl aliquots of a 3.0 mg/ml collagen type I solution (Vitrogen 100) (COHESION) as described (a gift from Dr. Rolando Del Maestro, Montreal Neurological Institute, McGill University) (Werbowetski, T., Bjerkvig, R. & Del Maestro, R. F. Evidence for a secreted chemorepellent that directs glioma cell invasion. J Neurobiol 60, 71-88 (2004)). After gelling at 37° C. for 40 min, the gel was overlaid with MEF-CM supplemented with 8 ng/ml bFGF. Cell migration was assessed daily using an inverted phase contrast microscope. Total migration distance was calculated each day from the centre of the aggregate to the population of the migrating cells most distant from the aggregate. The original radius was subtracted from these values and measurements were taken for 7 days.

Spectral Karyotyping. Eleven milliliters of 37° C. 0.075M KCl were added to each cell suspension followed by incubation at 37° C. for 20 min. The samples were centrifuged at 200 g for 8 min, fixed in 10 ml of ice cold 3:1 methanol/acetic acid fix and incubated at room temperature for 15 min. Centrifugation and fixation were repeated. Samples were centrifuged at 2000 rpm for 7 min and the cells were resuspended in 5 ml fresh 3:1 methanol/acetic acid. Fixed cell suspensions were dropped onto acid cleaned slides in a Hanabi® metaphase spread maker and examined to determine quality of the chromosome spreads and the mitotic index. Slides were aged overnight at 37° C. in a dry oven prior to preparation. The slides were treated with pepsin solution for 3 min at 37° C., washed twice in PBS followed by 1×PBS/MgCl2 at room temperature. Slides were then placed in a 1% formaldehyde solution, incubated 10 min at room temperature and washed once in 1×PBS. SkyPaint mixture (10 µl) was denatured by incubating at 80° C. for 7 min, and then 37° C. for 90 min. The slides were incubated in 2×SSC at 70° C. for 30 min, and then allowed to cool. Slides were washed once in 0.1×SSC and denatured in 0.07M NaOH at room temperature for 1 min. The slides were washed at 4° C. and dehydrated in an ethanol series at −20° C., and allowed to air dry. The denatured SkyPaint® was added and the slides were incubated in a humidified chamber at 37° C. for 24 hours. Following hybridization, the slides were washed in 0.5×SSC at 72° C. for 5 min. Slides were then washed once in 4×SSC/0.1% Tween 20 at room temperature. Blocking reagent (80 µl) was applied and the slides were incubated for 30 min at 37° C. Slides ere stained with Cy5 and incubated at 37° C. for 45 min. The slides were then washed three times in 4×SSC/0.1% Tween 20 at 45° C. Slides were then stained with Cy5.5 staining reagent and incubated at 37° C. for 40 min. The slides were washed three times in 4×SSC/0.1% Tween 20. The slides were finally washed in distilled water to remove detergent residue and allowed to air dry. Once the slides were fully dry, 15 µl DAPI/Antifade solution was applied to each slide and a 22×22 mm glass coverslip was placed over the cell spreads. The SKY slides were scored using the Spectracube® system (Applied Spectral Imaging). Suitable metaphases were assessed with a DAPI filter. Image acquisition is based on a spectral imaging system using an interferometer and a CCD camera. Band and spectral images were used to determine the karyotype of each cell, with SkyView EXPO™ image analysis software. A minimum of 100 suitable metaphases was scored for each cell line.

Interphase FISH. Interphase FISH was performed using the Vysis (Des Plaines) Chromosome Enumeration Probes (CEP)® for chromosomes X (Spectrum Green®), 13 (Spectrum Orange®), 18 (Spectrum Orange®) and 21 (Spectrum Aqua®) according to manufacturer guidelines. Briefly, hESCs and v-hESCs were fixed with the standard 3:1 methanol/acetic acid fix and dropped onto acid washed slides as stated above. Seven microliters of CEP hybridization buffer was mixed with 1 µl CEP DNA probe and 2 µl distilled $H_2O$ and samples were heated in a 73° C. water bath for 5 min. Slides were denatured in 70% formamide/2×SSC solution for 5 min at 73° C., followed by dehydration in an ethanol series (70%, 85% and 100%), 1 min each.

Slides were then dried and placed on a 50° C. slide warmer for 2 min. Each slide was mixed with 10 µl of the probe mixture and then placed in a 42° C. dry incubator for 60 min. Immediately following, slides were placed in a coplin jar containing 0.4×SSC/0.3% NP-40 at 73° C., agitated for 3 sec and then left in wash for 2 min, followed by a second wash in 2×SSC/0.1% NP-40 at room temperature for 1 min (agitating for 3 sec as the slide was placed in the bath). Slides were then allowed to air dry in the dark. DAPI II counterstain (10 µl) was added to each slide, and slides were then viewed with appropriate filter sets to determine the number of copies of each of the chromosomes. Cells from normal human amniotic fluid samples were used as procedural and analytical controls.

Giemsa Staining. Dropped slides were aged at 56° C. for 48 hours in a dry oven, and then cooled at room temperature. Slides were rinsed in 0.15 mol/l KCl, and immersed in a 2-4% (v/v) trypsin to 0.15 mol/l NaCl for 5-30 seconds and then rinsed 2× in 0.15 mol/l KCl. Samples were stained with Giemsa solution (8% v/v Giemsa to 6.86 pH phosphate buffer) for 45-80 seconds. Slides were 3× in ddH20 and placed on a slide warmer for drying.

Accession Codes. Gene expression and aCGH datasets have been deposited at GEO with accession no. GSE13995.

Example 2

Screening Methods and Assays that Use Transformed Pluripotent Stem Cells

In this example, the Applicants demonstrate the use of transformed pluripotent stem cells in cell-based screening assays. In some embodiments, the t-hPSCs are used in High Throughput Screening (HTS) assays and optionally for drug discovery.

The Applicants describe assays that use the t-hPSCs described herein for determining loss of pluripotency/differentiation. In particular, EOS OCT4 reporter v-hESC-1 cell lines have been generated and tested in a high throughput format.

The Applicants also describe the use of t-hPSCs in assays to for determining apoptotic or anti-cancer activity of a compound, composition or reagent in brought into contact with t-hPSCs.

A person skilled in the art will appreciate that the methods and assays described herein may also use derivatives of the t-hPSCs cell lines described herein created by means of spontaneous or induced differentiation.

Transformed Pluripotent Stem Cells are Ideal Candidates for HTS

Transformed pluripotent stem cells can be seeded as single cells and are able to recover at a much higher rate after passaging than non-transformed human stem cells which must be passaged as clusters.

Here, the Applicants demonstrate that when non-transformed human pluripotent stem cells are plated as single cells, colony formation and growth is delayed with colonies only reaching minimum assay mass at around 150 hrs post seeding. On the other hand, transformed human pluripotent stem cells plated as single cells show growth rates comparable to non-transformed stem cells plated as clusters. The rapid growth of transformed stem cells allows for cellular assays to be performed as early as 24 hrs after seeding, avoiding unnecessary use of reagents (during growth phase) and automation "wait times".

FIG. 5 shows the kinetics of pluripotent stem cell colony growth measured by the colony area. Normal pluripotent stem cells were seeded as clusters or single cells. Note that with cluster seeding colonies are detected 24 h of seeded and continue to increase during the culture period. In contrast, colonies from single cell seeded wells are only detected at 144 h and have delayed colony growth until after 264 h. Colonies from transformed cells seeded as single cells follow the same recovery pattern as normal cells seeded as clusters.

The Applicants have also shown that after single cell plating of transformed human stem cells, the cells grow in a much more uniform pattern than their normal stem cell counterparts seeded as clusters, reducing inter-well variability which compromises HTS data interpretation. Normal pluripotent stem cells were incubated with collagenase IV for 10 min before being scraped off and broken into clusters. The clusters were then seeded in the wells of matrigel coated 96 well microtitre plates. Transformed pluripotent stem cells were detached following trypsin incubation and divided into single cells by gently pipetting the suspension and filtering through a 40 um cell strainer. The single cell suspension was then seeded into the wells of matrigel coated microtitre plates. Following 6 days of culture, images of the colonies arising from normal cells and the monolayer of transformed stem cells were acquired. FIG. 6 shows the cluster seeding of normal stem cells versus single cell seeding of transformed stem cells. Note the inter-well variation in colony shape, location and numbers in cluster seeded wells (outlined in the top two panels) compared to the homogeneous cell monolayer that develops with transformed stem cells (lower two panels).

HTS Screening of t-hPSCs for Loss of Pluripotency

Pluripotent stem cells express a collection of surface and intracellular markers named pluripotency markers. Analysis of pluripotency markers is key for the assessment of differentiation during which cells lose the expression of pluripotency markers and gain expression of lineage specific markers. Loss of pluripotency can be studied by multiple means including antibody recognition/immunofluorescence, morphological profiling, and lastly, the use of reporter cell lines.

The Applicants have generated and validated the transformed stem cells lines described herein with Early transposon promoter Oct-4, Sox2 and Nanog enhancers (EOS) lentiviral vector reporters coupled to green fluorescent protein (GFP) (Hotta et al. Nat Methods 2009 6(5):370-376) for use in screening assays.

The versatility of transformed human pluripotent stem cells is illustrated by the multiple types of assays that it enables. For example, transformed pluripotent stem cells were passaged as single cells using Trypsin and seeded at 1000 cells per well into 96 well optical imaging plates coated with Matrigel® containing 100 ul mouse embryonic fibroblast conditioned media (MEF-CM). Plates were incubated at 37 degrees for 24 Hr before treatment with bone morphogenic protein 4 (BMP4) commenced. Cells were treated with either 1 ng/mL, 10 ng/mL, 100 ng/mL, or 0 ng/mL BMP4 for 4 days (n=3). After 4 days cells were fixed with 2% paraformaldehyde and stained with Oct4-Alexa 647 antibody. Cells were loaded into a plate reader and measured at excitation emission pairs of 650/665 and 488/520 nm to measure Oct4-Alexa 647 antibody (FIG. 7 top graph) and GFP (FIG. 7 bottom graph) respectively. Pluripotency (measured by the loss of OCT4 and GFP expression) decreased with the increase in differentiation inducing compound BMP4. Similar results were obtained when other compounds were tested.

Accordingly, FIG. 7 shows the monitoring and High Throughput Screening of GFP expression levels using a high throughput plate reader with the t-hPSC cells described herein. High Throughput Screening of stem cells was not previously readily possible due to the lack of reproducible cell passaging methods (low inter-well variation) and cell culture homogeneity.

Screening Assays for Identification of Compounds that Result in a Loss of Pluripotency or that Induce Differentiation Loss of pluripotency is required for differentiation of stem cells. Cells that loose pluripotency quickly differentiate towards multiple cell lineages. Identification of compounds that induce differentiation through stem cell based screening constitutes a unique approach for the discovery of compounds of chemicals that can be used for in vitro or in vivo differentiation generating specialized cells to be used as experimental tools, cells for replacement therapy or optionally to be made into a drug that induces endogenous repair of damaged tissues.

Figure 8:
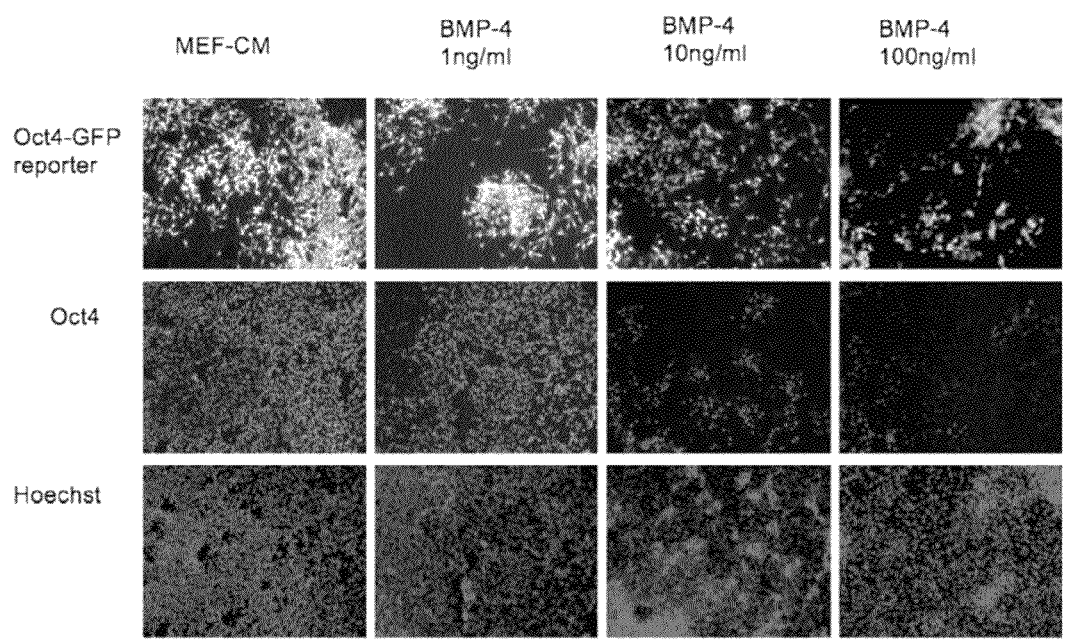
FIG. 8 shows transformed pluripotent stem cells that contain an Oct4-GFP reporter treated with BMP-4. Transformed pluripotent stem cells that contain an Oct4-GFP reporter were plated, cultured, treated with BMP-4 and fixed as described in FIG. 7. Cells were permeabilized with 0.1% TritonX-100 and stained with Oct4 antibody conjugated with Alexa 647. The cell nuclei were stained with Hoechst 33342. Images were collected using 10× objective on Olympus microscope, and analysed using Image-Pro Plus software.

FIG. 8 shows transformed pluripotent stem cells that contain an Oct4-GFP reporter that were plated, cultured, treated with BMP-4 and fixed as described above with respect to FIG. 7. Cells were permeabilized with 0.1% TritonX-100 and stained with Oct4 antibody conjugated with Alexa 647. The cell nuclei were stained with Hoechst 33342. Images were collected using 10× objective on Olympus microscope, and analysed using Image-Pro Plus software. As shown in FIG. 8, treatment of the cells with increased amounts of BMP-4 resulted in decreased Oct-4 antibody staining as well as decreased GFP fluorescence.

Transformed Pluripotent Stem Cells are Suitable for Screening of Cells with Automated Image Analysis Stem cells have a great potential for use in drug screening due to their unique properties of self-renewal and differentiation; however they continue to be underutilized by the Industry due to their complexity, low predictability and reproducibility. The intrinsic complexity of stem cells has led the field to adopt High Content screening as a way the only feasible approach to analyse these cells. High Content Screening is a multi-parametric image based approach, which is highly dependent on equipment and software development. To date very little equipment and software exist capable of segregating normal stem cells grown in culture, consequently the data generated is inaccurate. The use of transformed stem cells described herein overcomes this limitation by enabling stem cell growth in monolayers without cell overlap.

Transformed stem cells were seeded as single cells and grown in culture using standard stem cell culture conditions for 4 days. At day 2 and 3 BMP4 was added to each of the treated wells at various concentrations. On day 4 microtiter plates containing treated transformed stem cells were imaged using the cellomics ArrayScan HCS reader (Thermofisher). Referring to FIG. 9, Oct4-GFP expression is shown in green while cell nuclei are shown in blue (Hoescht 33342). A) No BMP untreated control. B) Cells treated with BMP showing a significant loss of GFP expression. As visible in FIG. 9, individual cells are easily identified and are non-overlapping.

Figure 10:
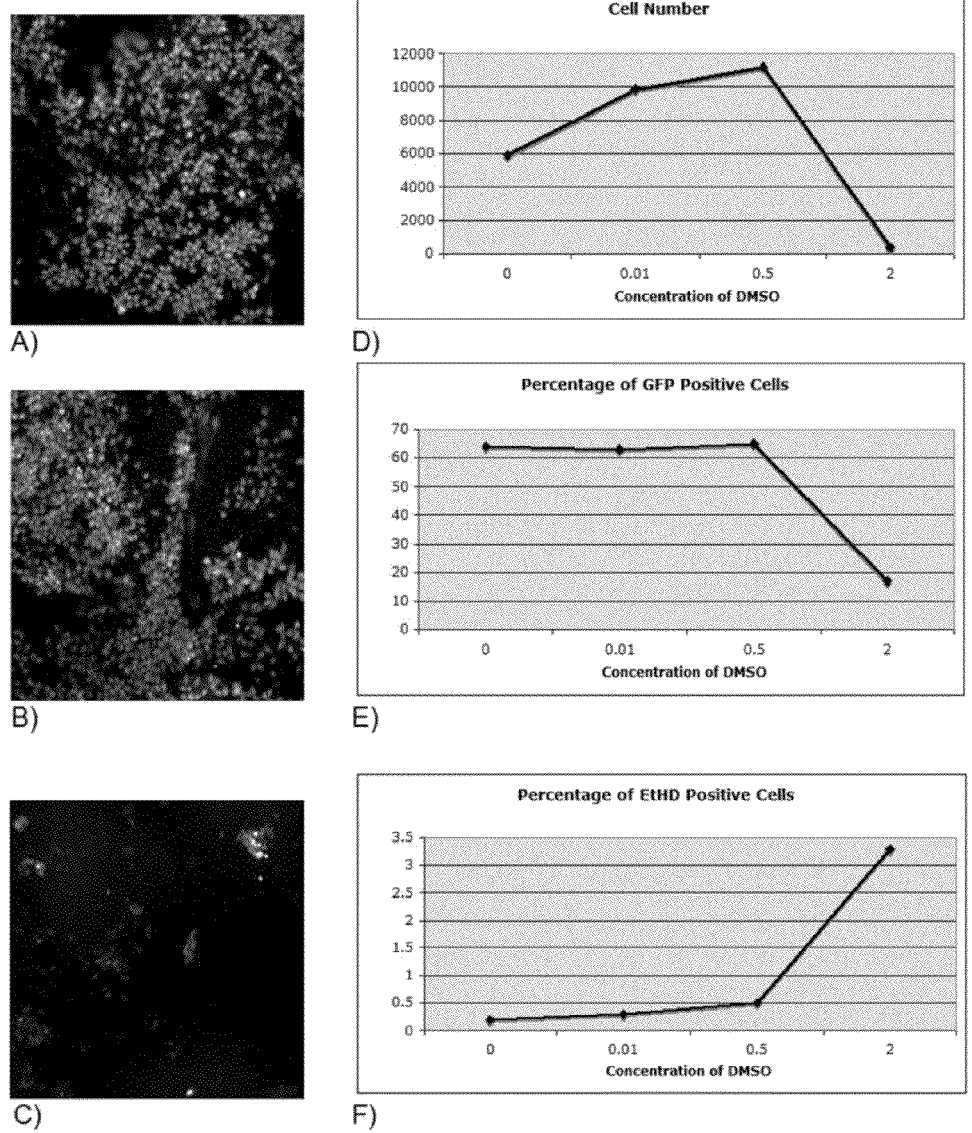
FIG. 10 shows High Content Screening using transformed stem cells. Cells were grown as described in FIG. 9 with the exception of the addition of BMP4 which was replaced by DMSO at multiple concentrations as described in the Figure legends. DMSO is a chemical compound used in drug studies as a solvent which is known to induce stem cell differentiation. On day 5, after cell seeding and culture, microtiter plates were imaged using Thermofisher). Oct4-GFP expression was shown in green while cell nuclei the ArrayScan HCS reader (Thermofisher).

FIG. 10 shows images and metadata derived from transformed stem cells analysed using a High Content Screening platform. Due to image analysis limitations similar data could not be obtained when normal cells were used for the assays. Cells were grown (as described above for FIG. 9) except that DMSO was added to the cells at multiple concentrations in place of BMP4. DMSO is a chemical compound used in drug studies as a solvent which is known to induce stem cell differentiation. On day 5, after cell seeding and culture, microtiter plates were imaged using the ArrayScan HCS reader (Thermofisher). Referring to FIG. 10, A-C show decreasing expression levels of GFP are identified upon treatment of cells with DMSO; GFP is shown in green while blue represent staining by the nuclear dye Hoescht. A, B and C depict GFP expression after treatment of cells for 4 consecutive days with 0%, 0.01% (similar results were found when cells were treated with 0.5% DMSO) and 2% (v/v) of DMSO respectively. D) Cell numbers were quantified based on the automated detection and segregation of cells labelled by the nuclear dye Hoescht. E) Cells were categorized as Oct4-GFP (pluripotency) positive or negative based on the combined expression of GFP and the identification of the nuclear marker Hoescht or sole labelling of nuclear DNA (Hoescht) respectively. The graph displays data obtained by automated image analysis. F) Cells were treated with Ethidium Homodimer (EtDH) which selective penetrates the membrane and labels dead cells red; automated image acquisition and analysis was performed. All images were analyzed using the Cellomics software.

Use of t-hPSCs in Assays for Cancer Stem Cells

The neoplastic features, such as the increased tumour initiating capacity, of transformed pluripotent stem cells create a unique model to study cancer stem cells. The Applicants have shown that transformed stem cells may be used to faithfully predict compound activity on cancer. In a nod/scid mouse experiment, mice transplanted with AML samples and treated with a known chemotherapeutic agent (compound "X") showed lower levels of reconstitution (less cancer). When the same compound was used to treat normal and transformed stem cells, transformed stem cells were selectively killed (apoptosis). These experiments indicate that transformed stem cells can predict the anti-cancer activity of drugs.

In order to examine the activity of compound "X" in a traditional cancer model, 8-weeks-old sublethally irradiated NOD/SCID IL2Rgc null mice were transplanted with an AML sample. Two weeks after transplant, mice were treated daily for 10 consecutive days with the compound "X" drug or vehicle control. Bones were harvested from transplanted mice 8 weeks after. The presence of AML-blast was detected by flow cytometry. As a control, mice were transplanted with healthy HSCs and treated as AML-transplanted ones. As shown in FIG. 11, treatment with compound "X" reduced the level of reconstitution in AML transplanted mice.

Referring to FIG. 12, compound "X" is shown to preferentially target the transformed hESCs (v-hESC) versus normal hESCs promoting hematopoietic differentiation. FIG. 12A shows that basal apoptotic rates are significantly higher in the hESCs versus the v-hESCs, implying that v-hESCs have increased survival and anti-apoptotic capacities. Treatment with compound "X" (100 nM, 4 days) increased apoptosis significantly in both hESCs and v-hESCs, however apoptosis was higher in the v-hESCs versus treated hESCs. ($p<0.001$; n=6) In FIG. 12B, when dsRED-v-hESCs were co-cultured with GFP-hESCs at a 1:1 ratio, compound "X" treatment preferentially targeted the v-hESCs resulting in a 1:5 ratio of v-hESCs to hESCs in the culture as measured by FACS ($p<0.01$; n=3). FIG. 12C shows immunofluorescence imaging of the compound "X" treated flat co-cultures and embryoid bodies (EBs) and further supports the FACS assay indicating that the inhibitor treatment maintains the skewed v-hESCs (red) to hESCs (green) ratio, which remains constant even during the hematopoietic differentiation program (hEB development). Thus, v-hESC being similar to cancer stem cells, given that they show niche independence, have increased anti-apoptotic signaling, enhanced proliferation and low differentiation capacity, are preferentially targeted by the drug versus the normal stem cells. FIG. 12**D shows that compound "X" treatment leads to the emergence of hematopoietic progenitors ($CD45^+CD34^+$) from v-hESCs that are other wise refractory to differentiation, and in addition it also increases hematopoietic output in the normal hESCs (*$p<0.01$; **$p<0.001$; n=9). Hence, compound "X" normalizes the v-hESCs cells resulting in a hematopoietic differentiation profile similar to that observed for the hESCs.

Example 3

Generation of Transformed Induced Pluripotent Stem (t-iPS) Cells

Here, the Applicants describe the derivation of transformed pluripotent stem cells from normal iPS cell lines created after skin fibroblast genetic reprogramming. These cells show several characteristics that are similar to transformed ES including morphological similarities, high prevalence of SSEA3 cells, compromised differentiation and growth factor bFGF independence.

Figure 13:
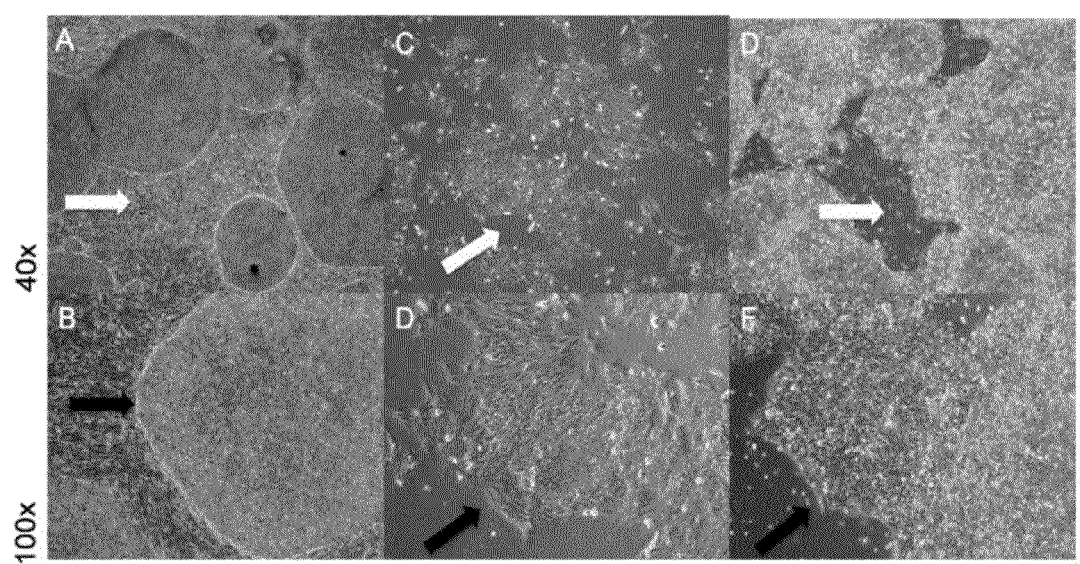
FIG. 13 shows normal versus transformed induced pluripotent stem cell morphology. A: 4× Day 2 after seeding tiPS1.2 p30+9+5+7 (p+MEFs+matrigel&F12+matrigel&CM+trans); B: 10× Day 2 after seeind tiPS1.2 p30+ 9+5+7; C: 4× Day 6 after seeding tiPS1.2 p30+9+5+7; D 10× Day 6 after seeding tiPS1.2 p30+9+5+7; E: 4× Normal iPS1.2 Day 6 after seeding p32+9+5; F: 10× Normal iPS1.2 Day 6 after seeding p32+9+5.

Referring to FIG. 13, phase contrast images of morphological data illustrates the differential characteristics between normal induced pluripotent stem cells (iPSCs) (FIG. 13*a-b*) and transformed induced pluripotent stem cells (tiPSCs) (FIG. 13*c-f*). Normal iPSC morphology consists of a colony with a well-defined border separating it from the surrounding fibroblast-like cells depicted in B (black arrow). In addition, normal iPSCs produce supportive fibroblast-like cells shown in 13A (white arrow). Transformed iPSCs on the other hand do not posses either of these features. They do not produce the supportive fibroblast-like cells (13*c-d* arrows) that help maintain a defined border (13*e-f* arrows).

Normal induced pluripotent stem cells (iPSCs) express SSEA-3 (stage specific embryonic antigen 3), a pluripotency marker characteristically expressed in undifferentiated human pluripotent stem cells. Fluorescence activated cell-sorting (FACS) analysis was performed on normal and transformed iPSCs where the cells are stained for PE conjugated SSEA-3. As indicated in FIG. 14 the frequency for normal iPS1.2 (p32+9+5) cell line is 37.3% (FIG. 14 upper panel, left), which falls within the normal expression range of 30-40%. The transformed iPS1.2 cell line (p30+9+5+7) expressed levels of SSEA-3 that exceeds 60% (FIG. 14 upper panel, right), a result that quite contradictory to the normal cell line. High expression of SSEA-3 indicates that these cells are still pluripotent but could be mistaken as superior but is in fact a characteristic of transformed human pluripotent stem cells.

Another feature of a transformed human pluripotent stem cell is the decreased capacity to undergo in vitro directed differentiation into hematopoietic lineages when compared to its normal counterpart. FACS analysis for differentiated hematopoietic cell markers CD31 and CD45 in both normal and transformed cell lines indicate this distinction. Cells were forced into spontaneous differentiation through the formation of Embryoid Bodies (EBs). Thereafter, EBs were directed to differentiate into hematopoietic lineages according to Example 1. Normal iPSCs show significant hematopoietic differentiation shown by the high expression of both CD31 and CD45 (30.9%, FIG. 14 lower panel, left) but when compared to transformed iPSCs it is evident that the transformed line is impaired, CD31+CD45+(1.6%, FIG. 14 lower panel, right).

Basic fibroblast growth factor (bFGF) is a necessary component in human pluripotent stem cell culture as it aids in the maintenance of the undifferentiated state. Normal iPSCs display growth factor dependence for bFGF. This phenomenon was measured through FACS analysis for SSEA-3, a common marker for pluripotency. As shown in FIG. 15, upon depleting concentrations of bFGF (10, 8, 4, 2, and 0 ng/mL) normal iPSCs show a synchronized decrease in frequency of SSEA-3 (37% to 28%, FIG. 15, upper panel), indicating loss of the undifferentiated state whereas the transformed iPSCs maintain an SSEA-3 frequency of over 60% (FIG. 15, lower panel). This finding negates the normal phenotype of optimal colony growth in 10 ng/mL bFGF.

Example 4

Pluripotent Transcription Factors Possess Distinct Roles in Normal Versus Transformed Human Stem Cells Similar gene expression patterns in normal Stem Cells (SCs) and cancer cells suggest that tumors may utilize normal SC self-renewal machinery to facilitate or initiate neoplastic progression. In this Example, the Applicants evaluated the functional role of two TFs, Oct4 and Nanog, that correlate with aggressive adult tumors, in normal and transformed human stem cells (hSCs). While transformed pluripotent SCs are completely independent of Oct4 for cell maintenance, they require Nanog to maintain self-renewal and survival. These observations establish that expression of core TFs is not necessarily indicative of tumor phenotype, thus underscoring the need to functionally validate biomarkers that may link SCs with cancer. The divergent roles of Oct4 and Nanog in normal vs. transformed cells permit the use of assays for the development of drugs that selectively target these factors in the most aggressive tumors that acquire embryonic molecular signatures.

Cancer cells share a variety of properties with normal SCs including self renewal capacity, but lack the ability to differentiate and undergo apoptosis in a similar fashion to normal SCs. Cell populations have been identified in a variety of human cancers that possess self-renewal capacity, but are also capable of initiating tumor heterogeneity in xenograft models (34, 36, 51, 29, 30, 28). These properties, along with phenotypic resemblance to normal SCs, define the term Cancer Stem Cell (CSC) (44, 50) and perpetuate the notion that CSCs may capitalize on molecular machinery controlling normal SC function for maintaining oncogenic properties. For example, Bmi-1, a polycomb group (PcG) gene, was shown to be essential for both normal and leukemic mouse SC proliferation (54). Aside from this work, little is known about the functional relevance of genetic determinants to CSCs versus their normal SC equivalents.

Unlike other hSCs, molecular control of self-renewal is well established in the embryonic stem cell (ESC) system and has been found to be governed by a core set of TFs that maintain the undifferentiated ground state (37). These factors that include Octamer4 (Oct4) (23, 59) and Nanog (23, 40, 58) have recently been associated with highly aggressive adult tumors (15, 41, 46, 49, 62, 65). These observations suggest that factors controlling robust self-renewal unique to ESCs may be important for aggressive somatic tumor growth (52). To this point, overexpression of Oct4 is sufficient to induce dysplastic growth in adult mouse epithelium (47) and enhance the malignant potential of ESC-derived germ cell tumors (46). Similarly, Nanog expression has also been detected in a variety of human neoplasms (35, 39, 43, 45, 48, 66, 68). Nanog downregulation has recently been shown to inhibit prostate, breast and colon tumor development both in vitro and in vivo (49). However, the functional and mechanistic roles of Oct4 and Nanog in CSCs vs. normal SCs are unknown.

hPSCs with features of neoplastic progression including aberrant self-renewal and resistance to differentiation amounting to enhanced tumorigenic potential have recently been characterized (See Example 1). To determine the role of core pluripotent TFs in human SC transformation, the Applicants directly compared the effect of Oct4 and Nanog downregulation on self-renewal of normal vs. transformed hPSCs. t-hPSCs, unlike their normal counterparts, are independent of Oct4 for self-renewal, pluripotency and survival. Both cell types require Nanog for SC state maintenance, but t-hPSCs exhibit an unprecedented dependency on Nanog for self-renewal and cell survival. The present Example establishes a paradigm by which functional divergence of pluripotent TFs from the normal SC state accompanies transformation and can therefore be used to develop therapies targeting somatic CSCs in severely aggressive tumors.

Results

Downregulation of Oct4 does not Alter Self-Renewal or Survival of T-Hpscs

Figure 20:
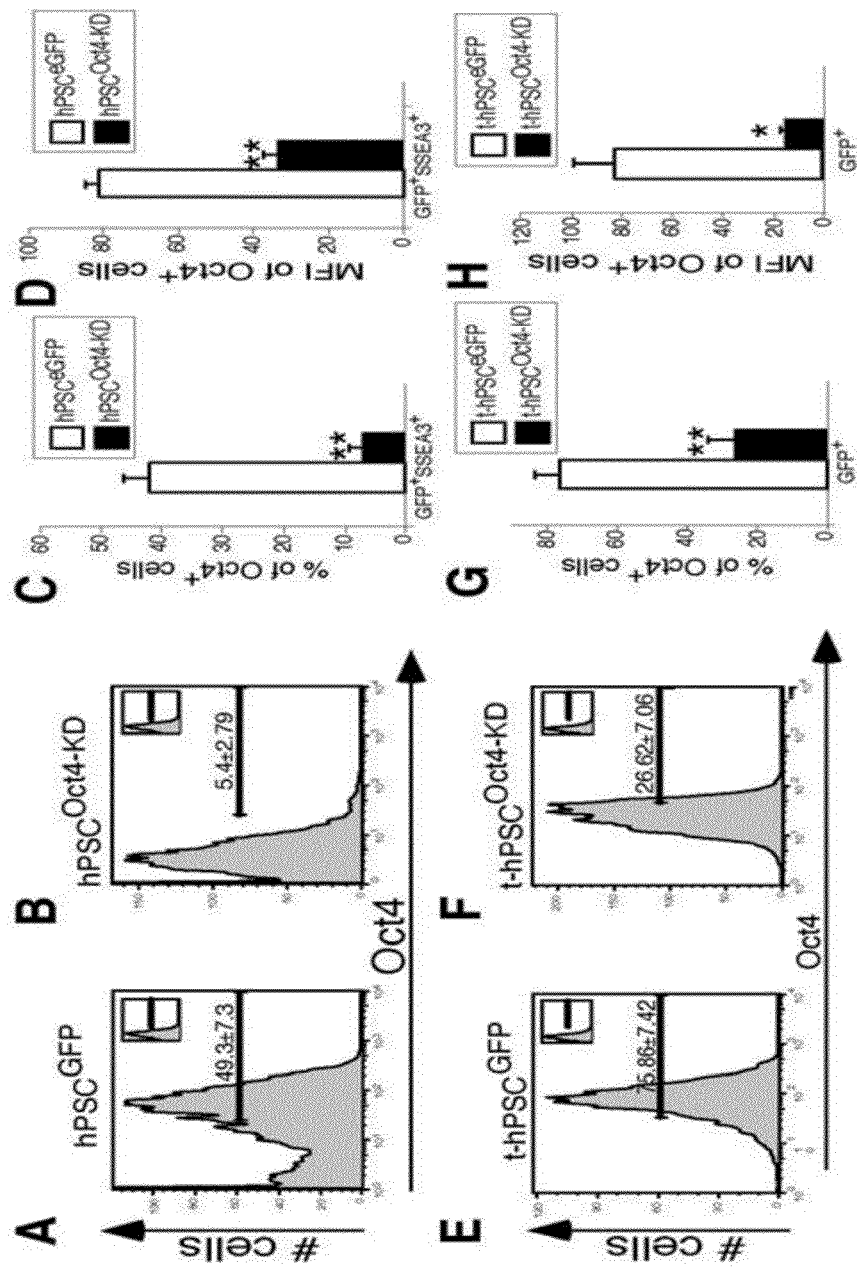
FIG. 20 shows that Lentivirus based Oct4 and Nanog shRNA significantly downregulate Oct4 and Nanog expression respectively in both normal hPSCs and t-hPSCs. (A-B) Representative FACS histograms of Oct4+ cell frequency within gated GFP+SSEA3+ fractions from control (A) and Oct4 knockdown (B) hPSCs. (C-D) Frequency (C) and mean fluorescence intensity (D) of Oct4+ cells within gated GFP+SSEA3+ fractions from control and Oct4 knockdown hPSCs. Error bars represent SEM, n=3. (E-F) Representative FACS histograms of Oct4+ cell frequency within gated GFP+ fraction from control (E) and Oct4 knockdown (F) t-hPSCs. (G-H) Frequency (G) and mean fluorescence intensity (H) of Oct4+ cells within the gated GFP+ fraction from control and Oct4 knockdown t-hPSCs. Error bars represent SEM, n=5. (I-L) Representative images of bulk H1 and H9 hPSCs one week after transduction with the control lentilox vector LL37 (eGFP as transduction reporter, hPSCeGFP) (I-J) or the Oct4 knockdown lentiviral vector (K and L). Scale bar=100 µm, n=5. I and K: Phase contrast. J and L: GFP. (M-P) Representative images of bulk H9 t-hPSCs one week following transduction with control (M and N) and Oct4 knockdown lentiviral vectors (O and P). n=5. M and O: Phase contrast. N and P: GFP. Scale bar=100 µm. (Q-T) Representative images of control (Q and R) and Oct4 knockdown (S and T) t-hPSC cultures 4 months after sorting GFP+ cells. Scale bar=100 µm. (U) qPCR of fold changes in Nanog transcripts following stable Nanog knockdown (black bars) in both hPSCs and t-hPSCs relative to transduction with the control eGFP lentivirus (white bars). Bar graphs represent mean values±SEM, n=3, ***, $p<0.001$. (V) qPCR results showing the fold change of t-hPSC Nanog transcript relative to normal hPSCs. Bar graphs represent mean values±SEM, n=3.
Figure 20:
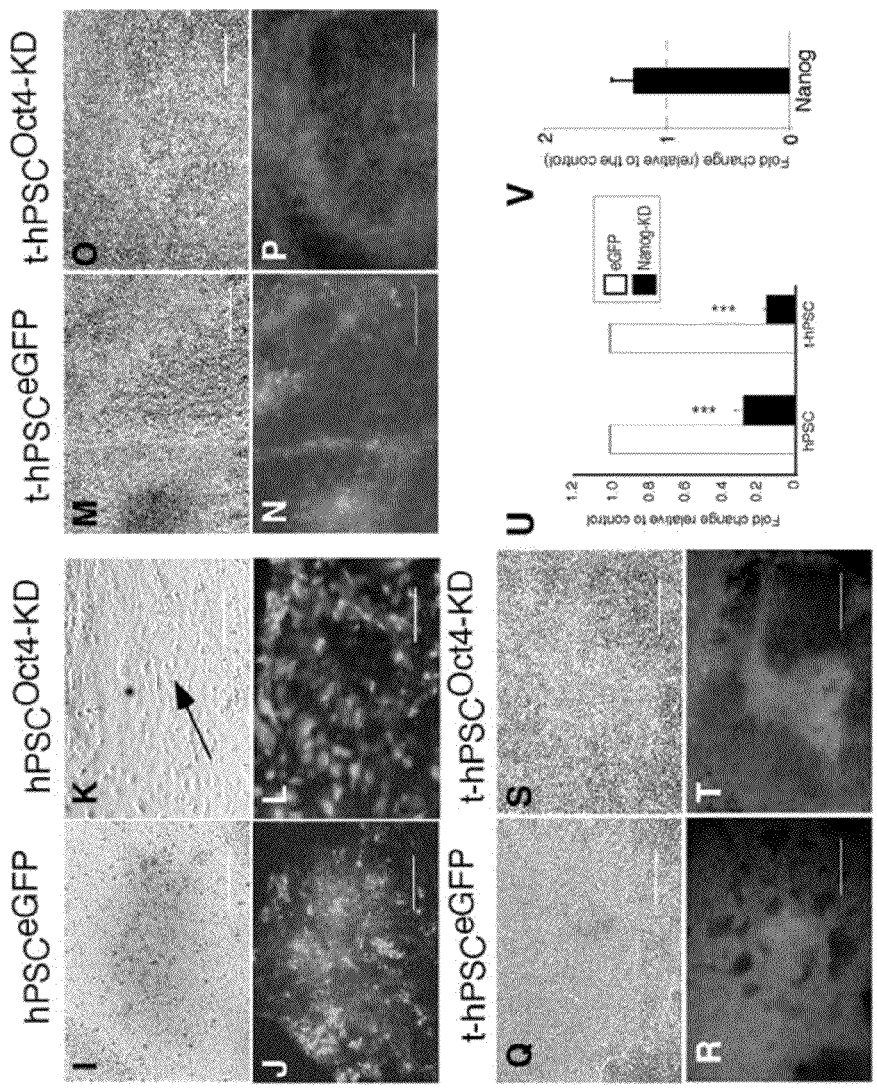
Figure 21:
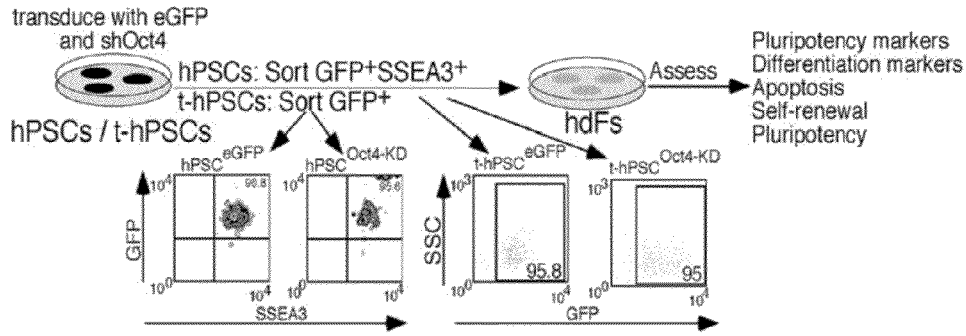
FIG. 21 shows a schematic of GFP+SSEA3+ and GFP+ fractions isolation from control and Oct4 knockdown normal hPSCs and t-hPSCs respectively. Sorted cells were seeded at clonal density on irradiated hdFs and sorting purities for each fraction are shown.

To determine the functional relevance of Oct4 in normal and transformed hSCs, the Applicants stably knocked down Oct4 levels in both normal hPSCs and t-hPSCs using shRNA. Quantification of Oct4 downregulation by flow cytometry demonstrated effective knockdown in both cell types (See FIG. 20A-H). This was determined by frequency of Oct4+ cells (FIGS. 20A-C, E-G) and the number of Oct4 molecules/ cell measured by mean fluorescent intensity (FIGS. 20D and H). Consistent with previous reports (57, 67) hPSC colonies differentiated 7 days following Oct4 depletion (FIG. 20I-L). However, hPSC cultures are morphologically, phenotypically, and functionally heterogeneous, and are re-established by rare colony-initiating cells (CICs) enriched in the SSEA3+ fraction (17). To dissect the role of Oct4 in this clonogenic subpopulation, normal hPSCs were isolated based on green fluorescent protein (GFP) in combination with the undifferentiated hSC marker SSEA3 and subsequent colony growth was quantitatively compared (FIG. 21). Oct4 downregulation resulted in visible differentiation of hPSC colonies (FIGS. 16A-D).

Figure 16:
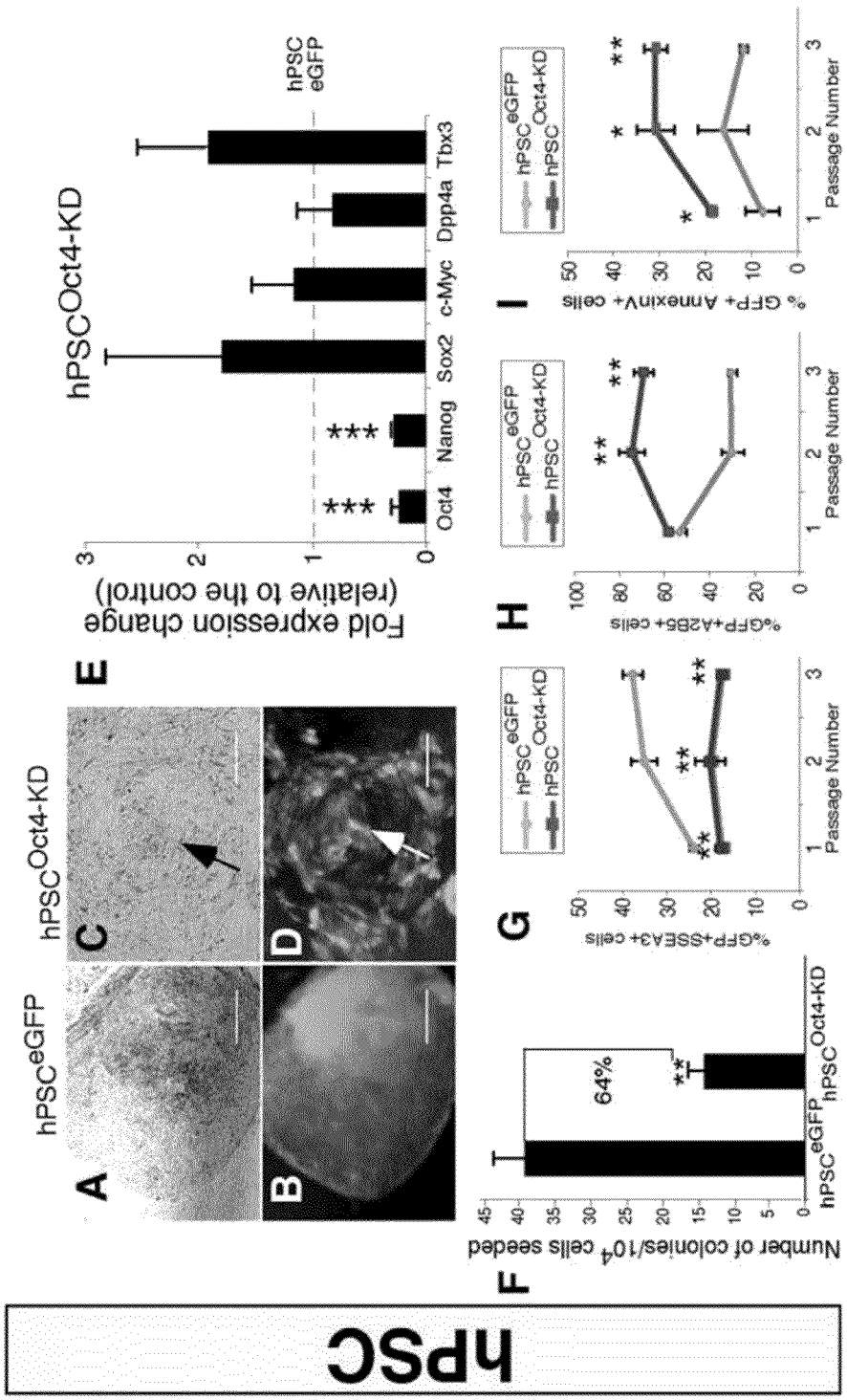
FIG. 16 shows that Oct4 knockdown does not affect self-renewal, differentiation and survival of t-hPSCs. (A-D) Representative images of colonies generated from GFP+SSEA3+ cells 11 days post-sort from control (A and B) and Oct4 knockdown (C and D) normal hPSCs. Scale bar=100 μm, n=3. Arrows denote differentiated cells following Oct4 knockdown. (E) qPCR of fold changes in Oct4, Nanog, Sox2, c-Myc, Dpp4a, and Tbx3 transcripts in Oct4 knockdown hPSCs relative to hPSC eGFP controls. Bar graphs represent mean values±SEM, n=3, *, $p<0.001$. (F) Clonogenic self-renewal of SSEA3+ cells isolated from control (39.3±4.3×104) and Oct4 knockdown (14±2.3×104) hPSCs. 1×104 GFP+SSEA3+ cells were isolated from hPSCs 2 days after transduction with eGFP control and Oct4 knockdown lentiviral vectors and seeded on ihdFs. GFP+ colonies were scored 9 days after seeding. Bar graphs represent mean values±SEM, n=3. , $p<0.01$. (G-I) Frequency of GFP+SSEA3+(G) GFP+A2B5+(H) and GFP+AnnexinV+ (I) cells for three passages of culture derived from sorted GFP+SSEA3+ fractions of control and Oct4 knockdown hPSCs. N=3 for each. Line graphs represent mean values±SEM. * $p<0.05$,  $p<0.01$. (J-M) Representative images of colonies generated from sorted GFP+ cells 6 days post-sort from control (J-K) and Oct4 knockdown (L-M) t-hPSCs. Scale bar=100 n=5. Arrow denotes the typical appearance of tightly packed undifferentiated colonies. (N) qPCR of fold changes in Oct4, Nanog, Sox2, c-Myc, Dpp4a, and Tbx3 transcripts in Oct4 knockdown t-hPSCs relative to t-hPSC eGFP control cells. Bar graphs represent mean values+/−SEM, n=3, , $p<0.01$, ***, $p<0.001$. (O) Clonogencity of GFP+ cells isolated from control and Oct4 knockdown thPSCs. 1×104 GFP+ cells were sorted from t-hPSCs 4 days after transduction with eGFP control and Oct4 knockdown lentiviral vectors and seeded on ihdFs. GFP+Colonies were scored 6 days after. Bar graphs represent mean values+/−SEM, n=3. (P-R) Frequency of GFP+SSEA3+(P) GFP+A2B5+(Q) and GFP+AnnexinV+ (R) cells for three passages of culture derived from sorted GFP+ fractions of control and Oct4 knockdown t-hPSCs. P, n=9. Q, n=5, R, n=3. Line graphs represent mean values+/−SEM.
Figure 16:
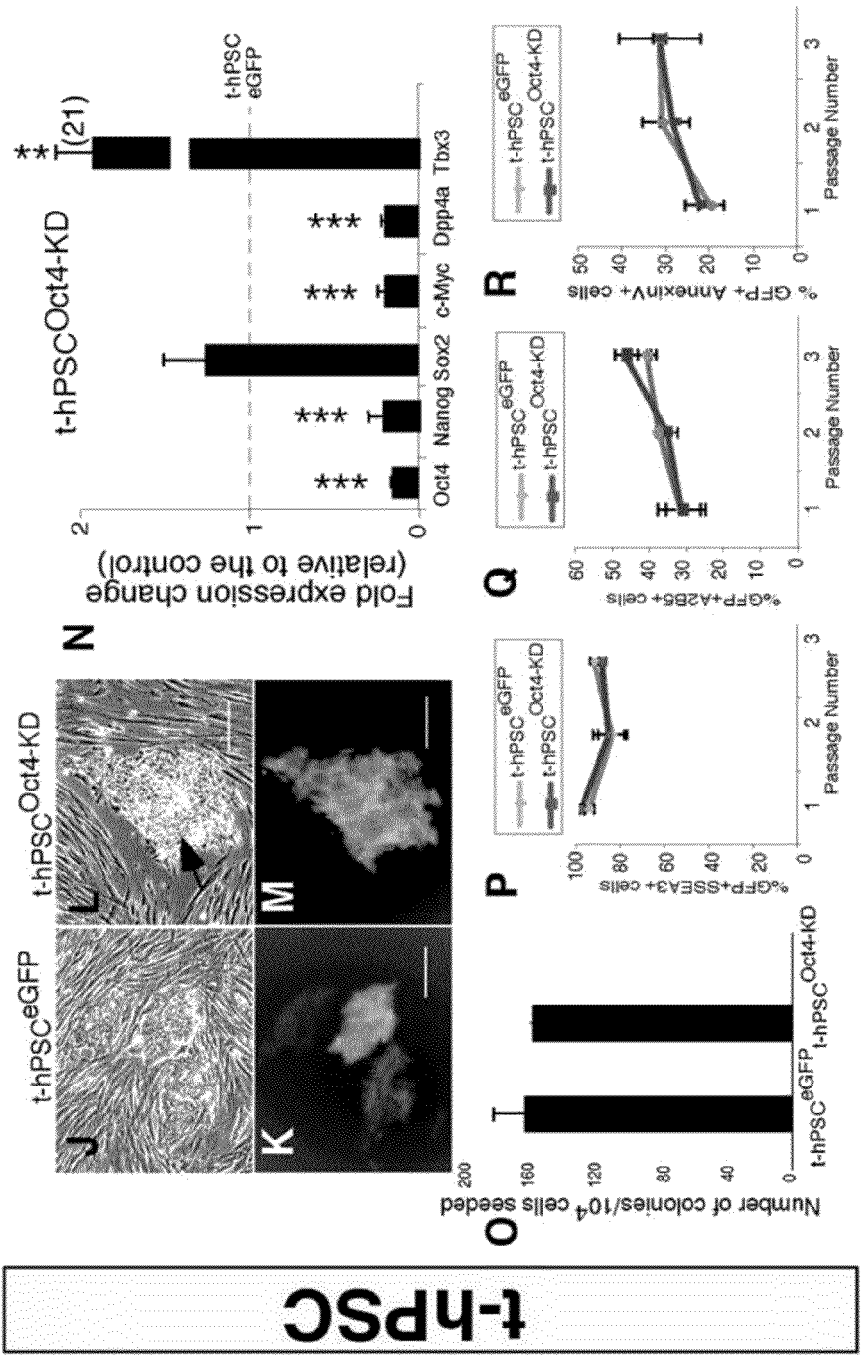

To investigate the molecular mechanisms associated with Oct4 depletion in hPSCs, the Applicants compared changes in transcript levels of Oct4, Nanog, SRY (sex determining region Y)-box 2 (Sox2), V-myc myelocytomatosis viral oncogene homolog (avian) (c-Myc), dipeptidyl-peptidase 4a (Dpp4a) and T-box 3 (Tbx3), all implicated in pluripotent stem cell maintenance (23, 63). As expected, lentiviral shRNA transduction of Oct4 significantly reduced Oct4 but also downregulated Nanog transcripts in SSEA3+ hPSCs (FIG. 16E). However, Sox2, c-Myc and Tbx3 levels showed slight, non-significant increases following Oct4 dysregulation (FIG. 16E) while Dpp4a levels were minimally decreased (FIG. 16E). Taken together, these results confirm the previously established role of Oct4 in differentially regulating gene expression in normal hPSCs, and the central importance of these factors in maintaining the pluripotent state (23, 42, 60, 63, 67).

In addition to the molecular changes seen following Oct4 knockdown, the Applicants dissected the biological effects on the self-renewing hPSC SSEA3+ fraction. Oct4 downregulation reduced the total number of clonogenic self-renewing cells (CICs) by 64% compared with cells transduced with the eGFP control vector (FIG. 16F). In addition, Oct4 downregulation significantly decreased the frequency of undifferentiated SSEA3+ cells and increased the frequency of the neural precursor marker, A2B5, compared with control eGFP cells (FIG. 16G-H). Oct4 knockdown also induced cell death as demonstrated by AnnexinV+ staining (FIG. 16I). These results show that Oct4 regulates a differentiation response in the self-renewing fraction of normal hPSCs and is therefore required for maintenance and survival of the hPSC undifferentiated state.

Unlike normal hPSCs, t-hPSCs are less morphologically and phenotypically heterogeneous demonstrated by ubiquitous expression of SSEA3 throughout the culture, and do not require the fibroblast-like cell supportive niche (See Example 1). To evaluate the functional role of Oct4 in thPSCs, we stably knocked down Oct4 by shRNA and then isolated fractions based on green fluorescent protein (GFP) (FIG. 21). Surprisingly, both t-hPSC bulk cultures (FIGS. 20M-P) and GFP+ fractions (FIG. 16J-M) appeared completely unaffected by Oct4 dysregulation. Undifferentiated colonies were phenotypically similar to both the control and parental t-hPSCs (FIG. 16J-M).

Comparable to normal hPSCs, Oct4 reduction in t-hPSCs resulted in a significant and predictable reduction in Oct4 as well as a similar decline in Nanog and a small increase in Sox2 levels (FIG. 16N). Along with a substantial increase in Tbx3 expression, both c-Myc and Dpp4a were significantly reduced in Oct4 t-hPSCs. (FIG. 16N). Differential regulation of c-Myc, Dpp4a and Tbx3 reveals a molecular distinction in response to Oct4 depletion between t-hPSCs and hPSCs that may be, at least in part, responsible for the lack of response of thPSCs to Oct4 dysregulation.

Although there were no discernible changes in t-hPSC colonies following Oct4 knockdown, the Applicants further assessed the functional relevance of Oct4 to t-hPSC clonogenic self-renewal, differentiation and survival. Unlike normal hPSCs, downregulation of Oct4 had no effect on colony formation (FIG. 16O) or the frequencies of SSEA3+, A2B5+, and AnnexinV+ cells over multiple passages (FIGS. 16P-R). The inability to alter self-renewal in t-hPSCs persisted even four months after Oct4 depletion (FIG. 20 Q-T). These data demonstrate that Oct4 is dispensable for the self-renewal and survival of t-hPSCs, but is critical to normal hPSC maintenance. Despite the established key role of Oct4 in sustaining pluripotency, the present results provide direct evidence for the functional divergence of Oct4 from the pluripotent state following transformation.

Figure 17:
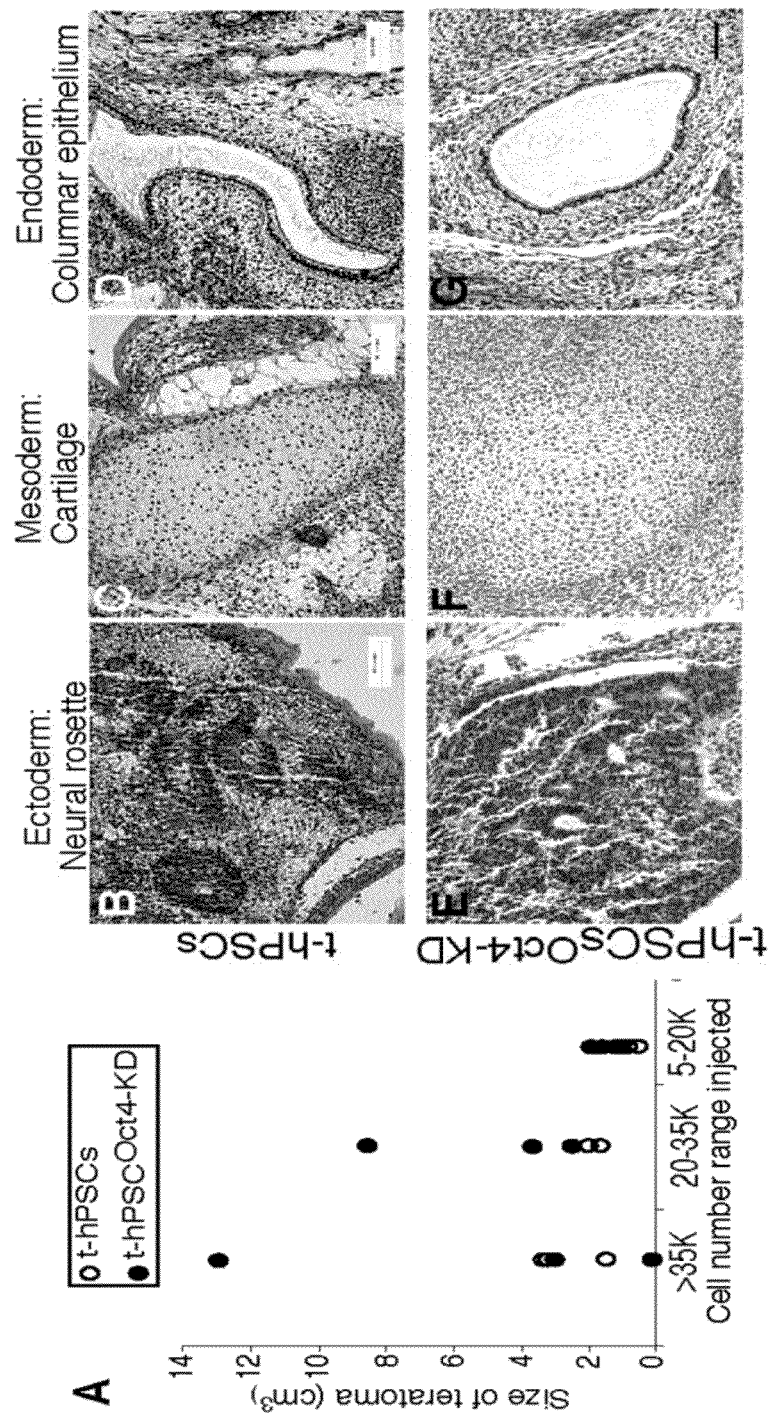
FIG. 17 shows that downregulation of Oct4 has no effect on t-hPSC pluripotency or tumor-initiating cell capacity. (A) Summary of teratoma formation from control and Oct4 knockdown t-hPSCs at serial injected cell doses. Cell doses of 7.5×103, 2.4×104, and 6.6×104 t-hPSCs and 1.5×104, 3.3× 104 and 6.6×104 Oct4 knockdown t-hPSCs were injected into the testis capsules of NOD/SCID mice. Mice were sacrificed 6 weeks after injection. Teratoma size was measured and plotted relative to injected cell doses. N=7. (B-G) Representative histology of teratomas formed in NOD/SCID mice testes 6 weeks following injection of control t-hPSCs (B-D, upper panel) or Oct4 knockdown t-hPSCs (E-G, bottom panel). Tissues representing all three embryonic germ layers including ectoderm (neural rosettes, B and E, left panels), mesoderm (cartilage, C and F, middle panels), and endoderm (columnar epithelium, D and G, right panels) are shown. Scale bar=50 µm.

Oct4 is not Required for Pluripotency and Tumorigenicity of T-Hpscs hPSC pluripotency is determined in vivo by the presence of all 3 germ layers in teratomas formed in human-mouse xenografts. Teratomas are formed from a rare subset of cells present at a frequency of 1:17500 cells in normal hPSCs (See Example 1). In contrast, we have recently shown that t-hPSCs are highly enriched for teratoma-initiating cells (TICs) with a frequency of 1:800 and give rise to teratomas containing clusters of Oct4 positive cells (See Example 1). Oct4 expression has been associated with more aggressive tumors and is suggested to be a malignant teratocarcinoma marker in vivo (22, 46, 21). To determine whether Oct4 is related to the higher TIC frequency and capacity of t-hPSCs, the Applicants injected t-hPSCs depleted in Oct4 at different cell doses into NOD-SCID mice. All mice (9/9 mice), regardless of limiting dose, developed teratomas (FIG. 17A; Table 1). Teratomas generated from both Oct4 depleted and control t-hPSCs consisted of tissues representing all three germ layers (FIGS. 17B-G; Table 1). Furthermore, these teratomas were similar in size to controls suggesting that Oct4 does not affect t-hPSC proliferation or TIC capacity in vivo (FIG. 17A; Table 1). These results demonstrate that t-hPSCs with depleted Oct4 retain pluripotency and TIC capacity and indicate that the enhanced tumorigenesis of t-hPSCs (See Example 1) is not dependent on Oct4. These functional results question previous notions that retention of Oct4 alone can be used as a functional indicator of hSC transformation (22, 46, 21).

t-hPSCs are Dependent on Nanog for Survival and Self-Renewal

In addition to Oct4, Nanog has also been established as a core pluripotency factor (40, 58). However, the role of Nanog in SC transformation is unknown. To determine the functional relevance of Nanog expression, the Applicants stably and effectively knocked down Nanog using shRNA in both hPSCs and t-hPSCs (FIG. 20U). Consistent with previous reports (67), Nanog depletion resulted in the differentiation of colonies in normal hPSC cultures demonstrating that this TF is required for normal pluripotent SCstem cell maintenance (FIG. 18A-B). Since normal hPSCs underwent differentiation, we then isolated transduced GFP+ hPSCs expressing the primitive marker SSEA3 to investigate the specific effect of Nanog depletion on the self-renewing clonogenic fraction.

Nanog and Oct4 co-occupy target genes and form specialized autoregulatory and feedforward loops to establish molecular control of ESC pluripotency (23, 56). To evaluate the molecular mechanisms responsible for the functional changes in clonogenic hPSCs following Nanog knockdown, the Applicants looked at transcript levels of genes associated with hPSC pluripotency. While shRNA-based Nanog depletion decreased Dpp4a expression, both Oct4 and c-Myc levels remained unchanged in normal hPSCs (FIG. 18C). In contrast, Tbx3 transcript was significantly upregulated along with an increase in Sox2 levels (FIG. 18C). The similar gene expression patterns following both Oct4 and Nanog downregulation in hPSCs confirm previous studies demonstrating that these TFs share several targets (23).

To characterize the relevance of Nanog dysregulation to hPSC function, we examined the effect of Nanog reduction on hPSC clonogenic self-renewal, differentiation and survival. Similar to Oct4, Nanog downregulation also significantly decreased the number of colonies generated from the SSEA3+ subset as compared to controls (FIG. 18D). This indicates a critical role for Nanog in the clonogenic self-renewal of normal hPSCs. This reduction in self-renewal potential was consistent with the loss in SSEA3 over passage and was also accompanied by an increase in the expression of the neural marker A2B5 (See Example 1) demonstrating a role for Nanog in preventing differentiation (FIG. 18E-F). Additionally, Nanog knockdown induced apoptosis represented by an increased frequency of Annexin V+ cells (FIG. 18G). Together, these results show that Nanog is critical in maintaining the undifferentiated state of normal hPSCs while repressing both neural differentiation and apoptosis.

Transformed-hPSCs expressed higher levels of Nanog than normal hPSCs. (FIG. 20V). Given the lack of effect of Oct4 depletion on transformed cells, the Applicants sought to investigate whether Nanog regulates t-hPSC function. Nanog knockdown induced differentiation and compromised viability in t-hPSCs bulk compared to eGFP controls (FIGS. 18H-I). To evaluate the molecular mechanisms associated with these biological changes, we isolated GFP+ cells from Nanog-depleted t-hPSCs and examined transcript levels of Oct4, Nanog, Sox2, c-Myc, Dpp4a and Tbx3 compared with cells transduced with the control eGFP vector. Relative to normal hPSCs, Nanog knockdown in t-hPSCs resulted in similar patterns of Nanog, Oct4, Sox2, and Dpp4a transcript regulation (FIG. 18J). However, significant decreases in both c-Myc and Tbx3 (FIG. 18J) demonstrate that Nanog differentially regulates transcriptional networks in thPSCs compared with normal cells. To understand the potential biological effects of Nanog depletion on the self-renewing fraction, transduced t-hPSCs were selected and cultured to evaluate effects on self-renewal, differentiation and apoptosis. Surprisingly, Nanog downregulation completely abolished colony formation capacity (FIG. 18K) revealing an obligatory role for Nanog in the clonogenic self-renewal unique to t-hPSCs vs. normal hPSCs. Since colonies could not be recovered following Nanog depletion in t-hPSCs, the Applicants measured the effect of Nanog downregulation on t-hPSC differentiation using GFP+ cells from transduced bulk culture. SSEA3 levels were significantly reduced after 3 passages, however, there was no change in frequency of cells expressing A2B5 (FIG. 18L-M). This demonstrated that unlike normal hPSCs, Nanog does not regulate t-hPSC neural differentiation. t-hPSCs also underwent a significant apoptotic induction shown by an increased frequency of Annexin V+ cells (FIG. 18N). Together, these results demonstrate a potent and distinct hypersensitivity of t-hPSCs to Nanog.

Nanog Regulation of Apoptosis in t-hPSCs is Oct4 Dependent

Figure 19:
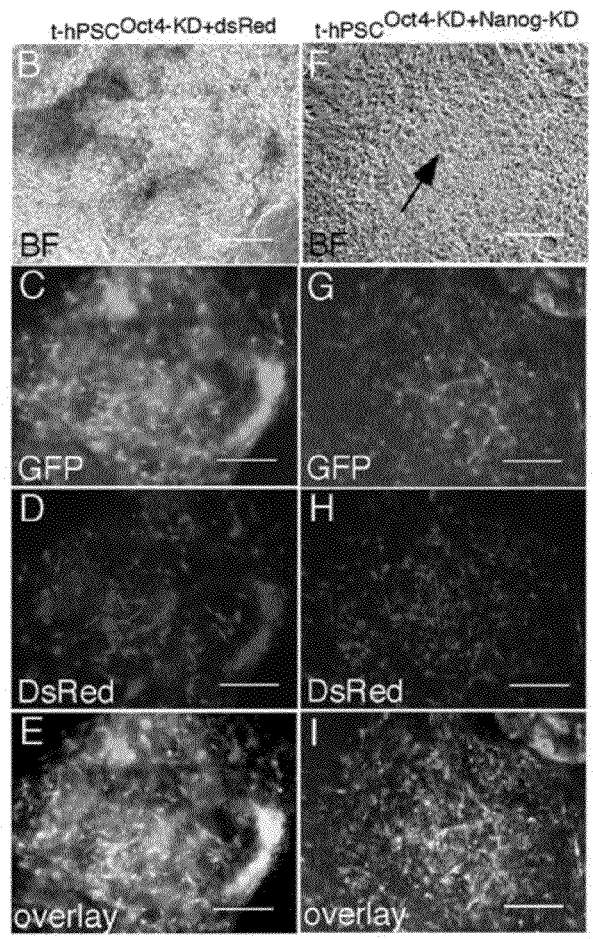
FIG. 19 shows survival of t-hPSCs after dual and sequential knockdown of Oct4. (A) Schematic showing the protocol for dual and sequential knockdown of Oct4 and Nanog in t-hPSCs. (B-I) Representative images of control (B-E) and dual Oct4 and Nanog knockdown (F-I) t-hPSCs 2 weeks after transduction with the shOct4_GFP vector followed by control DsRed and shNanog_DsRed vectors, respectively. Scale bar=100 µm, n=3. Arrow denotes t-hPSC colony cells that survived dual and sequential knockdown of Oct4 and Nanog. (J) Representative FACS results showing the frequencies of Annexin V+ cells within GFP+DsRed+ fractions of control and dual Oct4 and Nanog knockdown thPSCs. n=3. (K) Frequency of Annexin V+ cells within GFP+DsRed+ fractions of control and dual Oct4 and Nanog knockdown t-hPSCs. (13±2.1% AnnexinV+ cells in Oct4 KD/dsRED t-hPSC controls vs 15.9±9.2% Annexin V+ cells in Oct4 KD/Nanog KD-dsRED t-hPSCs. Bar graphs represent mean values±SEM, n=3, $p>0.05$. (L) While both Oct4 and Nanog are required to sustain the normal human stem cell pluripotent state, Oct4 is dispensable for transformed human stem cell self-renewal and survival. However, transformed human stem cells are completely dependent on Nanog for both self-renewal and survival revealing a fundamental paradigm shift in the role of core TFs following transformation. This heightened effect of Nanog on transformed cell survival is dependent on Oct4.

Although Nanog downregulation induced cell death in t-hPSCs (FIG. 18N), Nanog transcript downregulation following Oct4 knockdown did not induce a similar apoptotic response in t-hPSCs (FIG. 16N). This suggests that Nanog regulated survival is Oct4 dependent. To examine the specific functional relationship of Oct4 and Nanog in transformed hSCs, the Applicants performed both dual and sequential knockdown of Oct4 and Nanog in t-hPSCs using the approach depicted (FIG. 19A). Consistent with our previous results, initial Oct4 knockdown had no effect on t-hPSC differentiation (FIGS. 19B-C,F-G and data not shown). Surprisingly, dual Oct4 and Nanog knockdown t-hPSCs survived compared with control t-hPSCs (FIGS. 19D-E, H-I). The potent apoptotic effect seen in Nanog knockdown only transformed cells (FIG. 18N) was completely abolished when sequential knockdown of Oct4 and Nanog was performed (FIGS. 19J-K). This demonstrates that Nanog-regulated apoptosis is dependent on Oct4. Our results reveal a hierarchical role for Nanog and Oct4 in t-hPSC regulation.

Discussion

Unlike other SCs, the core transcription factors that regulate self-renewal, survival and developmental potential are well established in hPSCs (23). This provides a unique opportunity to determine the role of these governing factors in the normal vs. transformed SC state in a manner that cannot be fully evaluated in other CSC systems limited by patient sample heterogeneity and availability of large cell numbers. The present example defines a mechanistic distinction for the role of Oct4 and Nanog in transformed vs. normal hSCs. While embryonic gene expression patterns have recently been associated with malignancy (15, 62, 65), the Applicants provide evidence that Oct4 alone may have unique functions in normal SCs, whereas transformed SCs are strongly dependent on Nanog. Based on these results, the Applicants propose a model to describe the functional role and relationship of Oct4 and Nanog, in transformed vs. normal SC state (FIG. 19L).

Differences that separate normal vs. cancer SC molecular circuitry are not well characterized and therefore hinder development of novel therapeutics that specifically target CSCs. A reduction in Oct4 and Nanog levels induces spontaneous lineage development and loss of pluripotent self-renewal capacity in hPSCs (57, 59, 67). Unlike normal SCs, Oct4 is dispensable for self-renewal, survival and differentiation of transformed cells (FIG. 19L). In contrast, Nanog represents an "achilles heel" in transformed SCs as the strong survival effect combined with the abolishment of clonogenic self-renewal reveals a fundamental dependence on a single TF for cellular maintenance in the transformed state. The role for Nanog in t-hPSC survival was dependent on Oct4, as evidenced by abolishment of the apoptotic effect following dual knockdown. The inherent vulnerability of t-hPSCs to Nanog, in contrast to normal hPSCs, suggests that functional characterization of TFs governing the pluripotent state may reveal unique dependencies of SCs upon entry into transformed states of self-renewal and neoplasia.

While Oct4 plays a regulatory role in t-hPSC survival, the present Examples indicate that Oct4 expression is not a relevant criterion to pathologically define transformation of hPSCs in vitro or in vivo. This is supported by evidence demonstrating that Oct4 is not detected in a panel of nearly 200 solid tumors (46) and is dispensable for the maintenance of adult mammalian somatic SCs (53). Prior to these functional TF studies, the overexpression of Oct4 in cultured t-hPSCs combined with the presence of Oct4-positive pluripotent cells in teratomas (See Example 1) would have been misconstrued as indicators of malignant progression of hPSCs. As such, differential expression of core TF genes does not necessarily link SCs with cancer, thus underscoring the need for functional validation of all potential biomarkers. Nevertheless, the association of embryonic gene expression patterns with malignancy has recently gained considerable momentum (15, 62, 65). Combined with the present Examples, this implies that tumor cells acquire heightened self-renewal capacity by hijacking TFs typically associated with hPSCs, or that CSC populations utilize pluripotent TFs for tumor maintenance. Involvement of Oct4 and Nanog in either process would allow one to capitalize on these functional dependencies and target TFs therapeutically.

TFs are critical regulators of normal SC and cancer cell self-renewal, survival and differentiation. The present disclosure reveals a functional divergence of transcriptional machinery from the normal SC self-renewing state versus transformation. In light of recent studies demonstrating a role for Oct4 and Nanog in tumor progression (41, 49), this mechanistic distinction is likely not exclusive to hPSCs, but more broadly applicable to multiple CSC types. The divergent roles of Oct and Nanog revealed in this disclosure establish a paradigm to develop novel therapeutics towards selective destruction of aggressive tumors harboring CSCs with similar molecular signatures.

Experimental Procedures

Culture of hPSCs and t-hPSCs, and Formation of hEBs. H9 and H1 hPSC lines as well as the H9-derived t-hPSC line were cultured as previously described (Example 1). Briefly, all cell lines were cultured on Matrigel (BD Biosciences) coated plates and maintained in mouse embryonic fibroblast conditioned medium (MEF-CM) supplemented with 8 ng/ml 13 of human recombinant basic fibroblast growth factor (bFGF, Invitrogen) (33). Formation of hEBs from t-hPSCs and hematopoietic differentiation of hEBs were performed as previously reported (33, 64)

Lentiviral shRNA Vector Subcloning. Construction of the lentiviral vector Lentilox37 (LL37) carrying the eGFP reporter was performed as described (61). An oligonucleotide targeting the human Nanog gene and two oligonucleotides targeting the human Oct4/POU5F1 gene were designed and generated (67). The third oligonucleotide encoding stem-loop structures targeting the human Oct4/POU5F1 gene was designed using the Darmacon company siRNA design tool. These oligonucleotides were subcloned into the LL37 vector under the control of the U6 promoter. DsRed was subcloned into the LL37 control vector to replace eGFP.

Briefly, DsRed was amplified with primers including Nhe1 and EcoR1 as restriction sites respectively and was inserted into LL37 vector by replacing eGFP sequences. The oligonucleotide targeting the human Nanog gene was also subcloned into the engineered lentiviral vector carrying DsRed as the reporter. All engineered lentiviral vectors were verified by sequencing.

Lentiviral Virus Production and hPSCs Transduction. Lentiviruses were produced in 293FT cells (ATCC) as described (38, 61). Briefly, lentiviral vectors were co-transfected with the third generation packaging plasmids encoding gag/pol, REV and vesticular stomatitis virus G protein at a ratio 2:1 by lipofectamine 2000 (Invitrogen) into 293FT cells (DNA/lipofectimine=1 mg/3 ml). Viral supernatants were collected 72 hours after transfection and concentrated by ultracentrifugation to produce stock with titers of $4.8 \times 10^7$ to $8.1 \times 10^7$ infectious units per milliliter. Virus titers were 14 determined on Hela cells. To transduce normal hPSCs and t-hPSCs, $1.8 \times 10^7$ hPSCs and $1.5 \times 10^6$ t-hPSCs on day 1 after passage were transduced with viruses in MEF-CM supplemented with 8 ng/ml bFGF and 8 ng/ml polybrene (Chemicon international) for 24 hours. Multiplicities of infection (MOI) of 0.1 and 1 were used to transduce the cells with LL37_eGFP, LL37_DsRed, LLshOct4-1_eGFP, LLshOct4-2_eGFP, LLshOct4-3_GFP, LLshNanog_eGFP, LLshNanog-DsRed lentiviral vectors.

Isolation of hPSCs for Clonogencity Analysis. Transduced hPSCs and t-hPSCs were isolated using a FACSAria (BD Biosciences) and replated for the clonal assay previously described (17). Briefly, hPSCs were dissociated on day 2 after lentiviral transduction and stained with SSEA3 (Develop Studies Hybridoma Bank, mAB clone MC-631) and secondary AlexaFluor-647-goat-anti-mouse-IgG (Molecular Probes). $1 \times 10^4$ 7AAD-GFP+SSEA3+ cells were sorted with 94-98% purity and seeded on 12-well tissue culture plates coated with irradiated hPSC-derived fibroblast-like cells (ihdFs). 9 days after seeding, the number of GFP+ colonies was counted under fluorescent microscope (Olympus). t-hPSCs were dissociated 4 days after transduction and 7AAD-GFP+ t-hPSCs were sorted and plated at cell doses of $1 \times 10^4$, $1 \times 10^3$, $1 \times 10^2$ and 10 on 12-well and 96-well tissue culture plates coated with ihdFs. On day 6, total number of GFP+ colonies derived from t-hPSCs was counted under fluorescent microscope. Sorted hPSCs and t-hPSCs were expanded for other assays.

Flow Cytometry Analysis of Oct4, SSEA3, A2B5 and Annexin V hPSCs and t-hPSCs were treated with Collagenase IV for 7 to 10 minutes followed by cell dissociation buffer (Gibco) for 10 minutes at 37° C. Cells were rinsed and triturated to single cells in phosphate buffered saline (PBS) plus 3% FBS and filtered through a 40 mm cell strainer. For Oct4 staining, cells were fixed and stained with mouse anti-oct3-MAb (Beckton Dickinson) followed by secondary staining with either Alexa fluor 647 goat anti mouse IgG (Invitrogen) or 15 goat F (ab') 2 fragment anti-mouse IgG (H+L) PE. For SSEA3 staining, we used SSEA3 (Develop Studies Hybridoma Bank, mAb clone MC-631) and goat F(ab')2 fragment anti-mouse IgG (H+L) PE or FITC (Invitrogen) or Alexa fluor 647 goat anti mouse IgG (Invitrogen). A2B5 was detected with antibodies A2B5 (R&D systems) and Alexa fluor 647 goat anti mouse IgM (Invitrogen). Live cells were identified by 7-aminoactinomycin D (7-AAD) exclusion and analyzed for surfacemarker expression using FACSCalibur (BD Biosciences). The data were analyzed by FlowJo software (Tree Star). The apoptotic status of the cells was assessed using the AnnexinV apoptosis detection kit (BD Biosciences) according to the manufacturer's guidelines.

Teratoma Formation. $1.5 \times 10^4$, $3.3 \times 10^4$, $6.6 \times 10^4$ sorted Oct4 knockdown t-hPSCs were injected into the testis capsules of three male NOD/SCID mice in triplicate. Cell doses of $7.5 \times 10^3$, $2.4 \times 10^4$, and $6.6 \times 10^4$ t-hPSCs were also injected into 6 mice as control (See Example 1). After 6 weeks, teratomas were extracted, measured and fixed with 10% buffered formalin followed by embedding in paraffin. Five micron sectioned samples were stained with Hematoxalin and Eosin (H&E) and imaged under 200× magnification.

Quantitative Polymerase Chain Reaction (qPCR) Analysis. Total RNA from hPSCs and t-hPSCs was extracted by RNeasy Mini Kit (Qiagen) according to the manufacturer's instructions. cDNA synthesis was performed with 5 mg total RNA using by first-strand cDNA synthesis kit (Amersham Biosciences). Expression of Oct4, Nanog, Sox2, c-Myc, Dpp4a, and Tbx3 were quantified by quantitative PCR (Mx4000, Stratagene) using SYBR green (Invitrogen) DNA binding dye. Quantitative PCR reaction conditions were as follows: Primary denaturation at 95° C. for 1 min and 40 cycles of PCR consisting of 95° C. for 10 s, 60° C. for 1 min, and 72° C. for 30 s, followed by analyzing the amplified products using the dissociation curves. The signal intensities were normalized against GAPDH and the 2-DDCt equation was used to calculate the relative gene expressions (55).

Statistical Analysis. Results were presented as mean±SEM. Statistical significance was determined using an unpaired Student t test and results were considered significant or highly significant when $p<0.05$ or $<0.01$, respectively.

Example 5

Screening of t-hPSCs, hPSCs and iPSCs to Identify Compounds with Differential Activity Transformed human pluripotent stem cells (V1-H9) were seeded in mouse embryonic fibroblast-conditioned medium (MEFCM) to Matrigel coated 96-well plates at 3K cells/well. Normal human pluripotent stem cells (H9) and iPS1.2 cells were bulk-seeded in MEFCM to Matrigel coated 96-well plates.

After 24 h and 72 h the media was exchanged for MEFCM containing either 0.1% DMSO (control); 100 ng/ml BMP4; 100 nM Rapamycin or 100 nM retinoic acid. At least 4 wells per treatment were used for H9 and iPS1.2 cells; 3 wells per treatment for v1H9 cells. After 96 hours the cells were stained with Hoechst (8 µM for 20 minutes); washed with PBS; and nine fluorescence images per well were acquired at 10× (V1-H9) or 5× (H9 and iPS1.2) magnification with an ArrayScan automated microscope.

The number of cells (i.e. nuclear objects) per well was quantified from the Hoechst images using Perkin Elmer Acapella software. The cell-counts for each cell-line were then normalised to the median value of the control (0.1% DMSO) wells for that cell-line.

As shown in FIG. 28, screening and comparing the intereactions of t-hPSCs with hPSCs and iPS1.2 cells identified rapamycin as differentially affecting t-hPSCs compared to normal stem cells. t-hPSCs can therefore be used in screening methods to identify compounds that differentially or selectively affect t-hPSCs compared to normal stem cells.

Example 6

Screening Compounds Using t-hPSCs for Inducers of Stem Cell Differentiation 300 compounds were tested for the ability to induce stem cell differentiation using t-hPSCs that contain a vector comprising a Oct4-GFP reporter gene. t-hPSCs cells were dissociated to single cells and plated and culture in 96-well plates using MEFCM for 24 hrs before exposure to the compounds.

Plates containing the cells were analyzed 72 hours after exposure to the compounds using a fluorescence plate reader capable of detecting the fluorescence emitted from the Oct4-GFP reporter expressed in transformed cells and normalized to the relative cell nuclear number as defined by Hoechst staining. GFP/Hoechst ratios below zero, the threshold defined by BMP4 (a known stem cell differentiator), are considered potent inducers of stem cell differentiation. As shown in FIG. 29A, Thioridazine HCl, Mefloquine HCl and CWP 100 nM were identified as potent inducers of t-hPSCs differentiation.

Mefloquine (MEFLO) and thioridazine (THIO) were then tested in human iPS cells. Following 7 days of treatment, the frequency of Oct4+ cells were measured using flow cytometry and compared to culture media (MEFCM) and culture media supplemented with DMSO (DMSO) as a vehicle to augment compound solubility. As shown in FIG. 29B, the frequency of Oct4+ cells was found to decrease with both MEFLO and THIO indicating a loss of a key stem cell marker.

In order to further investigate the compounds identified by the screen, mefloquine and thioridazine were used to treat human mobilized peripheral blood for 5 days. Cell viability was measured using trypan blue exclusion. As shown in FIGS. 29C and D, mefloquine and thioridazine at various doses (0.1-10 µM) did not reduce cell viability relative to control samples (0 µM) indicating that these compounds are non-toxic to human cells. Mefloquine has been described as a treatment for hematological cancers (see for example WO03096992). The screening assays described herein which detect effects of compounds on transformed pluripotent stem cells which exhibit neoplastic features are therefore useful for screening for compounds that target t-hPSCs but are non-toxic to human cells. Compounds identified using the screening methods as described herein may also be tested using normal stem cells (i.e. non-transformed stem cells) in order to identify compounds that differentially or selectively interact with t-hPSCs, thereby identifying compounds that target cancer stem cells without targeting normal stem cells.

Example 7

Methods of Culturing Stem Cells for Use in High Throughput Screening

Pluripotent stem cells (embryonic or induced pluripotent Stem Cells) are traditionally cultured and passaged as bulk culture when a confluent or semi-confluent cell culture dish is disrupted by enzymatic and/or mechanical treatment to form small cell clusters that are then transferred into new dishes. Stem cell cultures are known to be heterogeneous containing cells with diverse differentiation potential and often multiple cell types (e.g. undifferentiated cells and human stem cell derived fibroblasts). It is generally accepted in this field that all cell types must be present in the culture in order to support stem cell development (Niche dependent cells). In addition, a balance between the proportion of undifferentiated vs differentiated cells is often sought upon cell passage in order to maintain the undifferentiated state of pluripotent stem cells in culture.

The conventional stem cell culture methods described above generate unpredictable results, showing great variability and consequently being inappropriate for high throughput or high content screening when wells are expected to display a certain level of equivalence and predictability in terms of the types and amounts of cells present and growth kinetics.

As set out below, the present Example describes improved culture methods for stem cells that exhibit reduced variability and are useful for use in screening methods such as high throughput screening methods.

Figure 30:
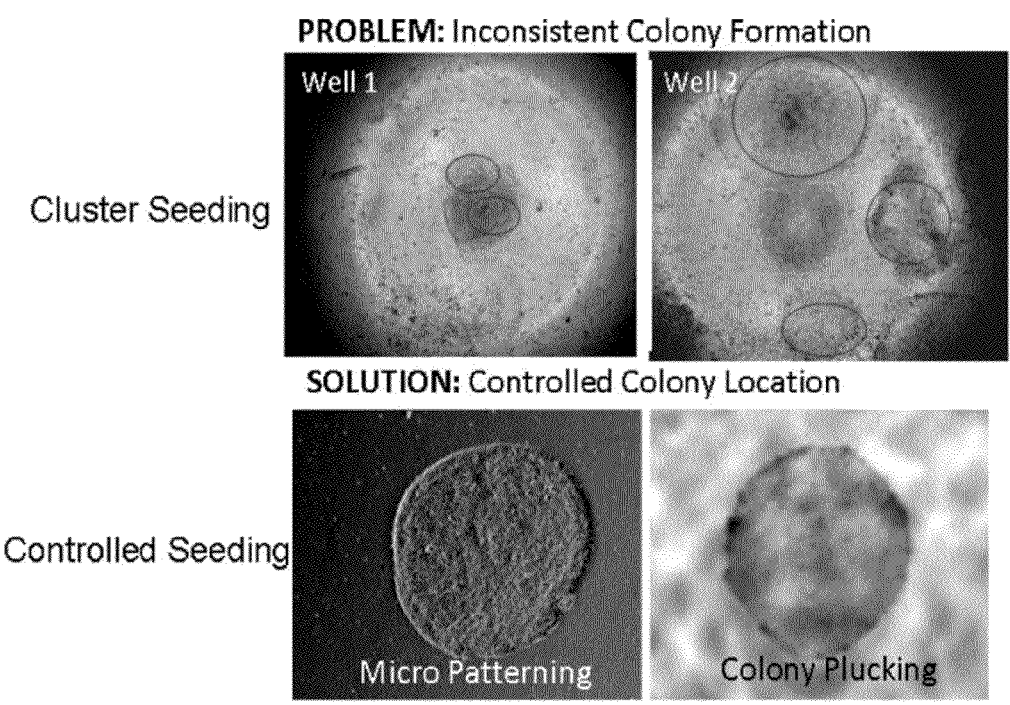
FIG. 30 shows cluster seeding of pluripotent stem cells versus predetermined colony localization. Note the inter-well variation in colony shape, location and numbers in cluster seeded wells (outlined, top two panels) while micro-patterning and colony plucking (lower two panels) give well defined and reproducible colonies.

Normal pluripotent stem cells were incubated with collagenase IV for 10 min before being scraped off and broken into clusters. The clusters were then seeded in the wells of matrigel coated 96 well microtitre plates. In order to address the inter-well variability resulting from cluster seeding (FIG. 30, top panels), methods were developed to restrict colony location to certain areas of the well. One method employed surface patterning technology to create adhesive and non-adhesive areas in the well. Specifically, a 1 ul droplet of matrigel was added to ultra-low adhesion plates and allowed to air dry. Clusters of normal cells seeded the well and only attached on the matrigel surface coating. It is noted that this method created a ring pattern (FIG. 30, bottom left panel). Alternatively, the matrigel droplet was added to tissue culture treated polystyrene dished and air-dried. A solution of Pluronics F68 (difunctional block copolymer surfactant from BASF) was then added to the well to convert the remaining area into a non-adhesive surface before being seeded with clusters of stem cells. This method created circular patterns for cell attachment. (FIG. 30, bottom left panel) This patterning method was complimented by plucking clusters from stem cell colonies and transferring these clusters directly onto the matrigel patterns (FIG. 30, bottom right panel).

Single Colony Plucking

In order to make single colony culture of human pluripotent stem cells in 96 well plates, undifferentiated single pluripotent stem cell clusters were transferred onto Matrigel-coated plates by the colony plucking technique illustrated in FIG. 30 bottom right panel and FIG. 31a. Similar size of undifferentiated clusters from full-grown colony were plucked using sharpen ended micropipetter tips (inner diameter, 400-500 µm). Punched clusters were detached by rotating tips and seeded onto the center of Matrigel-coated plates individually. To check the cell line and/or culture medium dependent variation, three different human pluripotent stem cell lines (two McMaster lines and one Harvard line) and two different culture media (DMEM/F12 and MEF-CM) were tested (data shown for iPS1.2 in FIG. 31b). At day 7 of single colony culture, individual colonies were dissociated into single cells with cell dissociation buffer and analyzed by cell number and human pluripotent stem cell-specific surface marker, SSEA3, expression by flow cytometry. These results demonstrate the maintenance of pluripotency in multiple human pluripotent stem cell lines in different media where MEF-CM proves to be a better culture medium.

High-Throughput Culture Conditions for hPSCs

Figure 31:
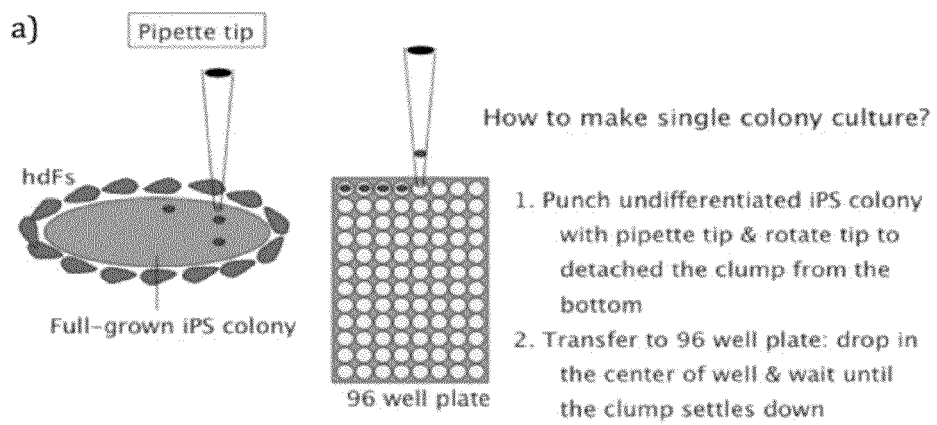
FIG. 31 shows (a) a single colony plucking procedure and (b) results of iPS1.2 cells cultured in two different culture media.
Figure 32:
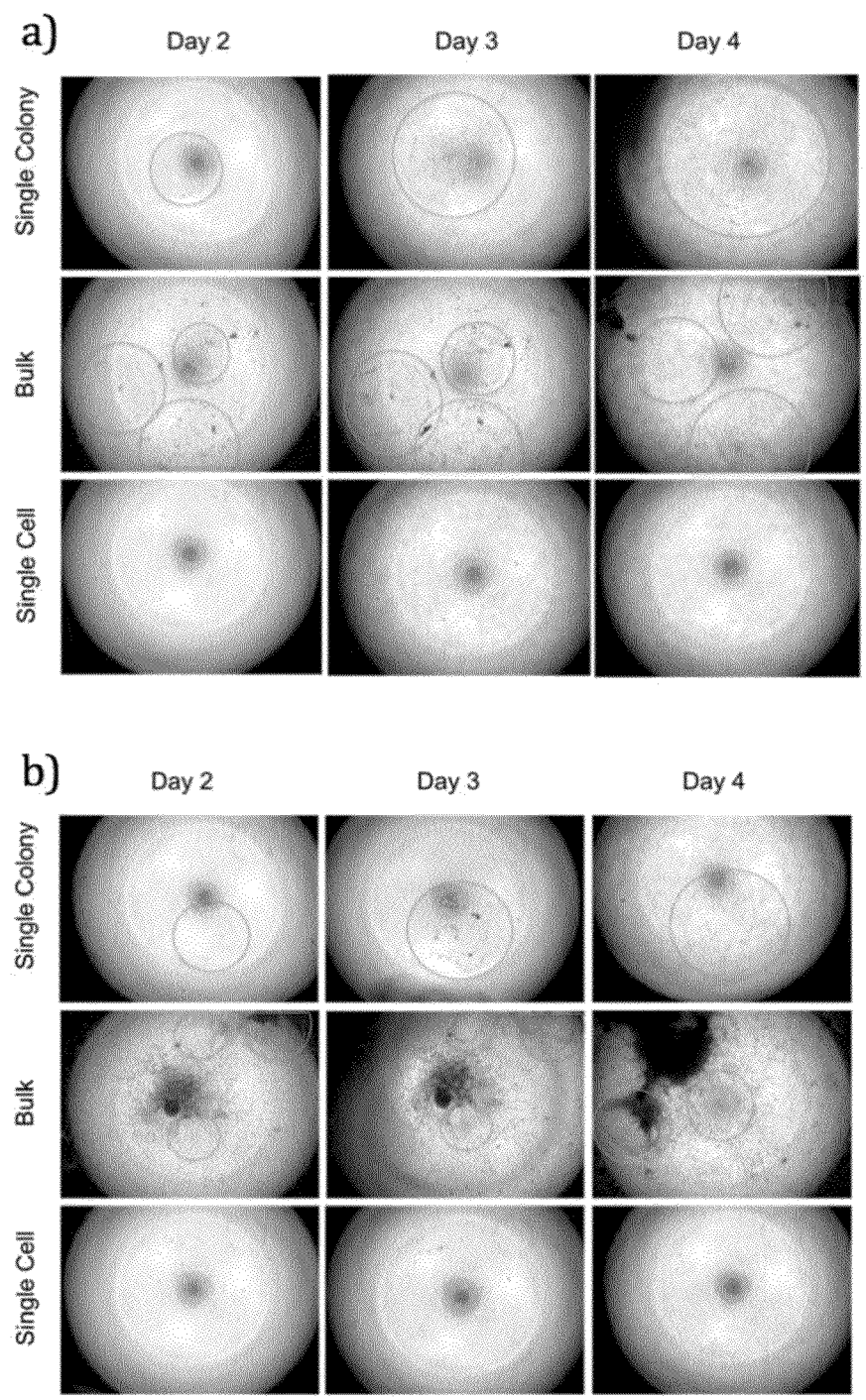
FIG. 32 shows phase contrast (40×) of a) iPS1.2 & b) hES H1 cells cultured in a 96 well plate as single colonies, bulk and single cells over 4 days. Images depict the advantage of single colony plucking when compared to bulk and single cell culture made apparent by the controlled colony localization.
Figure 33:
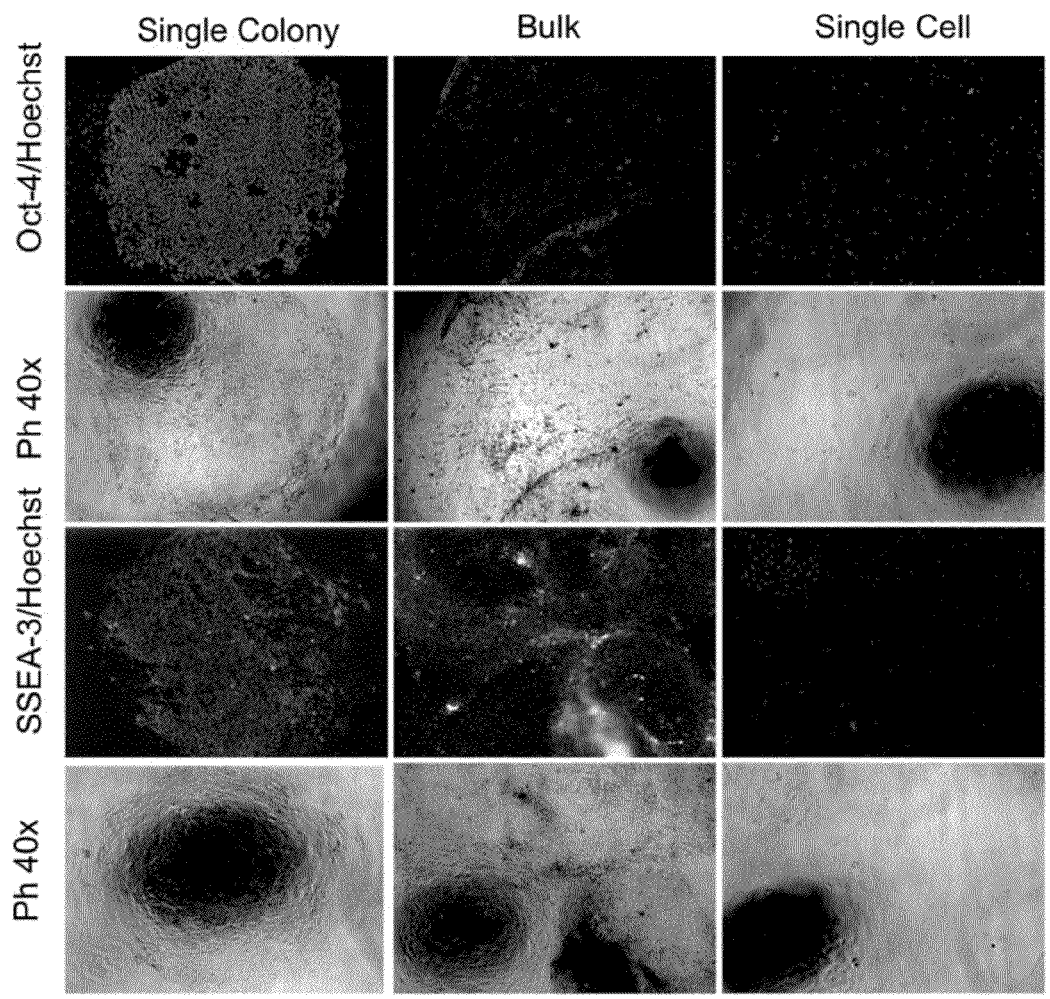
FIG. 33 shows the Oct-4 & SSEA-3 staining of iPS1.2 cultured via single colony plucking, bulk and single cell passaging. Images show the maintenance of pluripotency markers Oct-4 & SSEA-3 in single colony plucking versus bulk and single cell culture. [Note: Dark regions on phase contrast images represent the centre of the well].
Figure 34:
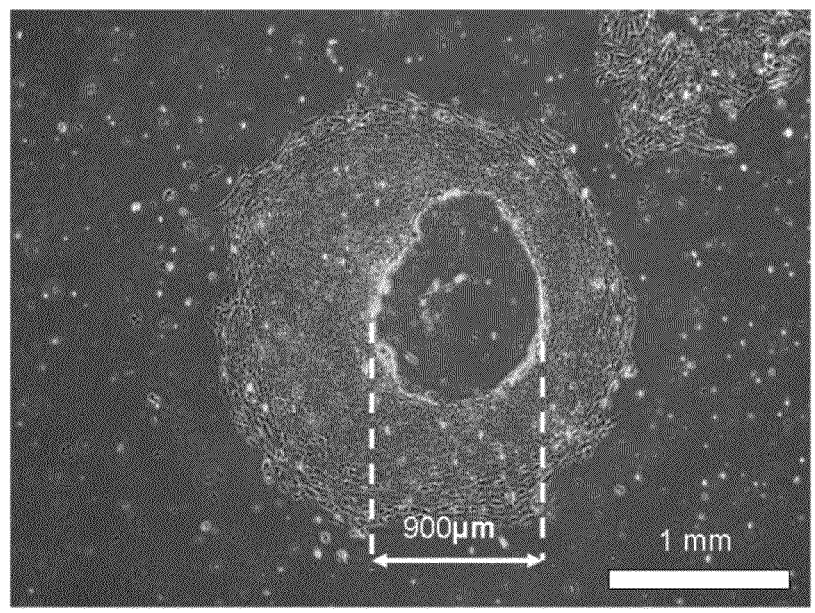
FIG. 34 shows the inner ⅓ of the colony removed by plucking. The cells transferred from the center are used for passaging and maintain the stem cells in pluripotent state.

In order to determine the ideal passaging conditions for human pluripotent stem cells in high-throughput and high-content formats three seeding conditions were compared: 1) Passaging as single cells via enzymatic dissociation with Trypsin, 2) Passaging in bulk via enzymatic dissociation with Collagenase IV, and 3) Single colony plucking as shown in FIG. 31. Colonies were manually centered into matrigel coated wells as described previously. These conditions were assayed for SSEA-3 and Oct-4, common markers for pluripotency, to compare the maintenance of pluripotency, proportion of undifferentiated to differentiated cells, inter and intra-well variation, colony-wall interactions and optical clarity. Human pluripotent stem cells (iPS1.2 and hES H1) were seeded into 96 well optical imaging plates and assayed at day 4. Cells were imaged under phase contrast (FIGS. 32a and 32b) then fixed with 2% paraformaldehyde, stained with antibodies for SSEA-3 and Oct-4 and imaged under a fluorescence microscope shown in FIG. 33. This comparison confirms that single colony plucking of human pluripotent stem cells is superior to both bulk and single cell passaging in a high-throughput format. This is made apparent by the maintenance of both SSEA-3 and Oct-4 after single colony plucking versus those colonies that were cultured as bulk and single cells. In comparison to single colony plucking, bulk cultures showed loss of pluripotency due to cell-wall interactions, inter-colony interactions and a disproportion among undifferentiated and differentiated cells which impeded the ability to accurately image colonies and thus reduced optical clarity. Single cell dissociation is not a feasible passaging method for high-throughput formats as most of the surviving cells are human stem cell derived fibroblasts (hDF's). Those that are Oct-4 positive do not have the capacity to maintain the niche necessary for pluripotency indicated by the loss of SSEA-3. Not only do these data make evident the advantage of single colony plucking but also provides information of the speed at which the wells can be screened. Wells containing single colonies plucked or seeded as clusters on patterned surfaces will allow rapid screening as there will be no uncertainties of which colonies to score as in bulk passaged wells containing randomly distributed colonies. Such variation in colony number, in addition to variation in colony size and proportion of differentiated to undifferentiated cells, may result in time consuming acquisition. This (bulk passaging) also makes difficult the use of automated scoring systems that require programmable scoring software which rely on example-based reiteration due to significant well-well variation.

Example 8

High Throughput Screening Methods and Bulk Culture Seeding in 48 and 96 Well Plates Comparisons between normal stem cells such as embryonic stem cells or induced pluripotent stem cells derived from skin and t-hPSCs are hampered by the difficulties in consistently plating normal stem cells for use in screening methods. Typically, normal stem cells plated as single cells differentiate making the comparison between the normal stem cells and t-hPSCs difficult. In particular, there is a need for methods to consistently plate stem cells suitable for high throughput screening such as in 48 or 96 well plates or other receptacles suitable for screening large numbers of compounds. Accordingly, the culture methods useful for to perform high throughput screening with cultures H9 or iPS1.2 stem cells were investigated. Normal stem cells plated and cultured using the methods described herein can also be used independently to screen for compounds that induce differentiation, proliferation or maintenance of pluripotency.

One confluent well of H9 or iPS1.2 cells was dissociated with Collagenase IV for 5 minutes at 37° C. then scraped with a 5 ml pipette in 2 ml MEFCM. The cells were then transferred to a 15 ml conical tube and triturated approximately 10 times to dissociate colonies into smaller clumps than standard trituration. The cell suspension was counted and diluted with MEFCM to achieve approximately 10,000 cells per 50 ul. 50 ul was aliquoted into each well containing 50 ul of MEFCM. The cell suspension was then transferred into a 25 ml reservoir to accommodate a 100 ul multichannel pipette fitted with 250 ul filtered pipette tips. The suspension was routinely mixed with the 250 ul tips facilitating the formation of smaller clump size to generate the "Bulk Fraction" seeding material.

The "Fraction 2" seeding material was prepared as for the "Bulk Fraction" seeding material above with the exception that the 2 mls of triturated cell suspension was passed through a 100 um strainer to filter out the differentiated clumps. The suspension was then counted to achieve 10,000 cells per 50 ul. In standard bulk culture, the cell suspension is triturated gently only a few times with a 5 ml pipette, generating much larger clumps.

Figure 35:
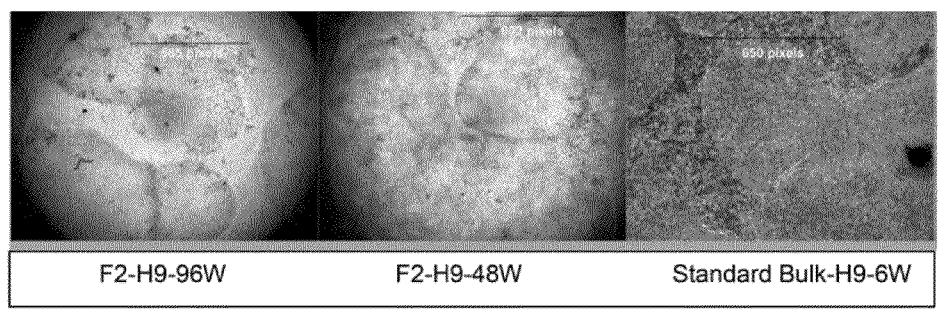
FIG. 35 shows colony sizes among seeding methods and plate formats after 1 week in culture as set out in Example 8.

FIG. 35 shows colony sizes among seeding methods (F2 seeding and standard bulk seeding in 96 and 48 well plate formats after 1 week in culture. This demonstrates that the F2 and bulk fraction seeding method do not alter colony size in such a way that would interfere with colony response.

Figure 36:
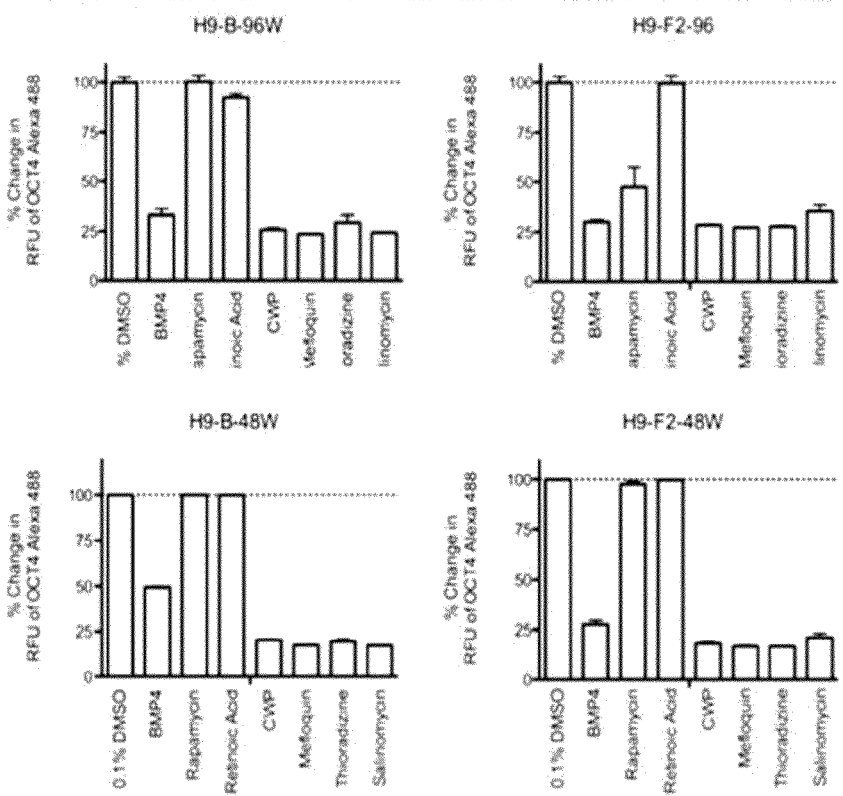
FIG. 36 shows the analysis of 96 & 48 well plates seeded with Fraction 2 (F2) versus New Bulk Fraction Seeding with H9 and iPS1.2 cells analyzed by a BMG Plate Reader with respect to the percent change in Oct-3/4 relative to a control group.
Figure 36:
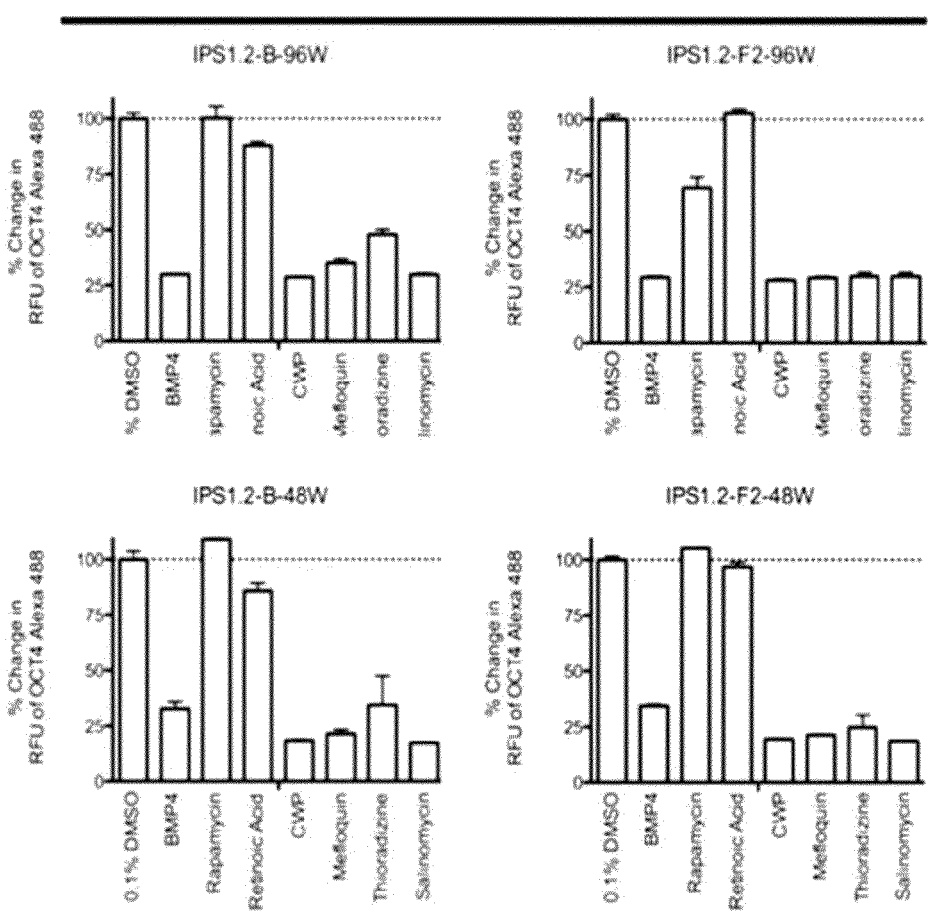

FIG. 36 shows the analysis of 96 & 48 well plates seeded with Fraction 2 (F2) and bulk fraction seeding with H9 and iPS1.2 cells analyzed by a BMG Plate Reader with respect to the percent change in Oct-3/4 relative to a control group. Cells seeded using this methodology showed lower interwell variability. In addition, this preparation allows for the minimization of overlapping between cells and higher assay reproducibility.

Similar results were observed for "Fraction 2" and bulk seeded cells screened using FACS Calibur for Alexa Fluor dye 488 conjugated to Oct-3/4, Alexa Fluor dye 555 conjugated to Sox2 antibodies or double positive for both Oct-3/4 and Sox2 or using Hoecsht 33342 and a BMG plate reader to compare the loss of Oct-3/4 over time in the different plate formats.

TABLE 1

Limiting dilution assay for t-hPSC$^{Oct4-KD}$ teratoma formation

| Mouse ID | Cell info | Number of cells injected (×10³) | Volume of mass (cm³) | Histology (HE) | Metastases | Lymphoma |
|---|---|---|---|---|---|---|
| 1# | t-hPSC$^{Oct4-KD}$ | 66 | 0.13 | 2 germ layers | No | No |
| 2# | t-hPSC$^{Oct4-KD}$ | 66 | 13.00 | 3 germ layers | No | No |

TABLE 1-continued

Limiting dilution assay for t-hPSC$^{Oct4-KD}$ teratoma formation

| Mouse ID | Cell info | Number of cells injected (×10³) | Volume of mass (cm³) | Histology (HE) | Metastases | Lymphoma |
|---|---|---|---|---|---|---|
| 3# | t-hPSC$^{Oct4-KD}$ | 66 | 3.00 | 3 germ layers | No | No |
| 4# | t-hPSC$^{Oct4-KD}$ | 33 | 2.40 | 3 germ layers | No | No |
| 5# | t-hPSC$^{Oct4-KD}$ | 33 | 3.74 | 3 germ layers | No | No |
| 6# | t-hPSC$^{Oct4-KD}$ | 33 | 8.64 | 3 germ layers | No | No |
| 7# | t-hPSC$^{Oct4-KD}$ | 15 | 1.60 | 3 germ layers | No | No |
| 8# | t-hPSC$^{Oct4-KD}$ | 15 | 1.98 | 3 germ layers | No | No |
| 9# | t-hPSC$^{Oct4-KD}$ | 15 | 9.60 | 2 germ layers | No | No |

Note:
Control testes are normal and around 0.14 g

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

References

1. Baker, D. E. et al. Adaptation to culture of human embryonic stem cells and oncogenesis in vivo. Nat. Biotechnol. 25, 207-215 (2007).
2. Caisander, G. et al. Chromosomal integrity maintained in five human embryonic stem cell lines after prolonged in vitro culture. Chromosome Res. 14, 131-137 (2006).
3. Inzunza, J. et al. Comparative genomic hybridization and karyotyping of human embryonic stem cells reveals the occurrence of an isodicentric X chromosome after long-term cultivation. Mol. Hum. Reprod. 10, 461-466 (2004).
4. Rosier, E. S. et al. Long-term culture of human embryonic stem cells in feeder-free conditions. Dev. Dyn. 229, 259-274 (2004).
5. Imreh, M. P. et al. In vitro culture conditions favoring selection of chromosomal abnormalities in human ES cells. J. Cell. Biochem. 99, 508-516 (2006).
6. Cowan, C. A. et al. Derivation of embryonic stem-cell lines from human blastocysts. N. Engl. J. Med. 350, 1353-1356 (2004).
7. Brimble, S. N. et al. Karyotypic stability, genotyping, differentiation, feeder-free maintenance, and gene expression sampling in three human embryonic stem cell lines derived prior to Aug. 9, 2001. Stem Cells Dev. 13, 585-597 (2004).
8. Draper, J. S. et al. Recurrent gain of chromosomes 17q and 12 in cultured human embryonic stem cells. Nat. Biotechnol. 22, 53-54 (2004).
9. Maitra, A. et al. Genomic alterations in cultured human embryonic stem cells. Nat. Genet. 37, 1099-1103 (2005).
10. Enver, T. et al. Cellular differentiation hierarchies in normal and culture-adapted human embryonic stem cells. Hum. Mol. Genet. 14, 3129-3140 (2005).
11. Herszfeld, D. et al. CD30 is a survival factor and a biomarker for transformed human pluripotent stem cells. Nat. Biotechnol. 24, 351-357 (2006).
12. Mitalipova, M. M. et al. Preserving the genetic integrity of human embryonic stem cells. Nat. Biotechnol. 23, 19-20 (2005).
13. Ludwig, T. E. et al. Derivation of human embryonic stem cells in defined conditions. Nat. Biotechnol. 24, 185-187 (2006).
14. Yang, S. et al. Tumor progression of culture-adapted human embryonic stem cells during long-term culture. Genes Chromosom. Cancer 47, 665-679 (2008).
15. Ben-Porath, I. et al. An embryonic stem cell-like gene expression signature in poorly differentiated aggressive human tumors. Nat. Genet. 40, 499-507 (2008).
16. Lodish, H. et al. Molecular Cell Biology edn. 3 (W.H. Freeman & Co., New York, 1995).
17. Stewart, M. H. et al. Clonal isolation of hES cells reveals heterogeneity within the pluripotent stem cell compartment. Nat. Methods 3, 807-815 (2006).
18. Bendall, S. C. et al. IGF and FGF cooperatively establish the regulatory stem cell niche of pluripotent human cells in vitro. Nature 448, 1015-1021 (2007).
19. Hook, E. B. Exclusion of chromosomal mosaicism: tables of 90%, 95%, and 99% confidence limits and comments on use. Am. J. Hum. Genet. 29, 94-97 (1977).
20. Levenstein, M. et al. Basic fibroblast growth factor support of human embryonic stem cell self-renewal. Stem Cells 24, 568-574 (2004).
21. Lensch, M. W. & Ince, T. A. The terminology of teratocarcinomas and teratomas. Nat. Biotechnol. 25, 1211 author reply, 1211-1212 (2007).
22. Damjanov, I. & Andrews, P. W. The terminology of teratocarcinomas and teratomas. Nat. Biotechnol. 25, 1212 editorial reply, 1212 (2007).
23. Boyer, L. A. et al. Core transcriptional regulatory circuitry in human embryonic stem cells. Cell 122, 947-956 (2005).
24. Lee, T. I. et al. Control of developmental regulators by Polycomb in human embryonic stem cells. Cell 125, 301-313 (2006).
25. Boyer, L. A. et al. Polycomb complexes repress developmental regulator in murine embryonic stem cells. Nature 441, 349-353 (2006).
26. Spits, C. et al. Recurrent chromosomal abnormalities in human embryonic stem cells. Nat. Biotechnol. 26, 1361-1363 (2008).
27. Lefort, N. et al. Human embryonic stem cells reveal recurrent genomic instability at 20q11.21. Nat. Biotechnol. 26, 1364-1366 (2008).
28. Singh, S. K. et al. Identification of human brain tumour initiating cells. Nature 432, 396-401 (2004).
29. O'Brien, C. A., Pollett, A., Gallinger, S. & Dick, J. E. A human colon cancer cell capable of initiating tumour growth in immunodeficient mice. Nature 445, 106-110 (2007).
30. Ricci-Vitiani, L. et al. Identification and expansion of human colon-cancer-initiating cells. Nature 445, 111-115 (2007).
31. Shmelkov, S. V. et al. CD133 expression is not restricted to stem cells, and both CD133+ and CD133– metastatic colon cancer cells initiate tumors. J. Clin. Invest. 118, 2111-2120 (2008).

32. Postovit, L. M. et al. Human embryonic stem cell microenvironment suppresses the tumorigenic phenotype of aggressive cancer cells. Proc. Natl. Acad. Sci. USA 105, 4329-4334 (2008).
33. Chadwick, K. et al. Cytokines and BMP-4 promote hematopoietic differentiation of human embryonic stem cells. Blood 102, 906-915 (2003).
34. Al-Hajj, M., Wicha, M. S., Benito-Hernandez, A., Morrison, S. J., and Clarke, M. F. (2003). Prospective identification of tumorigenic breast cancer cells. Proc Natl Acad Sci USA 100, 3983-3988.
35. Alldridge, L., Metodieva, G., Greenwood, C., Al-Janabi, K., Thwaites, L., Sauven, P., and Metodiev, M. (2008). Proteome profiling of breast tumors by gel electrophoresis and nanoscale electrospray ionization mass spectrometry. J Proteome Res 7, 1458-1469.
36. Bonnet, D., and Dick, J. E. (1997). Human acute myeloid leukemia is organized as a hierarchy that originates from a primitive hematopoietic cell. Nat Med 3, 730-737.
37. Boyer, L. A., Mathur, D., and Jaenisch, R. (2006). Molecular control of pluripotency. Curr Opin Genet Dev 16, 455-462.
38. Burns, J. C., Friedmann, T., Driever, W., Burrascano, M., and Yee, J. K. (1993). Vesicular stomatitis virus G glycoprotein pseudotyped retroviral vectors: concentration to very high titer and efficient gene transfer into mammalian and nonmammalian cells. Proc Natl Acad Sci USA 90, 8033-8037.
39. Bussolati, B., Bruno, S., Grange, C., Ferrando, U., and Camussi, G. (2008). Identification of a tumor-initiating stem cell population in human renal carcinomas. Faseb J 22, 3696-3705.
40. Chambers, I., Colby, D., Robertson, M., Nichols, J., Lee, S., Tweedie, S., and Smith, A. (2003). Functional expression cloning of Nanog, a pluripotency sustaining factor in embryonic stem cells. Cell 113, 643-655.
41. Chang, C. C., Shieh, G. S., Wu, P., Lin, C. C., Shiau, A. L., and Wu, C. L. (2008). Oct-3/4 expression reflects tumor progression and regulates motility of bladder cancer cells. Cancer Res 68, 6281-6291.
42. Chew, J. L., Loh, Y. H., Zhang, W., Chen, X., Tam, W. L., Yeap, L. S., Li, P., Ang, Y. S., Lim, B., Robson, P., and Ng, H. H. (2005). Reciprocal transcriptional regulation of Pou5f1 and Sox2 via the Oct4/Sox2 complex in embryonic stem cells. Mol Cell Biol 25, 6031-6046.
43. Chiou, S. H., Yu, C. C., Huang, C. Y., Lin, S. C., Liu, C. J., Tsai, T. H., Chou, S. H., Chien, C. S., Ku, H. H., and Lo, J. F. (2008). Positive correlations of Oct-4 and Nanog in oral cancer stem-like cells and high-grade oral squamous cell carcinoma. Clin Cancer Res 14, 4085-4095.
44. Dick, J. E. (2008). Stem cell concepts renew cancer research. Blood 112, 4793-4807.
45. Ezeh, U. I., Turek, P. J., Reijo, R. A., and Clark, A. T. (2005). Human embryonic stem cell genes OCT4, NANOG, STELLAR, and GDF3 are expressed in both seminoma and breast carcinoma. Cancer 104, 2255-2265.
46. Gidekel, S., Pizov, G., Bergman, Y., and Pikarsky, E. (2003). Oct-3/4 is a dosedependent oncogenic fate determinant. Cancer Cell 4, 361-370.
47. Hochedlinger, K., Yamada, Y., Beard, C., and Jaenisch, R. (2005). Ectopic expression of Oct-4 blocks progenitor-cell differentiation and causes dysplasia in epithelial tissues. Cell 121, 465-477.
48. Hoei-Hansen, C. E. (2008). Application of stem cell markers in search for neoplastic germ cells in dysgenetic gonads, extragonadal tumours, and in semen of infertile men. Cancer Treat Rev 34, 348-367.
49. Jeter, C. R., Badeaux, M., Choy, G., Chandra, D., Patrawala, L., Liu, C., Calhoun-Davis, T., Zaehres, H., Daley, G. Q., and Tang, D. G. (2009). Functional evidence that the self-renewal gene NANOG regulates human tumor development. Stem Cells 27, 993-1005.
50. Jordan, C. T. (2009). Cancer stem cells: controversial or just misunderstood? Cell Stem Cell 4, 203-205.
51. Kim, C. F., Jackson, E. L., Woolfenden, A. E., Lawrence, S., Babar, I., Vogel, S., Crowley, D., Bronson, R. T., and Jacks, T. (2005). Identification of bronchioalveolar stem cells in normal lung and lung cancer. Cell 121, 823-835.
52. Knoepfler, P. S. (2009). Deconstructing stem cell tumorigenicity: a roadmap to safe regenerative medicine. Stem Cells 27, 1050-1056.
53. Lengner, C. J., Camargo, F. D., Hochedlinger, K., Welstead, G. G., Zaidi, S., Gokhale, S., Scholer, H. R., Tomilin, A., and Jaenisch, R. (2007). Oct4 expression is not required for mouse somatic stem cell self-renewal. Cell Stem Cell 1, 403-415.
54. Lessard, J., and Sauvageau, G. (2003). Bmi-1 determines the proliferative capacity of normal and leukaemic stem cells. Nature 423, 255-260.
55. Livak, K. J., and Schmittgen, T. D. (2001). Analysis of relative gene expression data using real-time quantitative PCR and the 2(-Delta Delta C(T)) Method. Methods 25, 402-408.
56. Loh, Y. H., Wu, Q., Chew, J. L., Vega, V. B., Zhang, W., Chen, X., Bourque, G., George, J., Leong, B., Liu, J., et al. (2006). The Oct4 and Nanog transcription network regulates pluripotency in mouse embryonic stem cells. Nat Genet 38, 431-440.
57. Matin, M. M., Walsh, J. R., Gokhale, P. J., Draper, J. S., Bahrami, A. R., Morton, I., Moore, H. D., and Andrews, P. W. (2004). Specific knockdown of Oct4 and beta2-microglobulin expression by RNA interference in human embryonic stem cells and embryonic carcinoma cells. Stem Cells 22, 659-668.
58. Mitsui, K., Tokuzawa, Y., Koh, H., Segawa, K., Murakami, M., Takahashi, K., Maruyama, M., Maeda, M., and Yamanaka, S. (2003). The homeoprotein Nanog is required for maintenance of pluripotency in mouse epiblast and ES cells. Cell 113, 631-642.
59. Niwa, H., Miyazaki, J., and Smith, A. G. (2000). Quantitative expression of Oct-3/4 defines differentiation, dedifferentiation or self-renewal of ES cells. Nat Genet 24, 372-376.
60. Rodda, D. J., Chew, J. L., Lim, L. H., Loh, Y. H., Wang, B., Ng, H. H., and Robson, P. (2005). Transcriptional regulation of nanog by OCT4 and SOX2. J Biol Chem 280, 24731-24737.
61. Rubinson, D. A., Dillon, C. P., Kwiatkowski, A. V., Sievers, C., Yang, L., Kopinja, J., Rooney, D. L., Zhang, M., Ihrig, M. M., McManus, M. T., et al. (2003). A lentivirus-based system to functionally silence genes in primary mammalian cells, stem cells and transgenic mice by RNA interference. Nat Genet 33, 401-406.
62. Somervaille, T. C., Matheny, C. J., Spencer, G. J., Iwasaki, M., Rinn, J. L., Witten, D. M., Chang, H. Y., Shurtleff, S. A., Downing, J. R., and Cleary, M. L. (2009). Hierarchical maintenance of MLL myeloid leukemia stem cells employs a transcriptional program shared with embryonic rather than adult stem cells. Cell Stem Cell 4, 129-140.
63. Sumi, T., Tsuneyoshi, N., Nakatsuji, N., and Suemori, H. (2007). Apoptosis and differentiation of human embryonic stem cells induced by sustained activation of c-Myc. Oncogene 26, 5564-5576.

64. Werbowetski-Ogilvie, T. E., Bosse, M., Stewart, M., Schnerch, A., Ramos-Mejia, V., Rouleau, A., Wynder, T., Smith, M. J., Dingwall, S., Carter, T., et al. (2009). Characterization of human embryonic stem cells with features of neoplastic progression. Nat Biotechnol 27, 91-97.
65. Wong, D. J., Liu, H., Ridky, T. W., Cassarino, D., Segal, E., and Chang, H. Y. (2008). Module map of stem cell genes guides creation of epithelial cancer stem cells. Cell Stem Cell 2, 333-344.
66. Ye, F., Zhou, C., Cheng, Q., Shen, J., and Chen, H. (2008). Stem-cell-abundant proteins Nanog, Nucleostemin and Musashil are highly expressed in malignant cervical epithelial cells. BMC Cancer 8, 108.
67. Zaehres, H., Lensch, M. W., Daheron, L., Stewart, S. A., Itskovitz-Eldor, J., and Daley, G. Q. (2005). High-efficiency RNA interference in human embryonic stem cells. Stem Cells 23, 299-305.
68. Zhang, S., Balch, C., Chan, M. W., Lai, H. C., Matei, D., Schilder, J. M., Yan, P. S., Huang, T. H., and Nephew, K. P. (2008). Identification and characterization of ovarian cancer-initiating cells from primary human tumors. Cancer Res 68, 4311-4320.
69. Hotta et al. Isolation of human iPS cells using EOS lentiviral vectors to select for pluripotency. Nat Methods 2009 6(5): 370-376.

The invention claimed is:

1. A transformed human pluripotent stem cell (t-hPSC) produced by the variant human embryonic stem cell line deposited with the International Depositary of Canada (IDAC), under Accession No. 220715-01, and designated v-hESC-1, wherein the cell does not require bFGF for maintenance of an undifferentiated state, maintains expression of SSEA3 in the absence of bFGF, co-expresses FGFR1 and IGFR1, has an amplification of at least 0.8 megabase at 20q 11.1-11.2 and grows in a monolayer.

2. The transformed human pluripotent stem cell of claim 1, wherein the cell has been passaged as a single cell.

3. A cell culture comprising a plurality of transformed human pluripotent stem cells (t-hPSCs) of claim 1.

4. The cell culture of claim 3, wherein the cell culture is a monolayer without cell overlap.

5. The cell culture of claim 3, wherein the cell culture is passaged from a single cell.

* * * * *